(12) United States Patent
Horlitz et al.

(10) Patent No.: US 10,676,780 B2
(45) Date of Patent: *Jun. 9, 2020

(54) STABILISATION AND ISOLATION OF EXTRACELLULAR NUCLEIC ACIDS

(71) Applicant: QIAGEN GmbH, Hilden (DE)

(72) Inventors: Martin Horlitz, Hilden (DE);
Annabelle Schubert, Hilden (DE);
Markus Sprenger-Haussels, Hilden (DE)

(73) Assignee: QIAGEN GMbH, Hilden (DE)

( * ) Notice: Subject to any disclaimer, the term of this patent is extended or adjusted under 35 U.S.C. 154(b) by 873 days.

This patent is subject to a terminal disclaimer.

(21) Appl. No.: 14/347,048

(22) PCT Filed: Sep. 25, 2012

(86) PCT No.: PCT/EP2012/068893
§ 371 (c)(1),
(2) Date: Mar. 25, 2014

(87) PCT Pub. No.: WO2013/045458
PCT Pub. Date: Apr. 4, 2013

(65) Prior Publication Data
US 2014/0227687 A1    Aug. 14, 2014

Related U.S. Application Data

(60) Provisional application No. 61/539,274, filed on Sep. 26, 2011.

(30) Foreign Application Priority Data

Sep. 26, 2011 (EP) .................................... 11182818

(51) Int. Cl.
| | | |
|---|---|---|
| *C12Q 1/68* | (2018.01) | |
| *C12Q 1/6806* | (2018.01) | |
| *C12N 15/10* | (2006.01) | |
| *B01L 3/00* | (2006.01) | |
| *B01L 7/00* | (2006.01) | |

(52) U.S. Cl.
CPC .......... *C12Q 1/6806* (2013.01); *B01L 3/5082* (2013.01); *C12N 15/1003* (2013.01); *B01L 7/52* (2013.01); *B01L 2200/16* (2013.01)

(58) Field of Classification Search
CPC .................................................. C12Q 1/6806
USPC ........................................................ 435/6.1
See application file for complete search history.

(56) References Cited

U.S. PATENT DOCUMENTS

| | | |
|---|---|---|
| 3,389,133 A | 6/1968 | Gutcho |
| 3,903,179 A | 9/1975 | Bacha et al. |
| 4,555,487 A | 11/1985 | Yamada et al. |
| 4,938,961 A | 7/1990 | Collins et al. |
| 5,459,073 A | 10/1995 | Ryan |
| 5,460,797 A | 10/1995 | Ryan |
| 5,705,628 A | 1/1998 | Hawkins |
| 5,811,268 A | 9/1998 | Gerl et al. |
| 5,860,397 A | 1/1999 | Schafer |
| 5,898,071 A | 4/1999 | Hawkins |
| 6,379,930 B1 | 4/2002 | Dattagupta et al. |
| 6,407,107 B1 | 6/2002 | Gilbert et al. |
| 6,534,262 B1 | 3/2003 | McKernan et al. |
| 6,602,718 B1 | 8/2003 | Augello et al. |
| 6,617,170 B2 | 9/2003 | Augello et al. |
| 6,673,364 B1 | 1/2004 | Holland et al. |
| 6,776,959 B1 | 8/2004 | Helftenbein |
| 7,270,953 B2 | 9/2007 | Hollander et al. |
| 7,332,277 B2 | 2/2008 | Dhallan |
| 7,442,506 B2 | 10/2008 | Dhallan |
| 2003/0118980 A1 | 6/2003 | Taylor |
| 2004/0043505 A1 | 3/2004 | Walenciak et al. |
| 2004/0167165 A1 | 8/2004 | Shankar et al. |
| 2004/0253661 A1 | 12/2004 | Goldrick et al. |
| 2005/0158699 A1 | 7/2005 | Kadkade et al. |
| 2006/0014177 A1 | 1/2006 | Hogan et al. |
| 2006/0147944 A1 | 7/2006 | Chomczynski |
| 2006/0212020 A1 | 9/2006 | Rainen et al. |
| 2007/0208166 A1 | 9/2007 | Baly et al. |
| 2008/0176209 A1 | 7/2008 | Muller et al. |
| 2008/0187924 A1 | 8/2008 | Korfhage et al. |
| 2008/0257207 A1 | 10/2008 | Rengaswamy et al. |
| 2009/0017438 A1 | 1/2009 | Roy et al. |
| 2009/0017439 A1 | 1/2009 | Shimko et al. |
| 2009/0274765 A1 | 11/2009 | Beduneau et al. |

(Continued)

FOREIGN PATENT DOCUMENTS

| | | |
|---|---|---|
| AU | 2011253662 A1 | 12/2011 |
| EP | 0 578 885 A2 | 1/1994 |

(Continued)

OTHER PUBLICATIONS

Notice of Reasons for Refusal with English Translation, dated Jun. 1, 2016, for Japanese Application No. 2014-532357, 11 pages.
Anonymous, "Caspase Inhibitor," BD™ ApoBlock—Technical Data Sheet (2 pages) (2008).
Baechler et al., "Expression levels for many genes in human peripheral blood cells are highly sensitive to ex vivo incubation," *Genes and Immunity* 5:347-353 (2004).
Caserta et al., "Q-VD-Oph, a broad spectrum caspase inhibitor with potent antiapoptotic properties," *Apoptosis* 8(4):345-352 (2003).
Chiu et al., "Effects of Blood-Processing Protocols on Fetal and Total DNA Quantification in Maternal Plasma," *Clinical Chemistry* 47(9):1607-1613 (2001).
Fan et al., "Analysis of the Size Distributions of Fetal and Maternal Cell-Free DNA by Paired-End Sequencing," *Clinical Chemistry* 56(8):1-8 (2010).

(Continued)

*Primary Examiner* — Jezia Riley
(74) *Attorney, Agent, or Firm* — Seed IP Law Group LLP

(57) ABSTRACT

The present invention provides methods, compositions and devices for stabilizing the extracellular nucleic acid population in a cell-containing biological sample using an apoptosis inhibitor, preferably a caspase inhibitor, a hypertonic agent and/or a compound according to formula (1) as defined in the claims.

27 Claims, 29 Drawing Sheets

Specification includes a Sequence Listing.

(56) References Cited

U.S. PATENT DOCUMENTS

| | | | |
|---|---|---|---|
| 2010/0009349 A1 | 1/2010 | Holländer | |
| 2010/0137575 A1 | 6/2010 | Connolly et al. | |
| 2010/0184069 A1 | 7/2010 | Fernando et al. | |
| 2010/0209930 A1 | 8/2010 | Fernando | |
| 2010/0255524 A1* | 10/2010 | Hollander | C12N 15/1003 435/29 |
| 2010/0280233 A1 | 11/2010 | Connolly et al. | |
| 2010/0285468 A1 | 11/2010 | Xin | |
| 2010/0311166 A1 | 12/2010 | Florio et al. | |
| 2011/0027771 A1 | 2/2011 | Deng | |
| 2011/0111410 A1 | 5/2011 | Ryan et al. | |
| 2011/0306668 A1 | 12/2011 | Yu et al. | |
| 2012/0064021 A1 | 3/2012 | Leplanquais et al. | |
| 2012/0253071 A1 | 10/2012 | Rau et al. | |
| 2013/0323793 A1 | 12/2013 | Tanner et al. | |
| 2014/0227687 A1 | 8/2014 | Horlitz et al. | |
| 2014/0227688 A1 | 8/2014 | Horlitz et al. | |
| 2015/0056604 A1 | 2/2015 | Sehgal | |

FOREIGN PATENT DOCUMENTS

| | | |
|---|---|---|
| EP | 0 880 537 B1 | 12/2004 |
| EP | 2 256 196 A1 | 4/2006 |
| GB | 2 496 969 A | 5/2013 |
| JP | 2009-521949 A | 6/2009 |
| JP | 2009-522542 A | 6/2009 |
| JP | 2011-109987 A | 6/2011 |
| WO | 95/21849 A1 | 8/1995 |
| WO | 97/34015 A1 | 9/1997 |
| WO | 97/35589 A1 | 10/1997 |
| WO | 98/29126 | 7/1998 |
| WO | 98/41651 A1 | 9/1998 |
| WO | 99/57318 A2 | 11/1999 |
| WO | 01/60517 A2 | 8/2001 |
| WO | 01/70279 A1 | 9/2001 |
| WO | 03/018757 A2 | 3/2003 |
| WO | 03/086480 A1 | 10/2003 |
| WO | 2004/024958 A1 | 3/2004 |
| WO | 2004/032750 A1 | 4/2004 |
| WO | 2004/072228 A2 | 8/2004 |
| WO | 2005/067388 A2 | 7/2005 |
| WO | 2005/081867 A2 | 9/2005 |
| WO | 2006/017295 A2 | 2/2006 |
| WO | 2006/097806 A1 | 9/2006 |
| WO | 2007/077199 | 7/2007 |
| WO | 2007/077560 A2 | 7/2007 |
| WO | 2008/081166 A1 | 7/2008 |
| WO | 2008/145710 A1 | 12/2008 |
| WO | 2009/016255 A1 | 2/2009 |
| WO | 2010/057184 A1 | 5/2010 |
| WO | 2010/096323 A1 | 8/2010 |
| WO | 2011/026027 A1 | 3/2011 |
| WO | 2011/026028 A1 | 3/2011 |
| WO | 2011/057061 A1 | 5/2011 |
| WO | 2011/057184 A1 | 5/2011 |
| WO | 2011/157678 A1 | 12/2011 |
| WO | 2012/151450 A1 | 11/2012 |
| WO | 2013/045432 A1 | 4/2013 |
| WO | 2013/045434 A1 | 4/2013 |
| WO | 2013/045457 A1 | 4/2013 |
| WO | 2013/045458 A1 | 4/2013 |
| WO | 2013/053855 A1 | 4/2013 |
| WO | 2014/049022 A1 | 4/2014 |
| WO | 2014/055936 A1 | 4/2014 |
| WO | 2014/131906 A1 | 9/2014 |
| WO | 2014/146780 A1 | 9/2014 |
| WO | 2014/146781 A1 | 9/2014 |
| WO | 2014/146782 A1 | 9/2014 |
| WO | 2015/140218 A1 | 9/2015 |
| WO | 2016/022433 A1 | 2/2016 |
| WO | 2009/038853 A2 | 3/2018 |

OTHER PUBLICATIONS

Fernando et al., "Preservation and Amplification of Fetal Cell-Free DNA in Maternal Plasma for Noninvasive Prenatal Diagnosis," *Streck*, First Presented at AACC/ASCLS Clinical Lab Expo on Jul. 23, 2009.

Fernando et al., "Stabilization of Cell-Free RNA in Plasma for Noninvasive Diagnosis," *Streck*, Presented at AACC Annual Meeting Jul. 2010, Anaheim, CA.

Fleischhacker et al., "Circulating nucleic Acids (CNAs) and cancer—A Survey," *Biochimica et Biophysica Acta* 1775:181-232 (2007).

Fleischhacker, "Biology of Circulating mRNA—Still More Questions Than Answers?" *Ann. N.Y. Acad. Sci.* 1075:40-49 (2006).

Hromadnikova et al., "Quantification of Fetal and Total Circulatory DNA in Maternal Plasma Samples Before and After Size Fractionation by Agarose Gel Electrophoresis," *DNA and Cell Biology* 26(11):635-640 (2006).

Kruhøffer et al., "Isolation of Microarray-Grade Total RNA, MicroRNA, and DNA from a Single PAXgene Blood RNA Tube," *Journal of Molecular Diagnostics* 9(4):452-458 (2007).

Müller et al., "Improvement of molecular monitoring of residual disease in leukemias by bedside RNA stabilization," *Leukemia* 16:2395-2399 (2002).

Mukae et al., "Molecular cloning and characterization of human caspase-activated DNase," *Proc. Natl. Acad. Sci. USA* 95:9123-9128 (1998).

Pahl et al., "Gene expression changes in blood after phlebotomy: implications for gene expression profiling," *Blood* 100(3) (2 pages) (2002).

QIAamp® Circulating Nucleic Acid Handbook, QIAGEN®—Sample & Assay Technologies (44 pages) (May 2009).

Rainen et al., "Stabilization of mRNA Expression in Whole Blood Samples," *Clinical Chemistry* 48(11):1883-1890 (2002).

Sethu et al., "Microfluidic Isolation of Leukocytes from Whole Blood for Phenotype and Gene Expression Analysis," *Anal. Chem.* 76:5453-5461 (2006).

Swarup et al., "Circulating (cell-free) nucleic acids—A promising, non-invasive tool for early detection of several human diseases," *FEBS Letters* 581:795-799 (2007).

BD Pharmingen, Technical Data Sheet, "Z-VAD-FMK, General Caspase Inhibitor," (2 pages) (2008).

DeAngelis et al., "Solid-phase reversible immobilization for the isolation of PCR products," *Nucleic Acids Research* 23(22):4742-4743 (1995).

Decision of Rejection corresponding to Chinese Patent Application No. 201280046949.4, English Translation, 3 pages, dated May 25, 2018.

Dupuis et al., "Molecular-crowding effects on single-molecule RNA folding/unfolding thermodynamics and kinetics," *PNAS* 111(23):8464-8469 (Jun. 10, 2014).

Eckert et al., "Caspase inhibitors," *Cell Death and Differentiation* 6:1081-1086, 1999.

MP Biomedicals, "Q-VD-OPH (OPH109), a new generation broad caspase inhibitor from innovators of Z-VAD(OMe)-FMK Casper Inhibitor / Apoptosis Inhibitor," downloaded from https://www.mpbio.com/detailed_info.php?family_key=03OPH109&country=223 on Sep. 5, 2017, 5 pages.

Goldstein et al., "Caspase-independent cytochrome c release is a sensitive measure of low-level apoptosis in cell culture models," *Aging Cell* 4(4):217-222 (2005).

Jani et al., "Caspase Inhibition Prevents the Increase in Caspase-3, -2, -8 and -9 Activity and Apoptosis in the Cold Ischemic Mouse Kidney," *American Journal of Transplantation* 4:1246-1254, 2004.

Karimata et al., "Stabilization of a DNA duplex under molecular crowding conditions of PEG," *Nucleic Acids Symposium Series No. 48*:107-108 (2004).

Ke et al., "Characterizing DNA Condensation and Conformational Changes in Organic Solvents," *PLoS ONE* 5(10): 2010, 8 pages.

Lis et al., "Size fractionation of double-stranded DNA by precipitation with polyethylene glycol," *Nucleic Acids Research* 2(3):383-389 (Mar. 1975).

(56) References Cited

OTHER PUBLICATIONS

Marino et al., "Lysosomal and mitochondrial permeabilization mediates zinc(II) cationic phthalocyanine phototoxicity," *The International Journal of Biochemistry & Cell Biology* 45:2553-2562 (2013).

Mosbah et al., "Effects of Polyethylene Glycol and Hydroxethyl Starch in University of Wisconsin Preservation Solution on Human Red Blood Cell Aggregation and Viscosity," *Transplantation Proceedings* 38:1229-1235 (2006).

Paithankar et al., "Precipitation of DNA by polyethylene glycol and ethanol," Nucleic Acids Research 19(6):1346 (Feb. 6, 1991).

Samejima et al., "Trashing the Genome: the Role of Nucleases During Apoptosis," *Nature Reviews* 6:677-688, 2005.

Xu, "Guidance Book of Malignant Higher Education Examinations for Tumor Chemotherapy and Strategies Thereof for National Self-Taught Chinese Medicine Majors," (Bachelor) with Partial English Translation, 7 pages, (2002).

Zhao et al., "Collection of Essays at 60th Anniversary of Animal Society of China for Commemorating 100th Anniversary of Professor Chen Zhen's Birth," with Partial English Translation, 6 pages, (1994).

\* cited by examiner

SEQUENCE LISTING

```
<160> NUMBER OF SEQ ID NOS: 72

<210> SEQ ID NO 1
<211> LENGTH: 5
<212> TYPE: PRT
<213> ORGANISM: Unknown
<220> FEATURE:
<223> OTHER INFORMATION: Bax-Inhibiting peptide, V5

<400> SEQUENCE: 1

Val Pro Met Leu Lys
1               5

<210> SEQ ID NO 2
<211> LENGTH: 6
<212> TYPE: PRT
<213> ORGANISM: Unknown
<220> FEATURE:
<223> OTHER INFORMATION: STAT3 Inhibitor peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: PHOSPHORYLATION

<400> SEQUENCE: 2

Pro Tyr Leu Lys Thr Lys
1               5

<210> SEQ ID NO 3
<211> LENGTH: 4
<212> TYPE: PRT
<213> ORGANISM: Artificial
<220> FEATURE:
<223> OTHER INFORMATION: Group III Caspase Inhibitor I
<220> FEATURE:
<221> NAME/KEY: MOD_RES
<222> LOCATION: (1)..(1)
<223> OTHER INFORMATION: ACETYLATION
<220> FEATURE:
```

```
<221> NAME/KEY: MOD_RES
<222> LOCATION: (4)..(4)
<223> OTHER INFORMATION: BLOCKED

<400> SEQUENCE: 3

Ile Glu Pro Asp
1

<210> SEQ ID NO 4
<211> LENGTH: 4
<212> TYPE: PRT
<213> ORGANISM: Artificial
<220> FEATURE:
<223> OTHER INFORMATION: Caspase 3, 7 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 4

Asp Glu Val Asp
1

<210> SEQ ID NO 5
<211> LENGTH: 4
<212> TYPE: PRT
<213> ORGANISM: Artificial
<220> FEATURE:
<223> OTHER INFORMATION: Caspase 8 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: BLOCKED
<220> FEATURE:
<221> NAME/KEY: MOD_RES
<222> LOCATION: (4)..(4)
<223> OTHER INFORMATION: METHYLATION

<400> SEQUENCE: 5

Leu Glu Thr Asp
1

<210> SEQ ID NO 6
<211> LENGTH: 4
<212> TYPE: PRT
<213> ORGANISM: Artificial
<220> FEATURE:
<223> OTHER INFORMATION: Caspase 1, 4 inhibitor
<220> FEATURE:
```

```
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (4)..(4)
<223> OTHER INFORMATION: BLOCKED
<220> FEATURE:
<221> NAME/KEY: MOD_RES
<222> LOCATION: (4)..(4)
<223> OTHER INFORMATION: METHYLATION

<400> SEQUENCE: 6

Tyr Val Ala Asp
1

<210> SEQ ID NO 7
<211> LENGTH: 4
<212> TYPE: PRT
<213> ORGANISM: Artificial
<220> FEATURE:
<223> OTHER INFORMATION: Caspase 10 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 7

Ala Glu Val Asp
1

<210> SEQ ID NO 8
<211> LENGTH: 4
<212> TYPE: PRT
<213> ORGANISM: Artificial
<220> FEATURE:
<223> OTHER INFORMATION: Caspase 12 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 8

Ala Thr Ala Asp
1

<210> SEQ ID NO 9
<211> LENGTH: 4
<212> TYPE: PRT
<213> ORGANISM: Artificial
<220> FEATURE:
<223> OTHER INFORMATION: Caspase 4 inhibitor
<220> FEATURE:
```

-continued

```
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 9

Leu Glu Val Asp
1

<210> SEQ ID NO 10
<211> LENGTH: 4
<212> TYPE: PRT
<213> ORGANISM: Artificial
<220> FEATURE:
<223> OTHER INFORMATION: Caspase 13 inhibitor, reversible
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 10

Leu Glu Glu Asp
1

<210> SEQ ID NO 11
<211> LENGTH: 4
<212> TYPE: PRT
<213> ORGANISM: Artificial
<220> FEATURE:
<223> OTHER INFORMATION: Caspase 13 inhibitor, irreversible
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (3)..(3)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 11

Leu Glu Glu Asp
1

<210> SEQ ID NO 12
<211> LENGTH: 4
<212> TYPE: PRT
```

-continued

```
<213> ORGANISM: Artificial
<220> FEATURE:
<223> OTHER INFORMATION: inhibitor of anti-APO-1 induced apoptosis in
      L929-APO-1 cells
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 12

Tyr Val Ala Asp
1

<210> SEQ ID NO 13
<211> LENGTH: 20
<212> TYPE: PRT
<213> ORGANISM: Artificial
<220> FEATURE:
<223> OTHER INFORMATION: Caspase 1 Inhibitor I, cell-permeable
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (20)..(20)
<223> OTHER INFORMATION: BLOCKED

<400> SEQUENCE: 13

Ala Ala Val Ala Leu Leu Pro Ala Val Leu Leu Ala Leu Leu Ala Pro
1               5                   10                  15

Tyr Val Ala Asp
            20

<210> SEQ ID NO 14
<211> LENGTH: 4
<212> TYPE: PRT
<213> ORGANISM: Artificial
<220> FEATURE:
<223> OTHER INFORMATION: Caspase 1 Inhibitor II, cell permeable
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 14

Tyr Val Ala Asp
1

<210> SEQ ID NO 15
<211> LENGTH: 4
<212> TYPE: PRT
<213> ORGANISM: Artificial
<220> FEATURE:
<223> OTHER INFORMATION: Caspase 1 inhibitor IV, cell permeable
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED
```

```
-continued

<400> SEQUENCE: 15

Tyr Val Ala Asp
1

<210> SEQ ID NO 16
<211> LENGTH: 4
<212> TYPE: PRT
<213> ORGANISM: Artificial
<220> FEATURE:
<223> OTHER INFORMATION: Caspase 1 Inhibitor VI, cell permeable
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (4)..(4)
<223> OTHER INFORMATION: BLOCKED
<220> FEATURE:
<221> NAME/KEY: MOD_RES
<222> LOCATION: (4)..(4)
<223> OTHER INFORMATION: METHYLATION

<400> SEQUENCE: 16

Tyr Val Ala Asp
1

<210> SEQ ID NO 17
<211> LENGTH: 5
<212> TYPE: PRT
<213> ORGANISM: Artificial
<220> FEATURE:
<223> OTHER INFORMATION: Caspase 2 Inhibitor I
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (5)..(5)
<223> OTHER INFORMATION: METHYLATION
<220> FEATURE:
<221> NAME/KEY: MOD_RES
<222> LOCATION: (5)..(5)
<223> OTHER INFORMATION: BLOCKED

<400> SEQUENCE: 17

Val Asp Val Ala Asp
1               5

<210> SEQ ID NO 18
<211> LENGTH: 5
<212> TYPE: PRT
<213> ORGANISM: Artificial
<220> FEATURE:
<223> OTHER INFORMATION: Caspase 2 Inhibitor II
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: BLOCKED

<400> SEQUENCE: 18

Leu Asp Glu Ser Asp
1               5
```

```
<210> SEQ ID NO 19
<211> LENGTH: 4
<212> TYPE: PRT
<213> ORGANISM: Artificial
<220> FEATURE:
<223> OTHER INFORMATION: Caspase 3 Inhibitor I
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 19

Asp Glu Val Asp
1

<210> SEQ ID NO 20
<211> LENGTH: 20
<212> TYPE: PRT
<213> ORGANISM: Artificial
<220> FEATURE:
<223> OTHER INFORMATION: Caspase 3 Inhibitor I, cell permeable
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (20)..(20)
<223> OTHER INFORMATION: BLOCKED

<400> SEQUENCE: 20

Ala Ala Val Ala Leu Leu Pro Ala Val Leu Leu Ala Leu Leu Ala Pro
1               5                   10                  15

Asp Glu Val Asp
            20

<210> SEQ ID NO 21
<211> LENGTH: 4
<212> TYPE: PRT
<213> ORGANISM: Artificial
<220> FEATURE:
<223> OTHER INFORMATION: Caspase 3 Inhibitor II
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 21

Asp Glu Val Asp
1
```

```
<210> SEQ ID NO 22
<211> LENGTH: 4
<212> TYPE: PRT
<213> ORGANISM: Artificial
<220> FEATURE:
<223> OTHER INFORMATION: Caspase 3 Inhibitor III
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 22

Asp Glu Val Asp
1

<210> SEQ ID NO 23
<211> LENGTH: 4
<212> TYPE: PRT
<213> ORGANISM: Artificial
<220> FEATURE:
<223> OTHER INFORMATION: Caspase 3 Inhibitor IV
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 23

Asp Met Gln Asp
1

<210> SEQ ID NO 24
<211> LENGTH: 4
<212> TYPE: PRT
<213> ORGANISM: Artificial
<220> FEATURE:
<223> OTHER INFORMATION: Caspase 3 Inhibitor V
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 24

Asp Gln Met Asp
1

<210> SEQ ID NO 25
<211> LENGTH: 4
<212> TYPE: PRT
<213> ORGANISM: Artificial
<220> FEATURE:
<223> OTHER INFORMATION: Caspase 4 Inhibitor I
<220> FEATURE:
```

```
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 25

Leu Glu Val Asp
1

<210> SEQ ID NO 26
<211> LENGTH: 20
<212> TYPE: PRT
<213> ORGANISM: Artificial
<220> FEATURE:
<223> OTHER INFORMATION: Caspase 4 Inhibitor I, cell permeable
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (20)..(20)
<223> OTHER INFORMATION: BLOCKED

<400> SEQUENCE: 26

Ala Ala Val Ala Leu Leu Pro Ala Val Leu Leu Ala Leu Leu Ala Pro
1               5                   10                  15

Leu Glu Val Asp
            20

<210> SEQ ID NO 27
<211> LENGTH: 4
<212> TYPE: PRT
<213> ORGANISM: Artificial
<220> FEATURE:
<223> OTHER INFORMATION: Caspase 5 Inhibitor I
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 27

Trp Glu His Asp
1

<210> SEQ ID NO 28
<211> LENGTH: 4
<212> TYPE: PRT
<213> ORGANISM: Artificial
<220> FEATURE:
<223> OTHER INFORMATION: Caspase 6 Inhibitor I
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
```

```
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 28

Val Glu Ile Asp
1

<210> SEQ ID NO 29
<211> LENGTH: 20
<212> TYPE: PRT
<213> ORGANISM: Artificial
<220> FEATURE:
<223> OTHER INFORMATION: Caspase 6 Inhibitor II, cell permeable
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (20)..(20)
<223> OTHER INFORMATION: BLOCKED

<400> SEQUENCE: 29

Ala Ala Val Ala Leu Leu Pro Ala Val Leu Leu Ala Leu Leu Ala Pro
1               5                   10                  15

Val Glu Ile Asp
            20

<210> SEQ ID NO 30
<211> LENGTH: 20
<212> TYPE: PRT
<213> ORGANISM: Artificial
<220> FEATURE:
<223> OTHER INFORMATION: Caspase 8 Inhibitor I, cell permeable
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (20)..(20)
<223> OTHER INFORMATION: BLOCKED

<400> SEQUENCE: 30

Ala Ala Val Ala Leu Leu Pro Ala Val Leu Leu Ala Leu Leu Ala Pro
1               5                   10                  15

Ile Glu Thr Asp
            20

<210> SEQ ID NO 31
<211> LENGTH: 4
<212> TYPE: PRT
<213> ORGANISM: Artificial
<220> FEATURE:
<223> OTHER INFORMATION: Caspase 8 Inhibitor II
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
<223> OTHER INFORMATION: METHYLATION
```

```
<220> FEATURE:
<221> NAME/KEY: MOD_RES
<222> LOCATION: (4)..(4)
<223> OTHER INFORMATION: BLOCKED
<220> FEATURE:
<221> NAME/KEY: MOD_RES
<222> LOCATION: (4)..(4)
<223> OTHER INFORMATION: METHYLATION

<400> SEQUENCE: 31

Ile Glu Thr Asp
1

<210> SEQ ID NO 32
<211> LENGTH: 4
<212> TYPE: PRT
<213> ORGANISM: Artificial
<220> FEATURE:
<223> OTHER INFORMATION: Caspase 9 Inhibitor I
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: BLOCKED
<220> FEATURE:
<221> NAME/KEY: MOD_RES
<222> LOCATION: (4)..(4)
<223> OTHER INFORMATION: METHYLATION

<400> SEQUENCE: 32

Leu Glu His Asp
1

<210> SEQ ID NO 33
<211> LENGTH: 20
<212> TYPE: PRT
<213> ORGANISM: Artificial
<220> FEATURE:
<223> OTHER INFORMATION: Caspase 9 Inhibitor II, cell permeable
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (20)..(20)
<223> OTHER INFORMATION: BLOCKED

<400> SEQUENCE: 33

Ala Ala Val Ala Leu Leu Pro Ala Val Leu Leu Ala Leu Leu Ala Pro
1               5                   10                  15

Leu Glu His Asp
            20

<210> SEQ ID NO 34
<211> LENGTH: 4
<212> TYPE: PRT
<213> ORGANISM: Artificial
<220> FEATURE:
<223> OTHER INFORMATION: Caspase 9 Inhibitor III
<220> FEATURE:
<221> NAME/KEY: MOD_RES
<222> LOCATION: (1)..(1)
<223> OTHER INFORMATION: ACETYLATION
<220> FEATURE:
```

```
<221> NAME/KEY: MOD_RES
<222> LOCATION: (4)..(4)
<223> OTHER INFORMATION: BLOCKED

<400> SEQUENCE: 34

Leu Glu His Asp
1

<210> SEQ ID NO 35
<211> LENGTH: 19
<212> TYPE: PRT
<213> ORGANISM: Artificial
<220> FEATURE:
<223> OTHER INFORMATION: Pan-Caspase Inhibitor II, cell permeable
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (19)..(19)
<223> OTHER INFORMATION: BLOCKED

<400> SEQUENCE: 35

Ala Ala Val Ala Leu Leu Pro Ala Val Leu Leu Ala Leu Leu Ala Pro
1               5                   10                  15

Val Ala Asp

<210> SEQ ID NO 36
<211> LENGTH: 5
<212> TYPE: PRT
<213> ORGANISM: Artificial
<220> FEATURE:
<223> OTHER INFORMATION: Caspase Inhibitor VIII
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: BLOCKED

<400> SEQUENCE: 36

Val Asp Val Ala Asp
1               5

<210> SEQ ID NO 37
<211> LENGTH: 4
<212> TYPE: PRT
<213> ORGANISM: Artificial
<220> FEATURE:
<223> OTHER INFORMATION: caspase 1 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 37

Tyr Val Ala Asp
1
```

```
<210> SEQ ID NO 38
<211> LENGTH: 4
<212> TYPE: PRT
<213> ORGANISM: Artificial
<220> FEATURE:
<223> OTHER INFORMATION: caspase 1 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 38

Trp Glu His Asp
1

<210> SEQ ID NO 39
<211> LENGTH: 4
<212> TYPE: PRT
<213> ORGANISM: Artificial
<220> FEATURE:
<223> OTHER INFORMATION: caspase 1 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 39

Tyr Val Ala Asp
1

<210> SEQ ID NO 40
<211> LENGTH: 4
<212> TYPE: PRT
<213> ORGANISM: Artificial
<220> FEATURE:
<223> OTHER INFORMATION: caspase 1 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 40

Tyr Val Ala Asp
1

<210> SEQ ID NO 41
<211> LENGTH: 4
<212> TYPE: PRT
<213> ORGANISM: Artificial
<220> FEATURE:
<223> OTHER INFORMATION: caspase 1 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 41
```

Tyr Val Ala Asp
1

<210> SEQ ID NO 42
<211> LENGTH: 4
<212> TYPE: PRT
<213> ORGANISM: Artificial
<220> FEATURE:
<223> OTHER INFORMATION: caspase 1 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 42

Tyr Val Lys Asp
1

<210> SEQ ID NO 43
<211> LENGTH: 4
<212> TYPE: PRT
<213> ORGANISM: Artificial
<220> FEATURE:
<223> OTHER INFORMATION: caspase 1 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (4)..(4)
<223> OTHER INFORMATION: BLOCKED

<400> SEQUENCE: 43

Tyr Val Ala Asp
1

<210> SEQ ID NO 44
<211> LENGTH: 5
<212> TYPE: PRT
<213> ORGANISM: Artificial
<220> FEATURE:
<223> OTHER INFORMATION: caspase 2 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: BLOCKED

<400> SEQUENCE: 44

Val Asp Val Ala Asp
1               5

<210> SEQ ID NO 45
<211> LENGTH: 5
<212> TYPE: PRT
<213> ORGANISM: Artificial
<220> FEATURE:
<223> OTHER INFORMATION: caspase 2 inhibitor
<220> FEATURE:
<221> NAME/KEY: MOD_RES
<222> LOCATION: (1)..(1)
<223> OTHER INFORMATION: BLOCKED
<220> FEATURE:

```
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (5)..(5)
<223> OTHER INFORMATION: BLOCKED
<220> FEATURE:
<221> NAME/KEY: MOD_RES
<222> LOCATION: (5)..(5)
<223> OTHER INFORMATION: METHYLATION

<400> SEQUENCE: 45

Val Asp Val Ala Asp
1               5

<210> SEQ ID NO 46
<211> LENGTH: 4
<212> TYPE: PRT
<213> ORGANISM: Artificial
<220> FEATURE:
<223> OTHER INFORMATION: caspase 3 precursor inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 46

Glu Ser Met Asp
1

<210> SEQ ID NO 47
<211> LENGTH: 4
<212> TYPE: PRT
<213> ORGANISM: Artificial
<220> FEATURE:
<223> OTHER INFORMATION: caspase 3 precursor inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 47

Ile Glu Thr Asp
1

<210> SEQ ID NO 48
<211> LENGTH: 4
<212> TYPE: PRT
<213> ORGANISM: Artificial
<220> FEATURE:
<223> OTHER INFORMATION: caspase 3 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 48

Asp Glu Val Asp
1
```

```
<210> SEQ ID NO 49
<211> LENGTH: 4
<212> TYPE: PRT
<213> ORGANISM: Artificial
<220> FEATURE:
<223> OTHER INFORMATION: caspase 3 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 49

Asp Met Gln Asp
1

<210> SEQ ID NO 50
<211> LENGTH: 4
<212> TYPE: PRT
<213> ORGANISM: Artificial
<220> FEATURE:
<223> OTHER INFORMATION: Caspase 3/7 Inhibitor II
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 50

Asp Gln Met Asp
1

<210> SEQ ID NO 51
<211> LENGTH: 4
<212> TYPE: PRT
<213> ORGANISM: Artificial
<220> FEATURE:
<223> OTHER INFORMATION: Caspase 3/7 Inhibitor II
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (4)..(4)
<223> OTHER INFORMATION: BLOCKED

<400> SEQUENCE: 51

Asp Glu Val Asp
1

<210> SEQ ID NO 52
<211> LENGTH: 4
<212> TYPE: PRT
<213> ORGANISM: Artificial
<220> FEATURE:
<223> OTHER INFORMATION: Caspase 3/7 Inhibitor II
```

<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (1)..(1)
<223> OTHER INFORMATION: METHYLATION
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 52

Asp Glu Val Asp
1

<210> SEQ ID NO 53
<211> LENGTH: 4
<212> TYPE: PRT
<213> ORGANISM: Artificial
<220> FEATURE:
<223> OTHER INFORMATION: caspase 4 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 53

Leu Glu Val Asp
1

<210> SEQ ID NO 54
<211> LENGTH: 4
<212> TYPE: PRT
<213> ORGANISM: Artificial
<220> FEATURE:
<223> OTHER INFORMATION: caspase 4 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (4)..(4)
<223> OTHER INFORMATION: BLOCKED

<400> SEQUENCE: 54

Tyr Val Ala Asp
1

<210> SEQ ID NO 55
<211> LENGTH: 4
<212> TYPE: PRT
<213> ORGANISM: Artificial
<220> FEATURE:
<223> OTHER INFORMATION: caspase 6 inhibitor
<220> FEATURE:
<221> NAME/KEY: MOD_RES
<222> LOCATION: (1)..(1)
<223> OTHER INFORMATION: ACETYLATION

```
<220> FEATURE:
<221> NAME/KEY: MOD_RES
<222> LOCATION: (4)..(4)
<223> OTHER INFORMATION: BLOCKED

<400> SEQUENCE: 55

Val Glu Ile Asp
1

<210> SEQ ID NO 56
<211> LENGTH: 4
<212> TYPE: PRT
<213> ORGANISM: Artificial
<220> FEATURE:
<223> OTHER INFORMATION: caspase 6 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 56

Val Glu Ile Asp
1

<210> SEQ ID NO 57
<211> LENGTH: 4
<212> TYPE: PRT
<213> ORGANISM: Artificial
<220> FEATURE:
<223> OTHER INFORMATION: caspase 8 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 57

Ile Glu Pro Asp
1

<210> SEQ ID NO 58
<211> LENGTH: 4
<212> TYPE: PRT
<213> ORGANISM: Artificial
<220> FEATURE:
<223> OTHER INFORMATION: caspase 8 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (4)..(4)
<223> OTHER INFORMATION: BLOCKED

<400> SEQUENCE: 58

Ala Glu Val Asp
```

-continued

```
<210> SEQ ID NO 59
<211> LENGTH: 4
<212> TYPE: PRT
<213> ORGANISM: Artificial
<220> FEATURE:
<223> OTHER INFORMATION: caspase 8 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 59

Ile Glu Thr Asp
1

<210> SEQ ID NO 60
<211> LENGTH: 4
<212> TYPE: PRT
<213> ORGANISM: Artificial
<220> FEATURE:
<223> OTHER INFORMATION: caspase 8 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (2)..(2)
<223> OTHER INFORMATION: METHYLATION
<220> FEATURE:
<221> NAME/KEY: MOD_RES
<222> LOCATION: (4)..(4)
<223> OTHER INFORMATION: METHYLATION
<220> FEATURE:
<221> NAME/KEY: MOD_RES
<222> LOCATION: (4)..(4)
<223> OTHER INFORMATION: BLOCKED

<400> SEQUENCE: 60

Leu Glu Thr Asp
1

<210> SEQ ID NO 61
<211> LENGTH: 4
<212> TYPE: PRT
<213> ORGANISM: Artificial
<220> FEATURE:
<223> OTHER INFORMATION: caspase 9 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 61

Leu Glu His Asp
```

```
<210> SEQ ID NO 62
<211> LENGTH: 4
<212> TYPE: PRT
<213> ORGANISM: Artificial
<220> FEATURE:
<223> OTHER INFORMATION: caspase 9 inhibitor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 62

Leu Glu His Asp
1

<210> SEQ ID NO 63
<211> LENGTH: 4
<212> TYPE: PRT
<213> ORGANISM: Artificial
<220> FEATURE:
<223> OTHER INFORMATION: caspase 10 inhibitor
<220> FEATURE:
<221> NAME/KEY: MOD_RES
<222> LOCATION: (1)..(1)
<223> OTHER INFORMATION: BLOCKED
<220> FEATURE:
<221> NAME/KEY: MOD_RES
<222> LOCATION: (4)..(4)
<223> OTHER INFORMATION: BLOCKED

<400> SEQUENCE: 63

Ala Glu Val Asp
1

<210> SEQ ID NO 64
<211> LENGTH: 4
<212> TYPE: PRT
<213> ORGANISM: Artificial
<220> FEATURE:
<223> OTHER INFORMATION: Granzyme B Inhibitor II
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: BLOCKED

<400> SEQUENCE: 64

Ile Glu Thr Asp
1

<210> SEQ ID NO 65
<211> LENGTH: 4
<212> TYPE: PRT
<213> ORGANISM: Artificial
<220> FEATURE:
<223> OTHER INFORMATION: Granzyme B Inhibitor IV
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
```

```
<223> OTHER INFORMATION: BLOCKED

<400> SEQUENCE: 65

Ile Glu Pro Asp
1

<210> SEQ ID NO 66
<211> LENGTH: 22
<212> TYPE: DNA
<213> ORGANISM: Artificial
<220> FEATURE:
<223> OTHER INFORMATION: human ribosomal DNA forward primer

<400> SEQUENCE: 66
gccgctagag gtgaaattct tg                                                  22

<210> SEQ ID NO 67
<211> LENGTH: 21
<212> TYPE: DNA
<213> ORGANISM: Artificial
<220> FEATURE:
<223> OTHER INFORMATION: human ribosomal DNA reverse primer

<400> SEQUENCE: 67
cattcttggc aaatgctttc g                                                   21

<210> SEQ ID NO 68
<211> LENGTH: 21
<212> TYPE: DNA
<213> ORGANISM: Artificial
<220> FEATURE:
<223> OTHER INFORMATION: human ribosomal DNA probe

<400> SEQUENCE: 68
accggcgcaa gacggaccag a                                                   21

<210> SEQ ID NO 69
<211> LENGTH: 22
<212> TYPE: DNA
<213> ORGANISM: Artificial
<220> FEATURE:
<223> OTHER INFORMATION: human ribosomal DNA forward primer

<400> SEQUENCE: 69
gtcgctcgct cctctcctac tt                                                  22

<210> SEQ ID NO 70
<211> LENGTH: 19
<212> TYPE: DNA
<213> ORGANISM: Artificial
<220> FEATURE:
<223> OTHER INFORMATION: human ribosomal DNA reverse primer

<400> SEQUENCE: 70
ggctgctggc accagactt                                                      19

<210> SEQ ID NO 71
<211> LENGTH: 25
<212> TYPE: DNA
<213> ORGANISM: Artificial
<220> FEATURE:
<223> OTHER INFORMATION: human ribosomal DNA probe

<400> SEQUENCE: 71
ctaatacatg ccgacgggcg ctgac                                               25
```

```
<210> SEQ ID NO 72
<211> LENGTH: 18
<212> TYPE: DNA
<213> ORGANISM: Artificial
<220> FEATURE:
<223> OTHER INFORMATION: human ribosomal DNA forward primer

<400> SEQUENCE: 72
gaattgacgg aagggcac                                                 18
```

STABILISATION AND ISOLATION OF EXTRACELLULAR NUCLEIC ACIDS

The work leading to this invention has received funding from the European Community's Seventh Framework Programme (FP7/2007-2013) under grant agreement no 222916.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 760204_401USPC_SEQUENCE_LISTING.txt. The text file is 22.4 KB, was created on Mar. 24, 2014, and is being submitted electronically via EFS-Web.

FIELD OF THE INVENTION

The technology disclosed herein relates to methods and compositions suitable for stabilizing the extracellular nucleic acid population in a cell-containing sample, in particular a blood sample, and to a method for isolating extracellular nucleic acids from respectively stabilized biological samples.

BACKGROUND

Extracellular nucleic acids have been identified in blood, plasma, serum and other body fluids. Extracellular nucleic acids that are found in respective samples are to a certain extent degradation resistant due to the fact that they are protected from nucleases (e.g. because they are secreted in form of a proteolipid complex, are associated with proteins or are contained in vesicles). The presence of elevated levels of extracellular nucleic acids such as DNA and/or RNA in many medical conditions, malignancies, and infectious processes is of interest inter alia for screening, diagnosis, prognosis, surveillance for disease progression, for identifying potential therapeutic targets, and for monitoring treatment response. Additionally, elevated fetal DNA/RNA in maternal blood is being used to determine e.g. gender identity, assess chromosomal abnormalities, and monitor pregnancy-associated complications. Thus, extracellular nucleic acids are in particular useful in non-invasive diagnosis and prognosis and can be used e.g. as diagnostic markers in many fields of application, such as non-invasive prenatal genetic testing, oncology, transplantation medicine or many other diseases and, hence, are of diagnostic relevance (e.g. fetal- or tumor-derived nucleic acids). However, extracellular nucleic acids are also found in healthy human beings. Common applications and analysis methods of extracellular nucleic acids are e.g. described in WO97/035589, WO97/34015, Swarup et al, FEBS Letters 581 (2007) 795-799, Fleischhacker Ann. N.Y. Acad. Sci. 1075: 40-49 (2006), Fleischhacker and Schmidt, Biochmica et Biophysica Acta 1775 (2007) 191-232, Hromadnikova et al (2006) DNA and Cell biology, Volume 25, Number 11 pp 635-640; Fan et al (2010) Clinical Chemistry 56:8.

Traditionally, the first step of isolating extracellular nucleic acids from a cell-containing biological sample such as blood is to obtain an essentially cell-free fraction of said sample, e.g. either serum or plasma in the case of blood. The extracellular nucleic acids are then isolated from said cell-free fraction, commonly plasma, when processing a blood sample. However, obtaining an essentially cell-free fraction of a sample can be problematic and the separation is frequently a tedious and time consuming multi-step process as it is important to use carefully controlled conditions to prevent cell breakage during centrifugation which could contaminate the extracellular nucleic acids with cellular nucleic acids released during breakage. Furthermore, it is often difficult to remove all cells. Thus, many processed samples that are often and commonly classified as "cell-free" such as plasma or serum in fact still contain residual amounts of cells that were not removed during the separation process. Another important consideration is that cellular nucleic acid are released from the cells contained in the sample due to cell breakage during ex vivo incubation, typically within a relatively short period of time from a blood draw event. Once cell lysis begins, the lysed cells release additional nucleic acids which become mixed with the extracellular nucleic acids and it becomes increasingly difficult to recover the extracellular nucleic acids for testing. These problems are discussed in the prior art (see e.g. Chiu et al (2001), Clinical Chemistry 47:9 1607-1613; Fan et al (2010) and US2010/0184069). Further, the amount and recoverability of available extracellular nucleic acids can decrease substantially over a period of time due to degradation.

Besides mammalian extracellular nucleic acids that derive e.g. from tumor cells or the fetus, cell-containing samples may also comprise other nucleic acids of interest that are not comprised in cells. An important, non-limiting example is pathogen nucleic acids such as viral nucleic acids. Preservation of the integrity of viral nucleic acids in cell-containing samples such as in particular in blood specimens during shipping and handling is also crucial for the subsequent analysis and viral load monitoring.

The above discussed problems particularly are an issue, if the sample comprises a high amount of cells as is the case e.g. with whole blood samples. Thus, in order to avoid respectively reduce the above described problems it is common to separate an essentially cell-free fraction of the sample from the cells contained in the sample basically immediately after the sample is obtained. E.g. it is recommended to obtain blood plasma from whole blood basically directly after the blood is drawn and/or to cool the whole blood and/or the obtained plasma or serum in order to preserve the integrity of the extracellular nucleic acids and to avoid contaminations of the extracellular nucleic acid population with intracellular nucleic acids that are released from the contained cells. However, the need to directly separate e.g. the plasma from the blood is a major disadvantage because many facilities wherein the blood is drawn (e.g. a doctor's practice) do not have a centrifuge that would enable the efficient separation of blood plasma. Furthermore, plasma that is obtained under regular conditions often comprises residual amounts of cells which accordingly, may also become damaged or may die during handling of the sample, thereby releasing intracellular nucleic acids, in particular genomic DNA, as is described above. These remaining cells also pose a risk that they become damaged during the handling so that their nucleic acid content, particularly genomic (nuclear) DNA and cytoplasmic RNA, would merge with and thereby contaminate respectively dilute the extracellular, circulating nucleic acid fraction. To remove these remaining contaminating cells and to avoid/reduce the aforementioned problems, it was known to perform a second centrifugation step at higher speed. However, again, such powerful centrifuges are often not available at the facilities wherein the blood is obtained. Furthermore, even if plasma is obtained directly after the blood is drawn, it is recommended to freeze it at −80° C. in order to preserve the nucleic acids contained therein if the nucleic acids can not be directly isolated. This too imposes practical constraints upon the processing of the samples as e.g. the plasma samples must be shipped frozen. This increases the costs and furthermore, poses a risk that the sample gets compromised in case the cold chain is interrupted.

Blood samples are presently usually collected in blood collection tubes containing spray-dried or liquid EDTA (e.g. BD Vacutainer $K_2$EDTA). EDTA chelates magnesium, calcium and other bivalent metal ions, thereby inhibiting enzymatic reactions, such as e.g. blood clotting or DNA degradation due to DNases. However, even though EDTA is an efficient anticoagulant, EDTA does not efficiently prevent the dilution respectively contamination of the extracellular nucleic acid population by released intracellular nucleic acids. Thus, the extracellular nucleic acid population that is found in the cell-free portion of the sample changes during the storage. Accordingly, EDTA is not capable of sufficiently stabilising the extracellular nucleic acid population in particular because it can not avoid the contamination of the extracellular nucleic acid population with e.g. genomic DNA fragments which are generated after blood draw by cell degradation and cell instability during sample transportation and storage.

Methods are known in the prior art that specifically aim at stabilizing circulating nucleic acids contained in whole blood. One method employs the use of formaldehyde to stabilize the cell membranes, thereby reducing the cell lysis and furthermore, formaldehyde inhibits nucleases. Respective methods are e.g. described in U.S. Pat. Nos. 7,332,277 and 7,442,506. However, the use of formaldehyde or formaldehyde-releasing substances has drawbacks, as they may compromise the efficacy of extracellular nucleic acid isolation by induction of crosslinks between nucleic acid molecules or between proteins and nucleic acids. Alternative methods to stabilize blood samples are described e.g. in US 2010/0184069 and US 2010/0209930. These rather recently developed methods demonstrate the great need for providing means to stabilise cell-containing biological samples, to allow the efficient recovery of e.g. extracellular nucleic acids contained in such samples.

However, despite these rather recent developments there is still a continuous need to develop sample processing techniques which result in a stabilisation of the extracellular nucleic acid population comprised in a biological sample, in particular a sample containing cells, including samples suspected of containing cells, in particular whole blood, plasma or serum, thereby making the handling, respectively processing of such samples easier (e.g. by avoiding the need to directly separate plasma from whole blood or to cool or even freeze the isolated plasma) thereby also making the isolation and testing of extracellular nucleic acids contained in such samples more reliable and consequently, thereby improving the diagnostic and prognostic capabilities of the extracellular nucleic acids. In particular, there is a continuous need for a solution for preserving extracellular nucleic acids in whole blood samples, e.g. for prenatal testing and/or for screening for neoplastic, in particular premalignant or malignant diseases.

It is the object of the present invention to overcome at least one of the drawbacks of the prior art sample stabilization methods. Thus, it is inter alia an object of the present invention to provide a method that is capable of stabilising a cell-containing sample, in particular whole blood. In particular, it is an object of the present invention to stabilise the extracellular nucleic acid population contained in a biological sample and in particular to avoid a contamination of the extracellular nucleic acid population with genomic DNA, in particular fragmented genomic DNA. Furthermore, it is in particular an object of the present invention to provide a method tsuitable for stabilising a biological sample, preferably a whole blood sample, even at room temperature, preferably for a period of at least two, preferably at least three days. Furthermore, it is an object of the present invention to provide a sample collection container, in particular a blood collection tube that is capable of effectively stabilising a biological sample and in particular the extracellular nucleic acid population comprised in the sample.

SUMMARY OF THE INVENTION

The present invention is based on the finding that certain additives are surprisingly effective in stabilizing cell-containing biological samples comprising extracellular nucleic acids, in particular whole blood samples or samples derived from whole blood such as e.g. blood plasma. It was found that these additives are highly efficient in stabilizing the extracellular nucleic acid population and in particular are capable to avoid or at least significantly reduce contaminations with genomic DNA, in particular fragmented genomic DNA.

According to a first aspect, a method suitable for stabilizing an extracellular nucleic acid population comprised in a cell-containing sample is provided, wherein a sample is contacted with
   a) at least one apoptosis inhibitor,
   b) at least one hypertonic agent, which stabilizes the cells comprised in the sample, and/or
   c) at least one compound according to formula 1

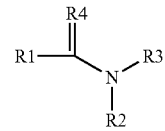

formula 1 wherein R1 is a hydrogen residue or an alkyl residue, preferably a C1-C5 alkyl residue, more preferred a methyl residue, R2 and R3 are identical or different hydrocarbon residues with a length of the carbon chain of 1-20 atoms arranged in a linear or branched manner, and R4 is an oxygen, sulphur or selenium residue.

According to a first sub-aspect, a method suitable for stabilizing an extracellular nucleic acid population comprised in a cell-containing sample is provided, wherein the sample is contacted with at least one apoptosis inhibitor. Preferably, the cell-containing sample is selected from whole blood, plasma or serum. Surprisingly, it was found that the apoptosis inhibitor reduces contaminations of the extracellular nucleic acid population with intracellular nucleic acids, in particular fragmented genomic DNA, that originate from cells contained in the sample, e.g. from damaged or dying cells. Furthermore, the inventors found that the apoptosis inhibitor reduces the degradation of nucleic acids present in the sample. Thus, the stabilization according to the present invention using an apoptosis inhibitor has the effect that the extracellular nucleic acid population contained in the sample is substantially preserved in the state it had shown at the time the biological sample was obtained, respectively collected.

According to a second sub-aspect, a method suitable for stabilizing an extracellular nucleic acid population comprised in a cell-containing sample is provided, wherein a sample is contacted with at least one hypertonic agent, which is capable of stabilizing cells comprised in the sample. It was surprisingly found that cell shrinking that is induced by mild hypertonic effects (osmosis) results in a considerable increase of the cell stability. By increasing the cell stability, the hypertonic agent in particular reduces the release of intracellular nucleic acids, in particular genomic DNA, from the contained cells into the extracellular portion or compartment of the sample. Thus, the stabilization according to the present invention using a hypertonic agent has the effect that the extracellular nucleic acid population contained in the sample is substantially preserved in the state it had shown at the time the biological sample was obtained, respectively collected.

According to a third sub-aspect of the present invention, a method suitable for stabilizing an extracellular nucleic acid population comprised in a cell-containing sample is provided, wherein a sample is contacted with at least one compound according to formula 1

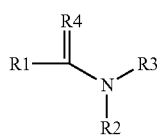

formula 1 wherein R1 is a hydrogen residue or an alkyl residue, preferably a C1-C5 alkyl residue, more preferred a methyl residue, R2 and R3 are identical or different hydrocarbon residues with a length of the carbon chain of 1-20 atoms arranged in a linear or branched manner, and R4 is an oxygen, sulphur or selenium residue. It was found that adding a respective compound as an advantageous stabilizing effect on the extracellular nucleic acid population.

According to a fourth sub-aspect, a method suitable for stabilizing an extracellular nucleic acid population comprised in a cell-containing sample is provided, wherein a sample is contacted with
  a) at least one apoptosis inhibitor, and
  b) at least one hypertonic agent, which stabilizes the cells comprised in the sample.

It was found that the combination of these stabilizing agents (and optionally further additives) is remarkably effective in inhibiting the release of intracellular nucleic acids, in particular genomic DNA, from the contained cells into the extracellular portion of the sample. Furthermore, it was shown that the degradation of nucleic acids present in the sample is highly efficiently prevented. In particular, less fragmented genomic DNA is found in respectively stabilized samples. Thus, the stabilization according to the present invention using this combination of stabilizing additives has the effect that the extracellular nucleic acid population contained in the sample is substantially and effectively preserved in the state it had shown at the time the biological sample was obtained, respectively collected (e.g. drawn in the case of blood) and that in particular contaminations of the extracellular nucleic acid population with fragmented genomic DNA are reduced.

In order to enhance the stabilization effect towards extracellular nucleic acids, it is also an object of the present invention to provide further combinations of stabilizing agents in order to stabilize the extracellular nucleic acid population comprised in a cell-containing sample. A respective combination may comprise at least one apoptosis inhibitor, at least one hypertonic agent and/or at least one compound according to formula 1 as defined above, for example (1) a combination of at least one apoptosis inhibitor and at least one compound according to formula 1 as defined above, (2) a combination of at least one hypertonic agent and at least one compound according to formula 1 or (3) a combination of all three stabilizing agents, i.e. at least one apoptosis inhibitor, at least one hypertonic agent and at least one compound according to formula 1. A respective combination may also comprise additional additives that enhance the stabilizing effect such as e.g. chelating agents. In case the sample is blood or a sample derived from blood, usually an anticoagulant is also added. Chelating agents such as e.g. EDTA are suitable for this purpose. Respective stabilizing combinations can be according to a fifth sub-aspect advantageously used in a method suitable for stabilizing an extracellular nucleic acid population comprised in a cell-containing sample according to the first aspect of the present invention.

According to a second aspect, a method for isolating extracellular nucleic acids from a biological sample is provided, wherein said method comprises the steps of:
  a) stabilizing the extracellular nucleic acid population comprised in a sample according to the method defined in the first aspect of the present invention; and
  b) isolating extracellular nucleic acids from said sample.

Stabilization in step a) can be achieved e.g. according to one of the five sub-aspects of the first aspect according to the present invention as described above. As discussed above, the stabilization according to the present invention has the effect that the extracellular nucleic acid population contained in the sample is substantially preserved in the state it had shown at the time the biological sample was obtained, respectively collected. Therefore, extracellular nucleic acids obtained from a respectively stabilized sample comprise less contaminations with intracellular nucleic acids, in particular fragmented genomic DNA, that results e.g. from decaying cells comprised in the sample compared to extracellular nucleic acids that are obtained from an unstabilized sample. The substantial preservation of the extracellular nucleic acid population is an important advantage because this stabilization/preservation enhances the accuracy of any subsequent tests. It allows for standardizing the isolation and subsequent analysis of the extracellular nucleic acid population, thereby making diagnostic or prognostic applications that are based on the extracellular nucleic acid fraction more reliable and more independent from the used storage/handling conditions. Thereby, the diagnostic and prognostic applicability of the respectively isolated extracellular nucleic acids is improved. In particular, the teachings of the present invention have the advantage that the ratio of certain extracellular nucleic acid molecules can be kept substantially constant compared to the ratio at the time the sample was collected. The stabilization achieves that intracellular nucleic acids are substantially kept within the cells and that extracellular nucleic acids are substantially stabilized.

According to a third aspect, a composition suitable for stabilizing a cell-containing biological sample is provided, comprising:
  a) at least one apoptosis inhibitor, preferably a caspase inhibitor, and/or
  b) at least one hypertonic agent which is suitable for stabilizing the cells comprised in the sample, preferably a hydroxylated organic compound; and/or c) at least one compound according to formula 1 as defined above; and/or
d) optionally at least one anticoagulant, preferably a chelating agent.

A respective stabilizing composition is particularly effective in stabilizing a cell-containing biological sample, in particular whole blood, plasma and/or serum by stabilizing the cells and the extracellular nucleic acid population comprised in said sample. Preferably, at least two of the stabilizing agents defined in a) to c) more preferred all of the stabilizing agents defined in a) to c) are present in the stabilizing composition. A respective stabilizing composition allows the storage and/or handling, e.g. shipping, of the sample, e.g. whole blood, at room temperature for at least two, or preferably at least three days without substantially compromising the quality of the sample, respectively the extracellular nucleic acid population contained therein. Thus, when using the stabilization composition according to the present invention, the time between sample collection, e.g. blood collection, and nucleic acid extraction can vary without substantial effect on the extracellular nucleic acid population contained in the sample. This is an important advantage as it reduces the variability in the extracellular nucleic acid population attributable to different handling procedures.

According to a forth aspect, a container for collecting a cell-containing biological sample, preferably a blood sample, is provided wherein the container comprises a composition according to the third aspect of the present invention. Providing a respective container, e.g. a sample collection tube comprising the stabilizing composition has the advantage that the sample is immediately stabilized as soon as the sample is collected in the respective container. Furthermore, a respective sample collection container, in particular a blood collection tube, is capable of stabilising blood cells and extracellular nucleic acids and optionally, viruses respectively viral nucleic acids contained in a blood sample or a sample derived from blood. Thereby, a further problem was overcome.

According to a fifth aspect, a method is provided comprising the step of collecting, preferably withdrawing, a biological sample, preferably blood, from a patient directly into a chamber of a container according to the fourth aspect of the present invention.

According to a sixth aspect, a method of producing a composition according to the third aspect of the present invention is provided, wherein the components of the composition are mixed, preferably are mixed in a solution. The term "solution" as used herein in particular refers to a liquid composition, preferably an aqueous composition. It may be a homogenous mixture of only one phase but it is also within the scope of the present invention that a solution comprises solid components such as e.g. precipitates.

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only. Various changes and modifications within the spirit and scope of the disclosed invention will become readily apparent to those skilled in the art from reading the following.

DETAILED DESCRIPTION OF THIS INVENTION

Figure 1A:
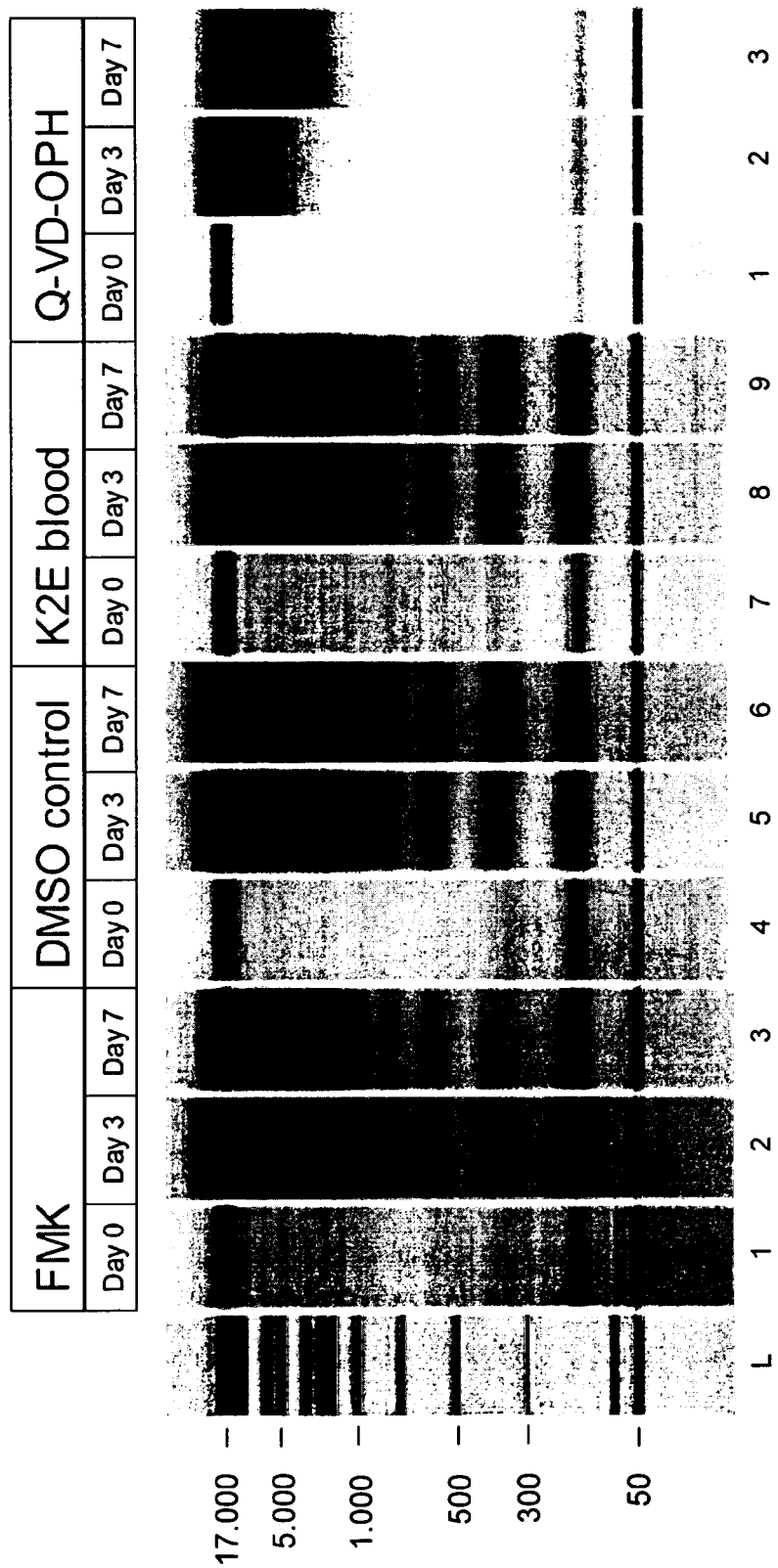
FIG. 1a shows a gel picture after chip electrophoresis of DNA isolated from samples treated with caspase inhibitors (Example 1).

The present invention is directed to methods, compositions and devices and thus to technologies suitable for stabilizing the extracellular nucleic acid population comprised in a cell-containing biological sample. The stabilization technologies disclosed herein reduce the risk that the extracellular nucleic acid population is contaminated with intracellular nucleic acids, in particular fragmented genomic DNA, which derives from, e.g. is released from damaged and/or dying cells contained in the sample. Therefore, the present invention achieves the stabilization of the sample and hence the stabilization of the extracellular nucleic acid population comprised therein without the lysis of the contained cells. Rather, cells contained in the sample are stabilized thereby substantially preventing or reducing the release of intracellular nucleic acids. The remarkable stabilization that is achieved with the methods and compositions of the present invention allows the storage and/or handling of the stabilized sample for a prolonged period of time at room temperature without jeopardizing the quality of the sample, respectively the extracellular nucleic acids contained therein. As the composition of the extracellular nucleic acid population is stabilized and thus substantially preserved at the time the sample is obtained by using the teachings of the present invention, the time between sample collection and nucleic acid extraction can vary without significant effect on the composition of the extracellular nucleic acids population. This allows the standardization of e.g. diagnostic or prognostic extracellular nucleic acid analysis because variations in the handling/storage of the samples have less influence on the quality, respectively the composition of the extracellular nucleic acid population, thereby providing an important advantage over prior art methods. Hence, the samples, respectively the extracellular nucleic acids obtained from respectively stabilized samples become more comparable. Furthermore, the teachings of the present invention obviate the necessity to directly separate cells contained in the sample from the cell-free portion of the sample in order to avoid, respectively reduce contaminations of the extracellular nucleic acids with intracellular nucleic acids, in particular fragmented genomic DNA, that is otherwise released from decaying cells. This advantage considerably simplifies the handling of the samples, in particular the handling of whole blood samples. E.g. whole blood samples obtained in a clinic and stabilized according to the teachings of the present invention can be shipped at room temperature and the plasma containing the extracellular nucleic acids can be conveniently separated in the receiving clinical lab. However, the teachings of the invention are also advantageous when processing cell-depleted biological samples, or samples commonly referred to as "cell-free" such as e.g. blood plasma or serum. Respective cell-depleted or "cell-free" biological samples may still (also depending on the used separation process) comprise residual cells, in particular white blood cells which comprise genomic DNA, which accordingly, pose a risk that the extracellular nucleic acid population becomes increasingly contaminated with intracellular nucleic acids, in particular fragmented genomic DNA, if the (potentially) remaining cells are damaged or die during the shipping of storing process. This risk is considerably reduced when using the stabilization method taught by the present invention. Because the technology of the present invention allows to efficiently preserve the extracellular nucleic acid population of the sample at the time the sample is collected and contacted with the stabilizing agents, said samples can be properly worked up in the receiving facilities in order to isolate the extracellular nucleic acids from said samples while substantially avoiding respectively reducing contaminations of the extracellular nucleic population with intracellular nucleic acids. The facilities receiving the samples such as e.g. laboratories usually also have the necessary equipment such as e.g. high speed centrifuges (or other means, see also below) to efficiently remove cells comprised in the samples, including residual cells that might be present in cell-depleted samples such as e.g. in blood plasma. Such equipment is often not present in the facilities where the sample is obtained. Thus, the present invention has many advantages when stabilizing biological samples which comprise a large amount of cells such as e.g. whole blood samples, but also has important advantages when stabilizing biological samples which comprise only a small amount of cells or which may only be suspected of containing cells such as e.g. plasma, serum, urine, saliva, synovial fluids, amniotic fluid, lachrymal fluid, ichors, lymphatic fluid, liquor, cerebrospinal fluid and the like.

According to a first aspect, a method suitable for stabilizing the extracellular nucleic acid population comprised in a cell-containing sample, preferably a blood sample, is provided, by contacting the sample with a) at least one apoptosis inhibitor, and/or
b) at least one hypertonic agent, which stabilizes the cells comprised in the sample, and/or
c) at least one compound according to formula 1

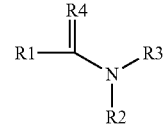

formula 1 wherein R1 is a hydrogen residue or an alkyl residue, preferably a C1-C5 alkyl residue, more preferred a methyl residue, R2 and R3 are identical or different hydrocarbon residues with a length of the carbon chain of 1-20 atoms arranged in a linear or branched manner, and R4 is an oxygen, sulphur or selenium residue.

Thereby, the risk is reduced that the extracellular nucleic acid population is contaminated with intracellular nucleic acids, in particular fragmented genomic DNA originating from contained cells, e.g. from damaged or dying cells and/or the degradation of nucleic acids present in the sample is reduced, respectively inhibited. This has the effect that the composition of the extracellular nucleic acid population comprised in said sample is substantially preserved, respectively stabilized.

The term "extracellular nucleic acids" or "extracellular nucleic acid" as used herein, in particular refers to nucleic acids that are not contained in cells. Respective extracellular nucleic acids are also often referred to as cell-free nucleic acids. These terms are used as synonyms herein. Hence, extracellular nucleic acids usually are present exterior of a cell or exterior of a plurality of cells within a sample. The term "extracellular nucleic acids" refers e.g. to extracellular RNA as well as to extracellular DNA. Examples of typical extracellular nucleic acids that are found in the cell-free fraction (respectively portion) of biological samples such as body fluids such as e.g. blood plasma include but are not limited to mammalian extracellular nucleic acids such as e.g. extracellular tumor-associated or tumor-derived DNA and/or RNA, other extracellular disease-related DNA and/or RNA, epigenetically modified DNA, fetal DNA and/or RNA, small interfering RNA such as e.g. miRNA and siRNA, and non-mammalian extracellular nucleic acids such as e.g. viral nucleic acids, pathogen nucleic acids released into the extracellular nucleic acid population e.g. from prokaryotes (e.g. bacteria), viruses, eukaryotic parasites or fungi. According to one embodiment, the extracellular nucleic acid is obtained from respectively is comprised in a body fluid as cell-containing biological sample such as e.g. blood, plasma, serum, saliva, urine, liquor, cerebrospinal fluid, sputum, lachrymal fluid, sweat, amniotic or lymphatic fluid. Herein, we refer to extracellular nucleic acids that are obtained from circulating body fluids as circulating extracellular or circulating cell-free nucleic acids. According to one embodiment, the term extracellular nucleic acid in particular refers to mammalian extracellular nucleic acids, preferably disease-associated or disease-derived extracellular nucleic acids such as tumor-associated or tumor-derived extracellular nucleic acids, extracellular nucleic acids released due to inflammations or injuries, in particular traumata, extracellular nucleic acids related to and/or released due to other diseases, or extracellular nucleic acids derived from a fetus. The term "extracellular nucleic acids" or "extracellular nucleic acid" as described herein also refers to extracellular nucleic acids obtained from other samples, in particular biological samples other than body fluids. Usually, more than one extracellular nucleic acid is comprised in a sample. Usually, a sample comprises more than one kind or type of extracellular nucleic acids. The term "extracellular nucleic acid population" as used herein in particular refers to the collective of different extracellular nucleic acids that are comprised in a cell-containing sample. A cell-containing sample usually comprises a characteristic and thus unique extracellular nucleic acid population. Thus, the type, kind and/or the amount of one or more extracellular nucleic acids comprised in the extracellular nucleic acid population of a specific sample are important sample characteristics. As discussed above, it is therefore important to stabilize and thus to substantially preserve said extracellular nucleic acid population as its composition and/or the amount of one or more extracellular nucleic acids comprised in the extracellular nucleic acid population of a sample, can provide valuable information in the medical, prognostic or diagnostic field. In particular, it is important to reduce the contamination and hence dilution of the extracellular nucleic acid population by intracellular nucleic acids, in particular by genomic DNA, after the sample was collected. The substantial preservation of the extracellular nucleic acid population that can be achieved with the stabilization technologies according to the invention allows the population of extracellular nucleic acids within a sample to be maintained substantially unchanged over the stabilization period as compared to the population of extracellular nucleic acids at the moment of sample stabilization. At least, changes in the extracellular nucleic acid population with respect to the quantity, the quality and/or the composition of the comprised extracellular nucleic acids, in particular changes attributable to an increase of released genomic DNA, are over the stabilization period considerably reduced (preferably by at least 60%, at least 70%, at least 75%, at least 80%, at least 85%, at least 90% or at least 95%) compared to an unstabilized sample or a corresponding sample that is e.g. stabilized by EDTA in case of a blood sample or a sample derived from blood.

According to a first sub-aspect of the first aspect, at least one apoptosis inhibitor is used for stabilizing the sample. As is shown by the provided examples, already the apoptosis inhibitor alone is effective in stabilizing a cell-containing sample and to substantially preserve the extracellular nucleic acid population from changes in its composition in particular arising from contaminations with fragmented genomic DNA. The sample can be contacted with the apoptosis inhibitor, e.g. by adding the apoptosis inhibitor to the sample or vice versa. The at least one apoptosis inhibitor present in the resulting mixture supports the stabilization of cells contained in the sample and inhibits the degradation of nucleic acids comprised in the sample thereby substantially preserving the extracellular nucleic acid population.

The term "apoptosis inhibitor" as used herein in particular refers to a compound whose presence in a cell-containing biological sample provides a reduction, prevention and/or inhibition of apoptotic processes in the cells and/or makes the cells more resistant to apoptotic stimuli. Apoptosis inhibitors include but are not limited to proteins, peptides or protein- or peptide-like molecules, organic and inorganic molecules. Apoptosis inhibitors include compounds that act as metabolic inhibitors, inhibitors of nucleic acid degradation respectively nucleic acid pathways, enzyme inhibitors, in particular caspase inhibitors, calpain inhibitors and inhibitors of other enzymes involved in apoptotic processes. Respective apoptosis inhibitors are listed in Table 1. Preferably, the at least one apoptosis inhibitor that is used for stabilizing the cell-containing biological sample is selected from the group consisting of metabolic inhibitors, caspase inhibitors and calpain inhibitors. Suitable examples for each class are listed in Table 1 in the respective category. Preferably, the apoptosis inhibitor is cell-permeable.

It is also within the scope of the present invention to use a combination of different apoptosis inhibitors, either from the same or a different class of apoptosis inhibitors, respectively to use a combination of different apoptosis inhibitors which inhibit apoptosis either by the same or a different working mechanism.

In an advantageous embodiment of the present invention, the apoptosis inhibitor is a caspase inhibitor. Members of the caspase gene family play a significant role in apoptosis. The substrate preferences or specificities of individual caspases have been exploited for the development of peptides that successfully compete caspase binding. It is possible to generate reversible or irreversible inhibitors of caspase activation by coupling caspase-specific peptides to e.g. aldehyde, nitrile or ketone compounds. E.g. fluoromethyl ketone (FMK) derivatized peptides such as Z-VAD-FMK act as effective irreversible inhibitors with no added cytotoxic effects. Inhibitors synthesized with a benzyloxycarbonyl group (BOC) at the N-terminus and O-methyl side chains exhibit enhanced cellular permeability. Further suitable caspase inhibitors are synthesized with a phenoxy group at the C-terminus. An example is Q-VD-OPh which is a cell permeable, irreversible broad-spectrum caspase inhibitor that is even more effective in preventing apoptosis than Z-VAD-FMK.

According to one embodiment, the caspase inhibitor is a pancaspase inhibitor and thus is a broad spectrum caspase inhibitor. According to one embodiment, the caspase inhibitor comprises a modified caspase-specific peptide. Preferably, said caspase-specific peptide is modified by an aldehyde, nitrile or ketone compound. According to a preferred embodiment, the caspase specific peptide is modified preferably at the carboxyl terminus with an O-Phenoxy or a fluoromethyl ketone (FMK) group. According to one embodiment, the caspase inhibitor is selected from the group consisting of Q-VD-OPh and Z-VAD(OMe)-FMK. In one embodiment, Z-VAD(OMe)-FMK, a pancaspase inhibitor, is used, which is a competitive irreversible peptide inhibitor and blocks caspase-1 family and caspase-3 family enzymes. In a preferred embodiment, Q-VD-OPh, which is a broad spectrum inhibitor for caspases, is used. Q-VD-OPh is cell permeable and inhibits cell death by apoptosis. Q-VD-OPh is not toxic to cells even at extremely high concentrations and consists of a carboxy terminal phenoxy group conjugated to the amino acids valine and aspartate. It is equally effective in preventing apoptosis mediated by the three major apoptotic pathways, caspase-9 and caspase-3, caspase-8 and caspase-10, and caspase-12 (Caserta et al, 2003). Further caspase inhibitors are listed in Table 1. According to one embodiment, the caspase inhibitor that is used as apoptosis inhibitor for stabilizing the cell-containing sample is one which acts upon one or more caspases located downstream in the intracellular cell death pathway of the cell, such as caspase-3. In one embodiment of the present invention the caspase inhibitor is an inhibitor for one or more caspases selected from the group consisting of caspase-3, caspase-8, caspase-9, caspase-10 and caspase-12. It is also within the scope of the present invention to use a combination of caspase inhibitors.

The mixture that is obtained after contacting the biological sample with the at least one apoptosis inhibitor may comprise the apoptosis inhibitor (or combination of apoptosis inhibitors) in a concentration selected from the group of at least 0.01 μM, at least 0.05 μM, at least 0.1 μM, at least 0.5 μM, at least 1 μM, at least 2.5 μM or at least 3.5 μM. Of course, also higher concentrations can be used. Suitable concentration ranges for the apoptosis inhibitor(s) when mixed with the cell-containing biological sample, include but are not limited to 0.01 μM to 100 μM, 0.05 μM to 100 μM, 0.1 μM to 50 μM, 0.5 μM to 50 μM, 1 μM to 40 μM, more preferably 1 μM to 30 μM or 2.5 μM to 25 μM. The higher concentrations were found to be more effective, however, good stabilizing results were also achieved at lower concentrations. Hence, an efficient stabilization is also achieved at lower concentrations e.g. in a range selected from 0.1 μM to 10 μM, 0.5 μM to 7.5 μM or 1 μM to 5 μM, in particular if the apoptosis inhibitor is used in combination with a hypertonic agent (see below). The above mentioned concentrations apply to the use of a single apoptosis inhibitor as well as to the use of a combination of caspase inhibitors. If a combination of caspase inhibitors is used, the concentration of an individual apoptosis inhibitor that is used in said mixture of apoptosis inhibitors may also lie below the above mentioned concentrations, if the overall concentration of the combination of apoptosis inhibitors fulfils the above mentioned features. Using a lower concentration that still efficiently stabilizes the cells and/or reduce the degradation of nucleic acids in present in the sample has the advantage that the costs for stabilisation can be lowered. Lower concentrations can be used e.g. if the apoptosis inhibitor is used in combination with one or more stabilizers as described herein. The aforementioned concentrations are in particular suitable when using a caspase inhibitor, in particular a modified caspase specific peptide such as Q-VD-OPh and/or Z-VAD(OMe)-FMK as apoptosis inhibitor. The above mentioned concentrations are e.g. very suitable for stabilizing whole blood, in particular 10 ml blood. Suitable concentration ranges for other apoptosis inhibitors and/or for other cell-containing biological samples can be determined by the skilled person using routine experiments, e.g. by testing the apoptosis inhibitors, respectively the different concentrations in the test assays described in the examples.

According to one embodiment, the apoptosis inhibitor will, in an effective amount, decrease or reduce apoptosis in a cell-containing biological sample by at least 25 percent, at least 30 percent, at least 40 percent, at least 50 percent, preferably, by at least 75 percent, more preferably, by at least 85 percent as compared to a control sample which does not contain a respective apoptosis inhibitor.

According to a second sub-aspect of the first aspect of the present invention, at least one hypertonic agent is used for stabilizing the sample, wherein the used hypertonic agent stabilizes cells comprised in the sample. As is shown by the provided examples, already the hypertonic agent alone is effective in stabilizing a cell-containing sample and substantially preserving the composition of the extracellular nucleic acid population comprised therein. The hypertonic agent induces cell shrinking by mild hypertonic effects (osmosis), thereby increasing the cell stability. Therefore, the cells are less prone to e.g. mechanically induced cell damage. The sample can be contacted with the hypertonic agent, e.g. by adding the hypertonic agent to the sample or vice versa. The hypertonic agent present in the resulting mixture in particular is suitable for stabilizing cells contained in the sample, thereby reducing the amount of intracellular nucleic acids, in particular genomic DNA that is released from damaged cells. Thereby, the extracellular nucleic acid population is substantially preserved and the risk of contaminating respectively diluting the extracellular nucleic acids with intracellular nucleic acids, in particular genomic DNA, is reduced.

According to one embodiment, the hypertonic agent is sufficiently osmotically active to induce cell shrinking (the cells release water), however, without damaging the cells i.e. without inducing or promoting cell lysis, respectively cell rupture. Hence, the hypertonic agent preferably has a mild osmotic effect. Furthermore, it is desirous that interactions between the hypertonic agent and the sample are predominantly limited to the cell stabilization effect basically in order to avoid unwanted side effects. Thus, according to one embodiment, an uncharged hypertonic agent is used. Using an uncharged hypertonic agent has the advantage that even though the cells shrink respectively are stabilized due to the osmotic effect of the hypertonic agent, interactions between the hypertonic agent and other compounds comprised in the sample are limited compared to the use of a charged hypertonic agent.

According to an advantageous embodiment, the hypertonic agent is a hydroxylated organic compound and accordingly, carries at least one hydroxyl group. According to one embodiment, the hydroxylated organic compound comprises at least two hydroxyl groups. According to one embodiment, the hydroxylated organic compound is a polyol. According to one embodiment, the polyol comprises 2 to 10 hydroxyl groups, preferably 3 to 8 hydroxyl groups. The hydroxylated organic compound may comprise 2 to 12 carbon atoms, preferably 3 to 8 and can be a cyclic or linear molecule, branched or un-branched; it can be saturated or unsaturated; aromatic or non-aromatic. According to one embodiment, the hydroxylated organic compound is a hydroxy-carbonyl compound. A hydroxy-carbonyl compound is a compound possessing one or more hydroxy (OH) groups and one or more carbonyl groups. Hydroxylated organic compounds may include but are not limited to hydroxylated ketone compounds and carbohydrates, or compounds derived therefrom. According to one embodiment, the hydroxylated organic compound is a polyalcohol, in particular a sugar alcohol. Hence, hydroxylated organic compounds include but are not limited to carbohydrates such as glucose, raffinose, succrose, fructose, alpha-d-lactose monohydrate, inositol, maltitol, mannitol, dihydroxyacetone, alcohols such as glycerol, erythritol, mannitol, sorbitol, volemitol, or sugar alcohols. Suitable examples are also listed in the table below. It is also within the scope of the present invention to use combinations of respective hydroxylated organic compounds.

| Chemical Formula | IUPAC Name | Common Name |
|---|---|---|
| Polyols, e.g. | | |
| $C_3H_5(OH)_3$ | Propane-1,2,3-triol | Glycerin |
| $C_4H_6(OH)_4$ | Butane-1,2,3,4-tetraol | Erythritol |
| $C_5H_7(OH)_5$ | Pentane-1,2,3,4,5-pentol | Xylitol, Arabitol, Ribitol |
| $C_6H_8(OH)_6$ | Hexane-1,2,3,4,5,6-hexol | Mannitol, Sorbitol, Dulcitol, Iditol |
| $C_7H_9(OH)_7$ | Heptane-1,2,3,4,5,6,7-heptol | Volemitol |
| Alicyclic and sugar alcohols, e.g. | | |
| $C_6H_6(OH)_6$ | Cyclohexane-1,2,3,4,5,6-geksol | Inositol |
| $C_{12}H_{24}O_{11}$ | 1-O-α-D-Glucopyranosyl-D-mannitol | Isomalt |
| $C_{12}H_{24}O_{11}$ | 4-O-α-D-Glucopyranosyl-D-glucitol | Maltitol |
| $C_{12}H_{24}O_{11}$ | 4-O-α-D-Galactopyranosyl-D-glucitol | Lactitol |

According to one embodiment, the polyols and sugar alcohols listed above may be replaced by alcohols with less hydroxyl groups (e.g., hexane-1,2,3,4,5-pentol, pentane-1,2,3,4-tetraol). According to one embodiment, the hydroxylated organic compound is no alcohol having 1 to carbon atoms and carrying only one hydroxyl group. According to one embodiment, alcohols with only one hydroxyl group are excluded as hydroxylated organic compound. The hydroxylated organic compound that can be used as stabilizer according to the present invention preferably is water-soluble and non-toxic to the cells comprised in the biological sample to be stabilized. Preferably, the hydroxylated organic compound does not induce or support the lysis of the cells contained in the biological sample and accordingly, preferably does not function as a detergent or as cell membrane dissolving agent. A suitable hydroxylated organic compound according to the present invention achieves a stabilizing effect of the cell-containing sample by improving the preservation of the composition of the extracellular nucleic acid population as can be e.g. tested by the assays described in the example section.

Adding a hydroxylated organic compound to a cell-containing biological sample such as e.g. whole blood, increases the concentration of said hydroxylated organic compound in the cell-free portion respectively fraction (e.g. the blood plasma) and thus forces blood cells to release water into the plasma as a result of an osmotic (hypertonic) effect. According to one embodiment, a hydroxylated organic compound is used which is closely related to a product of the cell metabolism but preferably can not be utilized by the cells.

According to a preferred embodiment, cells contained in the biological sample are essentially impermeable for the hypertonic agent that is used for stabilization. Thus, the hypertonic agent, which preferably is a hydroxylated organic compound as described in detail above, is essentially cell impermeable. Essentially cell impermeable in this respect in particular means that the concentration of the hypertonic agent, which preferably is a hydroxylated organic compound, is substantially higher in the extracellular portion of the sample than inside the cells contained in the biological sample that is stabilized according to the teachings of the present invention. According to a preferred embodiment, the hypertonic agent, which preferably is a hydroxylated organic compound, is non-toxic, so that the cell viability is not compromised. This is preferred to avoid disturbing influences on the cell metabolism.

According to one embodiment, the hypertonic agent is dihydroxyacetone (DHA). DHA is a carbohydrate and usually serves as tanning substance in self-tanning lotions. As is demonstrated by the examples, DHA surprisingly has a remarkable stabilizing effect on cell-containing biological samples, in particular whole blood samples and samples derived from whole blood such as blood plasma or serum. DHA does naturally not occur in mammalian cells except for the phosphoric acid ester of DHA, dihydroxyacetone-phosphat, an intermediate product of glycolysis. Thus DHA is not expected to be actively transported or to diffuse into blood cells. According to one embodiment, the hypertonic agent is not dihydroxyaceton-phosphate.

The mixture that is obtained when contacting the cell-containing biological sample with the at least one hypertonic agent may comprise the hypertonic agent or mixture of hypertonic agents in a concentration of at least 0.05M, preferably 0.1M, preferably at least 0.2M, more preferred at least 0.25M. Of course, also higher concentrations can be used. Suitable concentration ranges for the hypertonic agent can be selected from 0.05M to 2M, 0.1M to 1.5M, 0.15M to 0.8M, 0.2M to 0.7M or 0.1M to 0.6M. Respective concentrations are particularly suitable when using a hydroxylated organic compound, e.g. a carbohydrate such as dihydroxyacetone as hypertonic agent. The above mentioned concentrations are e.g. very suitable for stabilizing whole blood, in particular 10 ml blood. Suitable concentration ranges for other hypertonic agents and/or other cell-containing biological samples can also be determined by the skilled person using routine experiments, e.g. by testing the hypertonic agents, respectively different concentrations thereof in the test assays described in the examples.

According to a third sub-aspect of the first aspect of the present invention, for stabilizing the extracellular nucleic acid population in a cell containing sample, at least one compound according to formula 1 is used

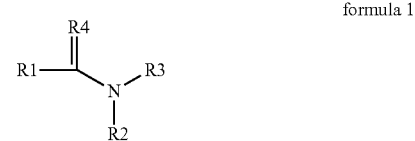

formula 1 wherein R1 is a hydrogen residue or an alkyl residue, preferably a C1-C5 alkyl residue, more preferred a methyl residue, R2 and R3 are identical or different hydrocarbon residues with a length of the carbon chain of 1-20 atoms arranged in a linear or branched manner, and R4 is an oxygen, sulphur or selenium residue.

As is shown by the provided examples, a compound according to formula 1 described above is effective in achieving a remarkable stabilizing effect and in substantially preserving the composition of the extracellular nucleic acid population in the stabilized sample. Also a mixture of one or more compounds according to formula 1 can be used for stabilization.

The hydrocarbon residues R2 and/or R3 can be selected independently of one another from the group comprising alkyl, including short chain alkyl and long-chain alkyl, alkenyl, alkoxy, long-chain alkoxy, cycloalkyl, aryl, haloalkyl, alkylsilyl, alkylsilyloxy, alkylene, alkenediyl, arylene, carboxylates and carbonyl. General groups, for instance alkyl, alkoxy, aryl etc. are claimed and described in the description and the claims. Preferably, the following groups are used within the generally described groups within the scope of the present invention:

(1) alkyl: preferably short chain alkyls, in particular linear and branched C1-C5 alkyls or long-chain alkyls: linear and branched C5-C20 alkyls;
(2) alkenyl: preferably C2-C6 alkenyl;
(3) cycloalkyl: preferably C3-C8 cycloalkyl;
(4) alkoxy: preferably C1-C6 alkoxy;
(5) long-chain alkoxy: preferably linear and branched C5-C20 alkoxy;
(6) alkylenes: preferably a divalent linear or branched aliphatic, cycloaliphatic or aromatic hydrocarbon residue with 2 to 18 carbon atoms optionally containing heteroatoms, e.g. selected from the group comprising: methylene; 1,1-ethylene; 1,1-propylidene; 1,2-propylene; 1,3-propylene; 2,2-propylidene; butan-2-ol-1,4-diyl; propan-2-ol-1,3-diyl; 1,4-butylene; 1,4-pentylene; 1,6-hexylene; 1,7-heptylene; 1,8-octylene; 1,9-nonylene; 1,10-decylene; 1,11-undecylene; 1,12-docedylene; cyclohexane-1,1-diyl; cyclohexane-1,2-diyl; cyclohexane-1,3-diyl; cyclohexane-1,4-diyl; cyclopentane-1,1-diyl; cyclopentane-1,2-diyl; and cyclopentane-1,3-diyl;
(7) alkenediyl: preferably selected from the group comprising: 1,2-propenediyl; 1,2-butenediyl; 2,3-butenediyl; 1,2-pentenediyl; 2,3-pentenediyl; 1,2-hexenediyl; 2,3-hexenediyl; and 3,4-hexenediyl;
(8) alkynediyl: is equal to —C≡C—;
(9) aryl: preferably selected from aromatics with a molecular weight below 300 Da;
(10) arylenes: preferably selected from the group comprising: 1,2-phenylene; 1,3-phenylene; 1,4-phenylene; 1,2-naphtthalenylene; 1,3-naphtthalenylene; 1,4-naphtthalenylene; 2,3-naphtthalenylene; 1-hydroxy-2,3-phenylene; 1-hydroxy-2,4-phenylene; 1-hydroxy-2,5-phenylene; 1-hydroxy-2,6-phenylene;
(11) carboxylate: preferably the group —C(O)OR, where R is selected from: hydrogen; C1-C6 alkyl; phenyl; C1-C6 alkyl-$C_6H_5$; Li; Na; K; Cs; Mg; Ca;
(12) carbonyl: preferably the group —C(O)R, where R is selected from: hydrogen; C1-C6 alkyl; phenyl; C1-C6 alkyl-C6H5 and amine (resulting in an amide) selected from the group: —NR'2, where each R' is selected independently from: hydrogen; C1-C6 alkyl; C1-C6 alkyl-C6H5 and phenyl, where, if both Rs represent C1-C6 alkyl they can form an NC3 to NC5 heterocyclic ring with alkyl substituents of the ring forming the other alkyl chain;
(13) alkylsilyl: preferably the group —SiR1R2R3, where R1, R2 and R3 are selected independently of one another from: hydrogen; alkyl; long-chain alkyl; phenyl; cycloalkyl; haloalkyl; alkoxy; long-chain alkoxy;
(14) alkylsilyloxy: preferably the group —O—SiR1R2R3, where R1, R2 and R3 are selected independently of one another from: hydrogen; alkyl; long-chain alkyl; phenyl; cycloalkyl; haloalkyl; alkoxy; long-chain alkoxy.

The chain length n of R2 and/or R3 can in particular have the values 1, 2, 3, 4, 5, 6, 7, 8, 9, 10, 11, 12, 13, 14, 15, 16, 17, 18, 19 and 20. Preferably R2 and R3 have a length of the carbon chain of 1-10. In this case the chain length n can in particular have the values 1, 2, 3, 4, 5, 6, 7, 8, 9, and 10. Preferably, R2 and R3 have a length of the carbon chain of 1-5 and in this case the chain length can in particular have the values 1, 2, 3, 4 and 5. Particularly preferred is a chain length of 1 or 2 for R2 and R3.

The chain length n of R1 preferably has the value 1, 2, 3, 4 or 5. Particularly preferred is a chain length of 1 or 2 for R1.

R4 preferably is oxygen.

According to a preferred embodiment, the compound according to formula 1 is a N,N-dialkyl-carboxylic acid amide. Preferred R1, R2, R3 and R4 groups are described above. According to one embodiment, the compound is selected from the group consisting of N,N-dimethylacetamide; N,N-diethylacetamide; N,N-dimethylformamide and N,N-diethylformamide. Also suitable are N,N-dialkylpropanamides such as N,N-dimethylpropanamide as is shown in the examples. Preferably, the substance according to formula 1 is N,N-dimethlyacetamide (DMAA). The structural formulae of the preferred compounds are as follows:

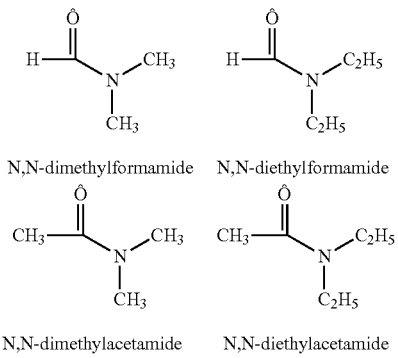

Also suitable are the respective thio analogues, which comprise sulphur instead of oxygen as R4.

The mixture that is obtained when contacting the cell-containing biological sample with a compound according to formula 1 or a mixture of respective compounds may comprise said compound or mixture of compounds in a final concentration of at least 0.1%, at least 0.5%, at least 0.75%, at least 1%, at least 1.25% or at least 1.5%. A suitable concentration range includes but is not limited to 0.1% up to 50%. Preferred concentration ranges can be selected from the group consisting of 0.1% to 30%, 0.1% to 20%, 0.1% to 15%, 0.1% to 10%, 0.1% to 7.5%, 0.1% to 5%, 1% to 30%, 1% to 20%, 1% to 15%, 1% to 10%, 1% to 7.5%, 1% to 5%; 1.25% to 30%, 1.25% to 20%, 1.25% to 15%, 1.25% to 10%, 1.25% to 7.5%, 1.25% to 5%; 1.5% to 30%, 1.5% to 20%, 1.5% to 15%, 1.5% to 10%, 1.5% to 7.5% and 1.5% to 5%. Respective concentrations are particularly suitable when using a N,N-dialkyl-carboxylic acid amide, e.g. N,N-dimethylacetamide, N,N-diethylacetamide, N,N-diethylformamide or N,N-diemethylformamide or N,N-dimethylpropanamide as stabilizing agent. The above mentioned concentrations are e.g. very suitable for stabilizing whole blood or blood products such as plasma. Suitable concentration ranges for other compounds according to formula 1 and/or other cell-containing biological samples can also be determined by the skilled person using routine experiments, e.g. by testing the compound, respectively different concentrations thereof in the test assays described in the examples.

Preferably, the compound according to formula 1 is used in combination with a chelating agent for stabilizing the cell containing sample. In particular, a chelating agent can be used as anticoagulant when stabilizing a blood sample or a sample derived from blood such as e.g. plasma or serum. Suitable chelating agents and concentration ranges are provided below.

According to a preferred fourth sub-aspect, a method suitable for stabilizing a cell-containing sample, preferably a blood sample is provided, wherein said method comprises contacting the sample with
   a) at least one apoptosis inhibitor, and
   b) at least one hypertonic agent, which stabilizes the cells comprised in the sample.

Thus, according to this preferred embodiment, the apoptosis inhibitor and the hypertonic agent, which both alone are already effective in stabilizing a cell-containing sample (see above and examples), are used in combination. Thereby, the stabilization effect can be increased and/or the concentration of the individual components (the apoptosis inhibitor and/or the hypertonic agent) may also be reduced while still efficiently preserving the extracellular nucleic acid population in the sample, and in particular avoiding, respectively reducing the contamination by intracellular nucleic acids in particular fragmented genomic DNA that is released from damaged or decaying cells contained in the sample. As is shown in the examples, using a respective combination is particularly effective in stabilizing a cell-containing sample, even very complex samples such as a whole blood sample. It is also within the scope of the present invention to use a mixture of different apoptosis inhibitors in combination with different hypertonic agents. Suitable and preferred embodiments of the apoptosis inhibitor and the hypertonic agent as well as suitable and preferred concentrations of the respective agents suitable for achieving an efficient stabilization of the sample are described in detail above in conjunction with the embodiments, wherein either an apoptosis inhibitor or a hypertonic agent is used to stabilize the cell-containing biological sample. It is referred to the above disclosure which also applies to the embodiment, wherein an apoptosis inhibitor is used in combination with a hypertonic agent. Preferably, at least one caspase inhibitor, preferably a modified caspase specific peptide, preferably modified at the C-terminus with an O-phenoxy group such as Q-VD-OPh, is used in combination with at least one hydroxylated organic compound, e.g. a carbohydrate, such as dihydroxyacetone or a polyol, as hypertonic agent. As is demonstrated by the examples, a respective combination is remarkably effective in stabilizing a cell-containing biological sample, in particular a whole blood sample, at room temperature for more than 3 days and even for 6 days.

According to one embodiment, a combination of stabilizing agents is used which comprises at least one apoptosis inhibitor, at least one hypertonic agent and/or at least one compound according to formula 1 as defined above. Examples of respective combinations include (1) a combination of at least one apoptosis inhibitor and at least one compound according to formula 1 as defined above, (2) a combination of at least one hypertonic agent and at least one compound according to formula 1 as defined above or (3) a combination of all three stabilizing agents, i.e. at least one apoptosis inhibitor, at least one hypertonic agent and at least one compound according to formula 1 as defined above. A respective combination may also comprise additional additives that enhance the stabilizing effect such as e.g. anticoagulants and chelating agents. According to one embodiment, the combination of stabilizing agents comprises a caspase inhibitor and an anticoagulant, preferably a chelating agent such as EDTA. Respective combinations can be according to a fifth sub-aspect advantageously used in a method suitable for stabilizing an extracellular nucleic acid population comprised in a cell-containing sample according to the first aspect of the present invention. The stabilizing effect observed with combinations of stabilizing agents is stronger than the effect observed for any of the individual stabilizing agents when used alone and/or allows to use lower concentrations, thereby making combinatorial use of stabilizing agents an attractive option. Suitable and preferred embodiments of the apoptosis inhibitor, the hypertonic agent and the compound according to formula 1 defines above as well as suitable and preferred concentrations of the respective agents suitable for achieving an efficient stabilization of the sample are described in detail above in conjunction with the embodiments, wherein either an apoptosis inhibitor, a hypertonic agent or a compound according to formula 1 is used to stabilize the cell-containing biological sample.

As discussed in the background of the invention, extracellular nucleic acids are usually not present "naked" in the sample but are e.g. stabilized to a certain extent by being released protected in complexes or by being contained in vesicles and the like. This has the effect that extracellular nucleic acids are already to a certain extent stabilized by nature and thus, are usually not degraded rapidly by nucleases in cell-containing samples such as whole blood, plasma or serum. Thus, when intending to stabilize extracellular nucleic acids that are comprised in a biological sample, one of the primary problems is the dilution, respectively the contamination of the extracellular nucleic acid population by intracellular nucleic acids, in particular fragmented genomic DNA, that originates from damaged or dying cells that are contained in the sample. This also poses a problem when processing cell-depleted samples such as plasma or serum (which are sometimes also describes as being "cell-free" even though they may comprise minor amounts of cells). The stabilization technology according to the present invention is of particular advantage in this respect because it not only substantially preserves the extracellular nucleic acids present in the sample and e.g. inhibits degradation of the comprised extracellular nucleic acids (preferably at least by 60%, at least by 70%, at least by 75%, at least by 80%, at least by 85%, at least by 90% or most preferably at least by 95% over the stabilization period compared to an unstabilized sample or an EDTA stabilized sample) but furthermore, efficiently reduces the release of genomic DNA from cells contained in the sample and/or reduces the fragmentation of respective genomic DNA. According to one embodiment, using the apoptosis inhibitor, the hypertonic agent and/or the compound according to formula 1 for stabilizing the cell-containing sample according to the teachings of the present invention has the effect that the increase of DNA that results from a release of DNA from cells contained in the sample is reduced compared to a non-stabilized sample. According to one embodiment, said release of genomic DNA is reduced by at least 3-fold, at least 4-fold, at least 5-fold, at least 6-fold, at least 7-fold, at least 10-fold, at least 12-fold, at least 15-fold, at least 17-fold or at least 20-fold over the stabilization period compared to the non-stabilized sample or a corresponding sample that is stabilized with EDTA (in particular in case of a blood sample or a sample derived from blood such as plasma or serum). According to one embodiment, said release of genomic DNA is reduced by at least 60%, at least 70%, at least 75%, at least 80%, at least 85%, at least 90% or at least 95% over the stabilization period compared to the non-stabilized sample or a corresponding sample that is stabilized with EDTA (in particular in case of a blood sample or a sample derived from blood such as plasma or serum). The release of DNA can be determined e.g. by quantifying the ribosomal 18S DNA as is described herein in the example section. E.g. standard EDTA stabilized blood samples show a 40-fold increase of DNA determined e.g. at day 6 of storage at room temperature in a respective assay (see FIG. 2b). The stabilization achievable with the teachings of the present invention remarkably reduces this release of DNA even down to e.g. a maximum of 4-fold. Thus, the extracellular nucleic acid population contained in the sample is considerably stabilized compared to samples stabilized in standard EDTA tubes. Thus, according to one embodiment, the stabilization effect that is achieved with the apoptosis inhibitor, the hypertonic agent and/or the compound according to formula 1 as taught by the present invention results in that the release of DNA from cells contained in the sample is at least reduced to a maximum of 10-fold, preferably 7-fold, more preferably 5-fold and most preferably is at least reduced to a maximum of 4-fold, as is e.g. determinable in the 18S DNA assay described in the examples. As is shown by the examples, an effective stabilization of the extracellular nucleic acid population is achievable for a period of at least up to 6 days. During a shorter storage of the samples, e.g. up to three days, the DNA release can be reduced at least to a maximum of two-fold as e.g. determinable in the 18S DNA assay described in the examples. Thus, the DNA release can be reduced to 2 fold or less up to three days of storage when using the stabilizing methods according to the present invention. This is a remarkable improvement in the stabilization of the extracellular nucleic acid population compared to the prior art methods. This significantly enhances the accuracy of any subsequent tests. In certain cases, for example if the sample material has to be transported for long distances or stored for longer periods e.g. at room temperature (as can be e.g. the case in certain countries), the process according to the invention makes it possible for the first time for these tests to be carried out after such a period of time. However, of course, the samples may also be further processed earlier, if desired. It is not necessary to make use of the full achievable stabilization period. The stabilization that is achieved with the present invention reduces variations in the extracellular nucleic acid population that may result from a different handling/processing of the samples (e.g. storage conditions and periods) after they were collected. This greatly improves the standardization of handling and molecular analysis.

Further additives may be used in addition to the apoptosis inhibitor, the hypertonic agent and/or the compound according to formula 1 as defined above in order to further stabilize the cell-containing sample. The selection of suitable additives that may also contribute to the stabilization effect may also depend on the type of cell-containing sample to be stabilized. E.g. when processing whole blood as cell-containing biological sample, it is advantageous and also common to include an anticoagulant e.g. selected from the group consisting of heparin, ethylenediamine tetraacetic acid, citrate, oxalate, and any combination thereof. In an advantageous embodiment, the anticoagulant is a chelating agent. A chelating agent is an organic compound that is capable of forming coordinate bonds with metals through two or more atoms of the organic compound. Chelating agents according to the present invention include, but are not limited to diethylenetriaminepentaacetic acid (DTPA), ethylenedinitrilotetraacetic acid (EDTA), ethylene glycol tetraacetic acid (EGTA) and N,N-bis(carboxymethyl)glycine (NTA). According to a preferred embodiment, EDTA is used. As used herein, the term "EDTA" indicates inter alia the EDTA portion of an EDTA compound such as, for example, $K_2EDTA$, $K_3EDTA$ or $Na_2EDTA$. Using a chelating agent such as EDTA also has the advantageous effect that nucleases such as DNases are inhibited, thereby e.g. preventing a degradation of extracellular DNA by DNases. Furthermore, it was found by the inventors that EDTA used/added in higher concentrations is capable of reducing the release of intracellular nucleic acids, in particular genomic DNA from the cells thereby supporting the stabilizing effect that is achieved by the apoptosis inhibitor, the hypertonic agent and/or the at least one compound according to formula 1. However, EDTA alone is not capable of efficiently inhibiting the fragmentation of e.g. genomic DNA that is released from the cells contained in the sample. Thus, EDTA does not achieve a sufficient stabilization effect. But used in combination with the teachings of the present invention, in particular in combination with the apoptosis inhibitor, in particular the caspase inhibitor, it can further improve the stabilization for the above discussed reasons. Furthermore, it also appears to increase the chemical stability of RNA. According to one embodiment, the concentration of the chelating agent, preferably EDTA, in the biological sample that is mixed with one or more of the stabilizing compounds described above is in the range selected from the group consisting of 0.05 mM to 100 mM, 0.05 mM to 50 mM, 0.1 mM to 30 mM, 1 mM to 20 mM and 2 mM to 15 mM after the contacting step. Respective concentrations are particularly effective when stabilising blood, plasma and/or serum samples, in particular 10 ml blood samples.

Additional additives can also be used in order to further support the stabilization of the cell-containing sample, respectively support the preservation of the extracellular nucleic acid population. Examples of respective additives include but are not limited to nuclease inhibitors, in particular RNase and DNase inhibiting compounds. Examples of RNase inhibitors include but are not limited to anti-nuclease antibodies or ribonucleoside-vanadyl-complexes. When choosing a respective further additive, care should be taken not to compromise and/or counteract the stabilizing effect of the apoptosis inhibitor, the hypertonic agent and/or the compound according to formula 1. Thus, no additives should be used in concentrations that result in or support the lysis and/or degradation of the cells contained in the biological sample and/or which support the degradation of the nucleic acids contained in the cell-free fraction of the biological sample.

In an advantageous embodiment of the present invention, the cell-containing biological sample, which preferably is a blood sample or a sample derived from blood such as plasma or serum, is contacted with:
a) at least one caspase inhibitor as an apoptosis inhibitor, preferably with Q-VD-OPh, preferably in a concentration range of 1 μM to 30 μM;
b) optionally at least one hydroxylated organic compound such as dihydroxyacetone as hypertonic agent, preferably in a concentration range of 0.1M to 0.6M; and
c) optionally at least one compound according to formula 1 defined above (preferred embodiments and concentrations are described above) and/or d) a further additive, preferably a chelating agent preferably in a concentration range of 4 mM to 50 mM, preferably 4 mM to 20 mM, most preferably EDTA.

The components of the stabilizing composition can be comprised, respectively dissolved in a buffer, e.g. a biological buffer such as MOPS, TRIS, PBS and the like.

The apoptosis inhibitor, the hypertonic agent and/or the compound according to formula 1 as defined above as well as the optionally present further additives can be e.g. present in a device, preferably a container, for collecting the sample or can be added to a respective collection device immediately prior to collection of the biological sample; or can be added to the collection device immediately after the sample was collected therein. It is also within the scope of the present invention to add the stabilizing agent(s) and optionally, the further additive(s) separately to the cell containing biological sample. However, for the ease of handling, it is preferred that the one or more stabilizing agents and optionally the further additives are provided in one composition. Furthermore, in an advantageous embodiment, the apoptosis inhibitor, the hypertonic agent and/or the compound according to formula 1 as described above and optionally the further additive(s) are present in the collection device prior to adding the sample. This ensures that the cell-containing biological sample is immediately stabilized upon contact with the stabilizing agent(s). The stabilisation agent(s) are present in the container in an amount effective to provide the stabilisation of the amount of cell containing sample to be collected, respectively comprised in said container. As described, the sample can be mixed with the stabilization agent(s) directly after and/or during collection of the sample thereby providing a stabilized sample.

Preferably, the sample is mixed with the stabilization agent(s) directly after and/or during the collection of the sample. Therefore, preferably, the stabilization agent(s) and additives described above are provided in form of a stabilizing composition. Preferably, said stabilizing composition is provided in liquid form. It can be e.g. pre-filled in the sample collection device so that the sample is immediately stabilized during collection. According to one embodiment, the stabilizing composition is contacted with the cell-containing sample in a volumetric ratio selected from 10:1 to 1:20, 5:1 to 1:15, 1:1 to 1:10 and 1:2 to 1:5. It is a particular advantage of the teachings of the present invention that stabilization of a large sample volume can be achieved with a small volume of the stabilizing composition. Therefore, preferably, the ratio of stabilizing composition to sample lies in a range from 1:2 to 1:7, more preferred 1:3 to 1:5.

The term "cell-containing sample" as used herein, in particular refers to a sample which comprises at least one cell. The cell-containing sample may comprise at least two, at least 10, at least 50, at least 100, at least 250, at least 500, at least 1000, at least 1500, at least 2000 or at least 5000 cells. Furthermore, also cell-containing samples comprising considerably more cells are encompassed by said term and can be stabilized with the teachings according to the present invention. However, the term "cell-containing sample" also refers to and thus encompasses cell-depleted samples, including cell-depleted samples that are commonly referred to as "cell-free" such as e.g. blood plasma as respective samples often include residual cells. At least, it can often not be fully excluded that even so-called "cell-free" samples such as blood plasma comprise residual amounts of cells which accordingly, pose a risk that the extracellular nucleic acid population becomes contaminated with intracellular nucleic acids released from said residual cells. Therefore, respective cell-depleted and "cell-free" samples are according to one embodiment also encompassed by the term "cell-containing sample". Thus, the "cell-containing sample" may comprise large amounts of cells, as is the case e.g. with whole blood, but may also only comprise merely minor amounts of cells. Hence, the term "cell containing sample" also encompasses samples that may only be suspected of or pose a risk of containing cells. As discussed above, also with respect to biological samples which only comprise minor, respectively residual amounts of cells such as e.g. blood plasma (blood plasma contains—depending on the preparation method—usually small residual amounts of cells, even though it is commonly referred to as being cell-free), the method according to the present invention has considerable advantages as these residual cells may also result in a undesired contamination of the comprised extracellular nucleic acids. Using the stabilizing technology of the present invention also ensures that respective samples which only comprise residual amounts of cells or are merely suspected of or pose a risk of residual amounts of cells, are efficiently stabilized as is also described in detail above. Using the stabilizing method according to the present invention has the advantage that irrespective of the composition of the sample and the number of cells contained therein, the extracellular nucleic acid population contained therein is substantially preserved, respectively stabilized, thereby allowing for standardizing the subsequent isolation and/or analysis of the contained extracellular nucleic acids.

According to one embodiment, the cell-containing biological sample is selected from the group consisting of whole blood, samples derived from blood, plasma, serum, sputum, lachrymal fluid, lymphatic fluid, urine, sweat, liquor, cerebrospinal fluid, ascites, milk, stool, bronchial lavage, saliva, amniotic fluid, nasal secretions, vaginal secretions, semen/seminal fluid, wound secretions, and cell culture supernatants and supernatants obtained from other swab samples. According to one embodiment, the cell-containing biological sample is a body fluid, a body secretion or body excretion, preferably a body fluid, most preferably whole blood, plasma or serum. The cell-containing biological sample comprises extracellular nucleic acids. According to another embodiment, the cell-containing biological sample is a non-fluid sample derived from a human or animal, such as e.g. stool, tissue or a biopsy sample. Other examples of cell-containing biological samples that can be stabilized with the method according to the present invention include but are not limited to biological samples cell suspensions, cell cultures, supernatant of cell cultures and the like, which comprise extracellular nucleic acids.

As is described above and as is demonstrated by the examples, using the methods of the present invention allows for stabilizing the cell-containing sample without refrigeration or freezing for a prolonged period of time period. Thus, the samples can be kept at room temperature or even at elevated temperatures e.g. up to 30° C. or up to 40° C. According to one embodiment, a stabilization effect is achieved for at least two days, preferably at least three days; more preferred at least one day to six days, most preferred for at least one day to at least seven days at room temperature. As is shown in the examples, the samples that were stabilized according to the method of the present invention were not substantially compromised when stored for 3 days at room temperature. Even during longer storages for up to 6 or even 7 days at room temperature the extracellular nucleic acid population was substantially more stabilized compared to non-stabilized samples or e.g. compared to samples that were stabilized using standard method such as an EDTA treatment. Even though the stabilization effect may decrease over time, it is still sufficient to preserve the composition of the extracellular nucleic acid population to allow the analysis and/or further processing. Thus, samples that were stabilized according to the methods of the present invention were still suitable for isolating and optionally analysing the extracellular nucleic acids contained therein even after longer storage at room temperature. Thus, as the samples were not compromised in particular when using the preferred combination of stabilisation agents, even longer storage/shipping times are conceivable. However, usually, longer periods are not necessary, as the regular storage and e.g. shipping time to the laboratory, wherein the nucleic acid isolation and optionally analysis is performed, usually does not exceed 6 or 7 days, but usually is even completed after two or three days. As is shown in the examples, the stabilisation efficiency is particularly good during this time period. However, the extraordinary long stabilisation times and stabilisation efficiencies that are achievable with the method according to the present invention provides an important safety factor.

The methods and also the subsequently described compositions according to the present invention allow the stabilization also of large volumes of biological samples with small volumes of added substances because the additives that are used according to the teachings of the present invention are highly active. This is an important advantage because the size/volume of the sample poses considerable restrains on the subsequent isolation procedure in particular when intending to use automated processes for isolating the extracellular nucleic acids contained in the samples. Furthermore, one has to consider that extracellular nucleic acids are often only comprised in small amounts in the contained sample. Thus, processing larger volumes of a cell-containing sample such as e.g. a blood sample has the advantage that more circulating nucleic acids can be isolated from the sample and thus are available for a subsequent analysis.

The stabilization of the biological sample may either be followed directly by techniques for analysing nucleic acids, or the nucleic acids may be purified from the sample. Hence, the sample that was stabilized according to the method of the present invention can be analysed in a nucleic acid analytic and/or detection method and or may be further processed. E.g. extracellular nucleic acid can be isolated from the stabilized sample and can then be analysed in a nucleic acid analytic and/or detection method or may be further processed.

Furthermore, according to a second aspect, a method for isolating extracellular nucleic acids from a cell-containing biological sample is provided, wherein said method comprises the steps of:
  a) stabilizing the extracellular nucleic acid population comprised in a cell-containing sample according to the method defined in the first aspect of the present invention;
  b) isolating extracellular nucleic acids.

As discussed above, the stabilization according to the present invention has the effect that the extracellular nucleic acid population contained in the sample is substantially preserved in the state it had shown at the time the biological sample was obtained, respectively drawn. In particular, the usually observed high increase in nucleic acids that results from intracellular nucleic acids, in particular genomic DNA, more specifically fragmented genomic DNA, released from damaged or dying cells is efficiently reduced as is demonstrated in the examples. Therefore, the extracellular nucleic acids obtained from a respectively stabilized sample comprise fewer contaminations with intracellular nucleic acids originating from degraded or dying cells comprised in the sample and in particular comprise less amounts of fragmented genomic DNA compared to non-stabilized samples. Furthermore, the unique stabilization step allows to increase the amount of recoverable extracellular nucleic acids. The stabilization method according to the present invention can be performed without the crosslinking of the sample. This is an important advantage over the use of cross-linking agents such as formaldehyde or formaldehyde releasers, as these reagents might reduce the recoverable amount of extracellular nucleic acids due to cross-linking. Thus, the method according to the present invention improves the diagnostic and prognostic capability of the extracellular nucleic acids. Furthermore, said stabilization allows the sample to be stored and/or handled, e.g. transported,—even at room temperature—for a prolonged period of time prior to separating the cells contained in the sample and/or prior to isolating the extracellular nucleic acids comprised therein in step b). With respect to the details of the stabilization, it is referred to the above disclosure which also applies here.

According to one embodiment, the cell-containing biological sample such as e.g. a whole blood sample is stabilized in step a) as is described in detail above using at least one apoptosis inhibitor, at least one hypertonic agent and/or at least one compound according to formula 1 as described above, preferably using at least two of these stabilizing agents and optionally, further additives. Suitable and preferred embodiments were described above. Particularly preferred is the use of a caspaseinhibitor in combination with an anticoagulant, preferably a chelating agent as described above, for stabilizing whole blood samples.

If the sample comprises large amounts of cells as is e.g. the case with whole blood, the cells are separated from the remaining sample in order to obtain a cell-free, respectively cell-reduced or cell-depleted fraction of the sample which comprises the extracellular nucleic acids. Thus, according to one embodiment, cells are removed from the cell-containing sample between step a) and step b). This intermediate step is only optional and e.g. may be obsolete if samples are processed which merely comprise minor amounts of residual cells such as e.g. plasma or serum. However, in order improve the results it is preferred that also respective remaining cells (or potentially remaining cells) are removed as they might contaminate the extracellular nucleic acid population during isolation. Depending on the sample type, cells, including residual cells, can be separated and removed e.g. by centrifugation, preferably high speed centrifugation, or by using means other than centrifugation, such as e.g. filtration, sedimentation or binding to surfaces on (optionally magnetic) particles if a centrifugation step is to be avoided. Respective cell removal steps can also be easily included into an automated sample preparation protocol. Respectively removed cells may also be processed further. The cells can e.g. be stored and/or biomolecules such as e.g. nucleic acids or proteins can be isolated from the removed cells.

Furthermore, it is also within the scope of the present invention to include further intermediate steps to work up the sample.

Extracellular nucleic acids are then isolated in step b), e.g. from the cell-free, respectively cell-depleted fraction, e.g. from supernatants, plasma and/or serum. For isolating extracellular nucleic acids, any known nucleic acid isolation method can be used that is suitable for isolating nucleic acids from the respective sample, respectively the cell-depleted sample. Examples for respective purification methods include but are not limited to extraction, solid-phase extraction, silica-based purification, magnetic particle-based purification, phenol-chloroform extraction, chromatography, anion-exchange chromatography (using anion-exchange surfaces), electrophoresis, filtration, precipitation, chromatin immunoprecipitation and combinations thereof. It is also within the scope of the present invention to specifically isolate specific target extracellular nucleic acids, e.g. by using appropriate probes that enable a sequence specific binding and are coupled to a solid support. Also any other nucleic acid isolating technique known by the skilled person can be used. According to one embodiment, the nucleic acids are isolated using a chaotropic agent and/or alcohol. Preferably, the nucleic acids are isolated by binding them to a solid phase, preferably a solid phase comprising silica or anion exchange functional groups. Suitable methods and kits are also commercially available such as the QIAamp® Circulating Nucleic Acid Kit (QIAGEN), the Chemagic Circulating NA Kit (Chemagen), the NucleoSpin Plasma XS Kit (Macherey-Nagel), the Plasma/Serum Circulating DNA Purification Kit (Norgen Biotek), the Plasma/Serum Circulating RNA Purification Kit (Norgen Biotek), the High Pure Viral Nucleic Acid Large Volume Kit (Roche) and other commercially available kits suitable for extracting and purifying circulating nucleic acids.

According to one embodiment, all nucleic acids that are comprised in the sample that is obtained after step a) or optionally obtained after the cells have been removed in the intermediate step are isolated, e.g. are isolated from the cell-free, respectively cell-depleted fraction. E.g. total nucleic acids can be isolated from plasma or serum and the extracellular nucleic acids will be comprised as a portion in these extracted nucleic acids. If the cells are efficiently removed, the total nucleic acids isolated will predominantly comprise or even consist of extracellular nucleic acids. It is also within the scope of the present invention to isolate at least predominantly a specific target nucleic acid. A target nucleic acid can be e.g. a certain type of nucleic acid, e.g. RNA or DNA, including mRNA, microRNA, other non-coding nucleic acids, epigenetically modified nucleic acids, and other nucleic acids. It is also within the scope of the present invention to e.g. digest the non-target nucleic acid using nucleases after isolation. The term target nucleic acid also refers to a specific kind of nucleic acid, e.g. a specific extracellular nucleic acid that is known to be a certain disease marker. As discussed above, the isolation of extracellular nucleic acids may also comprise the specific isolation of a respective target nucleic acid e.g. by using appropriate capture probes. The term a target nucleic acid also refers to a nucleic acid having a certain length, e.g. a nucleic acid having a length of 2000 nt or less, 1000 nt or less or 500 nt or less. Isolating respective smaller target nucleic acids can be advantageous because it is known that extracellular nucleic acids usually have a smaller size of less than 2000 nt, usually less than 1000 nt and often even less than 500 nt. The sizes, respectively size ranges indicated herein refer to the chain length. I.e. in case of DNA it refers to bp. Focusing the isolation, respectively purification, on respective small nucleic acids can increase the portion of extracellular nucleic acids obtained in the isolated nucleic acids. The stabilization methods according to the present invention allow, in particular due to the inhibition of fragmentation of genomic, intracellular DNA, for a more efficient separation of such high molecular weight genomic DNA from the fragmented extracellular nucleic acid population, e.g., during the nucleic acid extraction procedure. As the substantial size difference between genomic and circulating nucleic acids is essentially preserved using the stabilization technology according to the present invention, genomic DNA can be removed e.g. by size-selective recovery of DNA more efficiently than without the respective stabilization. Suitable methods to achieve a respective selective isolation of the extracellular nucleic acid population e.g. by depleting the high molecular weight genomic DNA are well-known in the prior art and thus, need no further description here. E.g. it would be sufficient to use a size-selection method that depletes a sample of any nucleic acid larger than 1,000-10,000 nucleotides or base pairs. As the size difference between genomic (usually larger than >10,000 bp) and extracellular nucleic acids (usually <1000 bp) in a stabilized sample according to the present invention is usually relatively large due to the efficient stabilization (the difference can e.g. lie in a range of 1000-10,000 bp), known methods for selectively isolating extracellular nucleic acid from a biological sample could be applied. This also provides further opportunities in order to reduce the amount of intracellular nucleic acids in the isolated extracellular nucleic acid population. For example, the removal of genomic DNA during the nucleic acid extraction protocol could also supplement or even replace a separate high g-force centrifugation of a plasma sample before starting the nucleic acid extraction in order to remove residual cells. Genomic DNA that is released from said residual cells is prevented from becoming massively degraded due to the stabilization according to the present invention, and accordingly, can be removed by size-selective isolation protocols. This option is of particular advantage, as many clinical laboratories do not have a centrifuge capable of performing such a high g-force centrifugation or other means for removing in particular trace amounts of residual cells.

The isolated nucleic acids can then be analysed and/or further processed in a step c) using suitable assay and/or analytical methods. E.g. they can be identified, modified, contacted with at least one enzyme, amplified, reverse transcribed, cloned, sequenced, contacted with a probe, be detected (their presence or absence) and/or be quantified. Respective methods are well-known in the prior art and are commonly applied in the medical, diagnostic and/or prognostic field in order to analyse extracellular nucleic acids (see also the detailed description in the background of the present invention). Thus, after extracellular nucleic acids were isolated, optionally as part of total nucleic acid, total RNA and/or total DNA (see above), they can be analysed to identify the presence, absence or severity of a disease state including but not being limited to a multitude of neoplastic diseases, in particular premalignancies and malignancies such as different forms of cancers. E.g. the isolated extracellular nucleic acids can be analysed in order to detect diagnostic and/or prognostic markers (e.g., fetal- or tumor-derived extracellular nucleic acids) in many fields of application, including but not limited to non-invasive prenatal genetic testing respectively screening, disease screening, pathogen screening, oncology, cancer screening, early stage cancer screening, cancer therapy monitoring, genetic testing (genotyping), infectious disease testing, injury diagnostics, trauma diagnostics, transplantation medicine or many other diseases and, hence, are of diagnostic and/or prognostic relevance. According to one embodiment, the isolated extracellular nucleic acids are analyzed to identify and/or characterize a disease or a fetal characteristic. Thus, as discussed above, the isolation method described herein may further comprise a step c) of nucleic acid analysis and/or processing. Therefore, according to one embodiment, the isolated extracellular nucleic acids are analysed in step c) to identify, detect, screen for, monitor or exclude a disease and/or at least one fetal characteristic. The analysis/further processing of the nucleic acids can be performed using any nucleic acid analysis/processing method including, but not limited to amplification technologies, polymerase chain reaction (PCR), isothermal amplification, reverse transcription polymerase chain reaction (RT-PCR), quantitative real time polymerase chain reaction (Q-PCR), digital PCR, gel electrophoresis, capillary electrophoresis, mass spectrometry, fluorescence detection, ultraviolet spectrometry, hybridization assays, DNA or RNA sequencing, restriction analysis, reverse transcription, NASBA, allele specific polymerase chain reaction, polymerase cycling assembly (PCA), asymmetric polymerase chain reaction, linear after the exponential polymerase chain reaction (LATE-PCR), helicase-dependent amplification (HDA), hot-start polymerase chain reaction, intersequence-specific polymerase chain reaction (ISSR), inverse polymerase chain reaction, ligation mediated polymerase chain reaction, methylation specific polymerase chain reaction (MSP), multiplex polymerase chain reaction, nested polymerase chain reaction, solid phase polymerase chain reaction, or any combination thereof. Respective technologies are well-known to the skilled person and thus, do not need further description here.

According to one embodiment, either or both of the isolating or analyzing steps b) and c) occurs at least one day up to 7 days after the sample has been collected, respectively stabilized according to the teachings of the present invention. Suitable time periods for which the sample, in particular a blood sample, respectively the extracellular nucleic acid population contained therein can be stabilized using the method according to the present invention are also described above and also apply here. According to one embodiment, the isolation step is performed at least one day, at least 2 days, at least 3 days, at least 4 days, at least 5 days or at least 6 days after the sample was collected and stabilized according to the method according to the present invention. According to one embodiment, either or both of the isolating or analyzing steps occur without freezing the sample and/or without the use of formaldehyde for preserving the cell-containing biological sample. The biological sample is stabilized after the contact with the apoptosis inhibitor, the hypertonic agent and/or the compound according to formula 1 as defined above, preferably in combination with a further additive such as an anticoagulant like EDTA. An anticoagulant is preferably used when stabilizing blood or a sample derived from blood. The respectively stabilized samples can be handled, e.g. stored and/or shipped at room temperature.

Furthermore, according to a third aspect of the present invention a composition suitable for stabilizing the extracellular nucleic acid population in a biological sample is provided, comprising:
  a) at least one apoptosis inhibitor, preferably a caspase inhibitor, and/or
  b) at least one hypertonic agent which stabilizes cells comprised in the sample, preferably dihydroxyacetone; and/or
  c) at least one compound according to formula 1 as defined above; and
  d) optionally at least one anticoagulant, preferably a chelating agent.

As discussed above, a respective stabilizing composition is particularly effective in stabilizing a cell-containing biological sample, in particular whole blood, plasma and/or serum by stabilizing the comprised cells and the comprised extracellular nucleic acids thereby substantially preserving, respectively stabilizing the extracellular nucleic acid population. A respective stabilizing composition allows the storage and/or handling, e.g. shipping, of the sample, which preferably is whole blood, at room temperature for at least two, preferably at least three days without substantially compromising the quality of the sample, respectively the extracellular nucleic acid population contained therein. Of course, it is not mandatory to make use of the full possible stabilization period; the samples may also be processed earlier if desired. Contacting the biological sample with the stabilizing composition allows the sample to be stored, and or handled, e.g. shipped, even at room temperature prior to isolating and optionally analysing and/or processing the contained circulating nucleic acids. Thus, the time between the collection or stabilization of the sample and the nucleic acid extraction can vary without substantially affecting the population, respectively the composition of the extracellular nucleic acid population contained therein. In particular, dilutions, respectively contaminations with intracellular nucleic acids, in particular fragmented genomic DNA, are reduced. Preferably, the stabilization composition is contacted with the sample immediately after or during collection of the sample. Preferably, when stabilizing a blood sample, the composition comprises at least one caspase inhibitor and at least one anticoagulant, preferably a chelating agent as described above. It may also comprise further stabilizing agents as described herein.

Suitable and preferred embodiments of the apoptosis inhibitor, the hypertonic agent and/or the compound according to formula 1 as well as suitable and preferred concentrations of the respective compounds are described in detail above in conjunction with the stabilization method. It is referred to the above disclosure which also applies with respect to the stabilization composition. Preferably, at least one caspase inhibitor, preferably a modified caspase specific peptide, preferably modified at the C-terminus with an O-phenoxy group such as Q-VD-OPh, is used in combination with at least one hypertonic agent, preferably a hydroxylated organic compound such as dihydroxyacetone. Other suitable hydroxylated organic compounds are also described above, it is referred to the respective disclosure. As is demonstrated by the examples, a respective combination is remarkably effective in stabilizing a cell-containing biological sample, in particular a blood sample.

Preferably, the at least one compound according to formula 1 is a N,N-dialkyl-carboxylic acid amide. Preferred R1, R2, R3 and R4 groups are described above. According to one embodiment, the compound is selected from the group consisting of N,N-dimethylacetamide; N,N-diethylacetamide; N,N-dimethylformamide, N,N-diethylformamide and N,N-dimethylpropanamid. Said compound can also be used in combination with an apoptosis inhibitor, preferably a caspase inhibitor (preferred embodiments are described above, it is referred to the above disclosure) and/or a hypertonic agent, preferably a hydrxycarbon compound (preferred embodiments are described above, it is referred to the above disclosure).

Furthermore, it is preferred that the stabilization composition comprises further additives, e.g. an anticoagulant such as a chelating agent in particular if the composition is used for stabilizing whole blood, plasma or serum.

According to one embodiment, the stabilizing composition consists essentially of the mentioned stabilizers and optional additives and optionally, buffering agents. The stabilizing composition stabilizes the sample and thus, does not promote the lysis and/or disruption of the cells contained in the sample. The stabilizing composition may reduce the damage of the cells comprised in the sample as can be e.g. determined by the assay methods described in the example section.

The composition may be provided in a solid form. This is e.g. a suitable option if the biological sample to be stabilized contains liquid to dissolve the solid (such as for example cell-containing body fluids, cells in medium, urine) or if liquid, e.g. water is added thereto to dissolve the solid. The advantage of using a solid stabilizing composition is that solids are usually chemically more stable. However, also a liquid composition may be used. Liquid compositions often have the advantage that the mixture with the sample to be stabilised can be quickly achieved, thereby basically providing an immediate stabilising effect as soon as the sample comes into contact with the liquid stabilizing composition. Preferably, stabilising agent(s) present in the liquid stabilizing composition remain stable in solution and require no pre-treatment-such as for example the dissolving of precipitates of limited solubility-by the user because pre-treatments of this kind pose a risk of variations in the stabilising efficiency.

Also provided is a mixture comprising the stabilizing composition according to the present invention mixed with a biological sample. Suitable and preferred examples of biological samples as well as suitable concentrations of the stabilizing agent(s) when mixed with the biological sample are described above in conjunction with the stabilizing method. It is referred to the above disclosure which also applies here. Preferably, the stabilizing composition is pre-filled in a sample collection device so that the sample is immediately stabilized during collection. According to one embodiment, the stabilizing composition is contacted with the biological sample in a volumetric ratio selected from 10:1 to 1:20, 5:1 to 1:15, 1:1 to 1:10 and 1:2 to 1:5. It is a particular advantage of the stabilizing composition of the present invention that stabilization of a large sample volume can be achieved with a small volume of the stabilizing composition. Therefore, preferably, the ratio of stabilizing composition to sample lies in a range from 1:2 to 1:7, more preferred 1:3 to 1:5.

The stabilizing composition according to the third aspect of the present invention can be used to stabilize the extracellular nucleic acid population comprised in a cell-containing sample. Furthermore, the stabilizing composition according to the third aspect of the present invention may also be used for stabilizing cells contained in a sample. As described above, the stabilizing composition inter alia reduces the release of genomic DNA from cells that results from decaying cells. Thus, a respective use is also an advantageous and provided by the teachings according to the present invention.

Also provided is a method of manufacturing a composition according to the third aspect of the present invention is provided, wherein the components of the composition are mixed, preferably in an aqueous solution.

The composition of the present invention may also be incorporated into a sample collection device, in particular blood collection assembly, thereby providing for a new and useful version of such a device. Such devices typically include a container having an open and a closed end. The container is preferably a blood collection tube. The container type also depends on the sample to be collected, other suitable formats are described below.

Furthermore, the present invention provides a container for collecting a cell-containing biological sample, preferably a blood sample, wherein the container comprises a stabilizing composition according to the present invention. Providing a respective container, e.g. a sample collection tube, which comprises the stabilizing composition according to the present invention, has the advantage that the sample is quickly stabilized when the sample is collected in the respective container. Details with respect to the stabilizing composition were described above, it is referred to the above disclosure which also applies here.

According to one embodiment, a collection container for receiving and collecting a biological sample is provided wherein the container comprises:

a) at least one apoptosis inhibitor such that when the sample is collected, the concentration of the apoptosis inhibitor or combination of two or more apoptosis inhibitors in the resulting mixture is selected from at least 0.01 µM, at least 0.05 µM, at least 0.1 µM, at least 0.5 µM, at least 1 µM, at least 2.5 µM or at least 3.5 µM and preferably is present in a concentration range selected from 0.01 µM to 100 µM, 0.05 µM to 100 µM, 0.1 µM to 50 µM, 1 µM to 40 µM, 1.0 µM to 30 µM or 2.5 µM to 25 µM and/or b) at least one hypertonic agent such that when the sample is collected, the concentration of the hypertonic agent or combination of two or more apoptosis inhibitors in the resulting mixture is at least 0.05M, at least 0.1M, preferably at least 0.25M, and preferably is present in a concentration range from 0.05M to 2M, 0.1M to 1.5M, 0.15M to 0.8M, 0.2M to 0.7M or 0.1M to 0.6M; and/or c) at least one compound according to formula 1 as defined above, such that when the sample is collected the compound according to formula 1 is comprised in a concentration of at least 0.1%, at least 0.5%, at least 0.75%, at least 1%, at least 1.25% or at least 1.5% or wherein said compound is comprised in a concentration range selected from 0.1% up to 50%. 0.1 to 30%, 1% to 20%, 1% to 10%, 1% to 7.5% and 1% to 5%; and/or d) optionally at least one further additive, preferably an anticoagulant such as a chelating agent, preferably EDTA if the container is for collecting blood or a blood product. Suitable concentrations are described above and preferably lie in the range of 4 mM to 50 mM, more preferred 4 mM to 20 mM.

The pre-filled components a), b), c) and/or d) can be provided in a liquid or in a dry form. For stabilizing whole blood it is preferred to use at least components a) and d). Preferably, the stabilizing components are provided as a stabilizing composition. A dry form is e.g. a suitable option if the biological sample to be stabilized contains liquid to dissolve the solid (such as for example cell-containing body fluids, cells in medium, urine) or if liquid, e.g. water is added thereto to dissolve the solid. The advantage of using a solid stabilizing composition is that solids are usually chemically more stable than liquids. According to one embodiment, the inner wall of the container is treated/covered with a stabilizing composition according to the present invention. Said composition can be applied to the inner walls using e.g. a spray-dry-method. Liquid removal techniques can be performed on the stabilising composition in order to obtain a substantially solid state protective composition. Liquid removal conditions may be such that they result in removal of at least about 50% by weight, at least about 75% by weight, or at least about 85% by weight of the original amount of the dispensed liquid stabilising composition. Liquid removal conditions may be such that they result in removal of sufficient liquid so that the resulting composition is in the form of a film, gel or other substantially solid or highly viscous layer. For example it may result in a substantially immobile coating (preferably a coating that can be re-dissolved or otherwise dispersed upon contact with the cell-containing sample which preferably is a blood product sample). It is possible that lyophilization or other techniques may be employed for realizing a substantially solid form of the protective agent (e.g., in the form of one or more pellet). Thus, liquid removal conditions may be such that they result in a material that upon contact with the sample under consideration (e.g., a whole blood sample) the protective agent will disperse in the sample, and substantially preserve components (e.g., extracellular nucleic acids) in the sample. Liquid removal conditions may be such that they result in a remaining composition that is substantially free of crystallinity, has a viscosity that is sufficiently high that the remaining composition is substantially immobile at ambient temperature; or both.

However, also a liquid composition may be used. Liquid compositions often have the advantage that the mixture with the sample to be stabilised can be quickly achieved, thereby basically providing an immediate stabilising effect as soon as the sample comes into contact with the liquid stabilizing composition. Preferably, the stabilising agent(s) present in the liquid stabilizing composition remain stable in solution and require no pre-treatment—such as for example the dissolving of precipitates of limited solubility—by the user because pre-treatments of this kind pose a risk of variations in the stabilising efficiency.

The stabilizing composition is comprised in the container in an amount effective to provide the stabilisation of the amount of sample to be collected in said container. According to one embodiment, the liquid stabilizing composition is contacted with the biological sample in a volumetric ratio selected from 10:1 to 1:20, 5:1 to 1:15, 1:1 to 1:10 and 1:2 to 1:5. It is a particular advantage of the stabilizing composition of the present invention that stabilization of a large sample volume can be achieved with a small volume of the stabilizing composition. Therefore, preferably, the ratio of stabilizing composition to sample lies in a range from 1:2 to 1:7, more preferred 1:3 to 1:5.

According to one embodiment, the container is evacuated. The evacuation is preferably effective for drawing a specific volume of a fluid sample into the interior. Thereby, it is ensured that the correct amount of sample is contacted with the pre-filled amount of the stabilizing composition comprised in the container, and accordingly, that the stabilization is efficient. According to one embodiment, the container comprises a tube having an open end sealed by a septum. E.g. the container is pre-filled with a defined amount of the stabilizing composition either in solid or liquid form and is provided with a defined vacuum and sealed with a septum. The septum is constructed such that it is compatible with the standard sampling accessories (e.g. cannula, etc.). When contacted with e.g. the canula, a sample amount that is predetermined by the vacuum is collected in the container. A respective embodiment is in particular advantageous for collecting blood. A suitable container is e.g. disclosed in U.S. Pat. No. 6,776,959.

The container according to the present invention can be made of glass, plastic or other suitable materials. Plastic materials can be oxygen impermeable materials or may contain an oxygen impermeable layer. Alternatively, the container can be made of water- and air-permeable plastic material. The container according to the present invention preferably is made of a transparent material. Examples of suitable transparent thermoplastic materials include polycarbonates, polyethylene, polypropylene and polyethyleneterephthalate. The container may have a suitable dimension selected according to the required volume of the biological sample being collected. As described above, preferably, the container is evacuated to an internal pressure below atmospheric pressure. Such an embodiment is particularly suitable for collecting body fluids such as whole blood. The pressure is preferably selected to draw a predetermined volume of a biological sample into the container. In addition to such vacuum tubes also non-vacuum tubes, mechanical separator tubes or gel-barrier tubes can be used as sample containers, in particular for the collection of blood samples. Examples of suitable containers and capping devices are disclosed in U.S. Pat. No. 5,860,397 and US 2004/0043505. As container for collecting the cell-containing sample also further collection devices, for example a syringe, a urine collection device or other collection devices can be used. The type of the container may also depend on the sample type to be collected and suitable containers are also available to the skilled person.

In an advantageous embodiment the container respectively the device is filled or is pre-filled with at least one apoptosis inhibitor, preferably a caspase inhibitor, at least one hypertonic agent, preferably at least one hydroxylated organic compound as described in detail above, e.g. dihydroxyaceton and optionally a further additive such as an anticoagulant, preferably a chelating agent, more preferred EDTA. The mixture of at least one hypertonic agent, which preferably is a hydroxylated organic compound, e.g. a carbohydrate such as dihydroxyacetone and at least one caspase inhibitor, preferably Q-VD-OPH, unexpectedly stabilizes extracellular nucleic acids in whole blood, plasma or serum and prevents the release of cellular nucleic acids in particular from white blood cells that are contained in such samples. Hence, the extracellular nucleic acid population is preserved in the state it had shown at the time of blood draw. Beneficial results are also obtained when the container respectively the device is filled or is pre-filled with at least one compound according to formula 1 as defined above as stabilizing agent. Preferably, an anticoagulant is encompassed in addition to the compound according to formula 1. The anticoagulant is preferably a chelating agent such as EDTA. Furthermore, the stabilizing composition comprised in the container may also comprise an apoptosis inhibitor, preferably a caspase inhibitor and/or at least one hypertonic agent, preferably at least one hydroxylated organic compound as described in detail above, e.g. dihydroxyaceton and optionally further additives. According to one embodiment, the stabilizing composition comprised in the container comprises a caspase inhibitor and an anticoagulant.

According to one embodiment, the container has an open top, a bottom, and a sidewall extending therebetween defining a chamber, wherein the stabilization composition according to the present invention is comprised in the chamber. It may be comprised therein in liquid or solid form. According to one embodiment the container is a tube, the bottom is a closed bottom, the container further comprises a closure in the open top, and the chamber is at a reduced pressure. The advantages of a reduced pressure in the chamber were described above. Preferably, the closure is capable of being pierced with a needle or cannula, and the reduced pressure is selected to draw a specified volume of a liquid sample into the chamber.

According to one embodiment, the chamber is at a reduced pressure selected to draw a specified volume of a liquid sample into the chamber, and the stabilizing composition is a liquid and is disposed in the chamber such that the volumetric ratio of the stabilising composition to the specified volume of the cell-containing sample is selected from 10:1 to 1:20, 5:1 to 1:15, 1:1 to 1:10 and 1:2 to 1:5. The associated advantages were described above.

Preferably, the container is for drawing blood from a patient.

According to a fifth aspect, a method is provided comprising the step of collecting a sample from a patient directly into a chamber of a container according to the fourth aspect of the present invention. Details with respect to the container and the sample were described above. It is referred to the respective disclosure. According to one embodiment, a blood sample is collected, preferably it is withdrawn from the patient.

The methods and compositions disclosed herein allow for the efficient preservation and isolation of extracellular nucleic acids while reducing possible mixing with nucleic acids, in particular fragmented genomic DNA, which originates from cells comprised in the biological sample and which may enter a biological sample due to cell damage, respectively cell lysis. The methods according to the present invention, as well as the compositions and the disclosed devices (e.g. the collection containers) reduce the degradation of extracellular nucleic acids and also reduce cell lysis and/or release of genomic nucleic acids, in particular fragmented genomic DNA, so that the extracellular nucleic acids contained in the sample do not become contaminated with intracellular nucleic acids, respectively a respective contamination is reduced by the teachings according to the present invention. As discussed above, an intermixing of extracellular nucleic acids and cellular nucleic acids, in particular fragmented genomic DNA, may reduce the accuracy of any measurement of the amount of extracellular nucleic acids in a biological sample. As discussed above, an important advantage of the present invention is the possibility for essentially simultaneous stabilizing of both the cells contained in the sample (in particular white blood cells in case of whole blood, plasma or serum) and the extracellular nucleic acids. This helps to prevent cellular nucleic acids such as genomic DNA from being released into the cell-free portion of the sample, and further diluting the comprised extracellular nucleic acids (and associated biomarkers) of interest, while also maintaining the structural integrity of the extracellular nucleic acids. As discussed herein, contacting the cell-containing biological sample such as whole blood or plasma with the stabilising agent(s) allows the sample to be stored for a period of time prior to isolating the extracellular nucleic acids. More preferably, the cell-containing biological sample, e.g. blood or plasma, may be drawn at one location (e.g., a health care facility), contacted with the stabilising agent(s), and later transported to a different remote location (e.g., a laboratory) for the nucleic acid isolation and testing process.

Furthermore, the stabilization reagents, as disclosed in herein, provide an advantage over known state-of-the-art stabilization reagents which involve the use of cross-linking reagents, such as formaldehyde, formaldehyde releasers and the like, as the stabilization of samples according to the present invention does not involve the use to such cross-linking reagents. Crosslinking reagents cause inter- or intra-molecular covalent bonds between nucleic acid molecules or between nucleic acids and proteins. This effect can lead to a reduced recovery of such stabilized and partially crosslinked nucleic acids after a purification or extraction from a complex biological sample. As, for example, the concentration of circulating nucleic acids in a whole blood samples is already relatively low, any measure which further reduces the yield of such nucleic acids should be avoided. This may be of particular importance when detecting and analyzing very rare nucleic acid molecules derived from malignant tumors or from a developing fetus in the first trimester of pregnancy. Therefore, according to one embodiment, no formaldehyde releaser is comprised in the stabilizing composition, respectively is not additionally used for stabilization. According to one embodiment, the apoptosis inhibitor that is used in the methods and/or compositions according to the present invention is not selected from the group consisting of aurintricarboxylic acid, phenylmethylsulfonyl fluoride (PMSF), leupeptin and Na-Tosyl-Lys chloromethyl ketone hydrochloride (TLCK). According to one embodiment, the apoptosis inhibitor is not selected from said group in particular if the apoptosis inhibitor is not used in combination with a hypertonic agent as additional stabilizer.

This invention is not limited by the exemplary methods and materials disclosed herein, and any methods and materials similar or equivalent to those described herein can be used in the practice or testing of embodiments of this invention. Numeric ranges are inclusive of the numbers defining the range. The headings provided herein are not limitations of the various aspects or embodiments of this invention which can be read by reference to the specification as a whole.

The term "solution" as used herein in particular refers to a liquid composition, preferably an aqueous composition. It may be a homogenous mixture of only one phase but it is also within the scope of the present invention that a solution comprises solid additives such as e.g. precipitates.

The sizes, respectively size ranges indicated herein with reference to nucleotides nt, refer to the chain length and thus are used in order to describe the length of single-stranded as well as double-stranded molecules. In double-stranded molecules said nucleotides are paired.

According to one embodiment, subject matter described herein as comprising certain steps in the case of methods or as comprising certain ingredients in the case of compositions, solutions and/or buffers refers to subject matter consisting of the respective steps or ingredients. It is preferred to select and combine preferred embodiments described herein and the specific subject-matter arising from a respective combination of preferred embodiments also belongs to the present disclosure.

TABLE 1

| Overview of apoptosis inhibitors | |
|---|---|
| Apoptosis inhibitor | Description |
| 1. Metabolic inhibitors | |
| AICA-Riboside, Acadesine, AICAr, 5-Aminoimidazole-4-carboxamide-1-β-riboside, Z-Riboside | Offers protection against cell death induced by glucose deprivation |
| Apoptosis Inhibitor II, diarylurea compound | prevents the active ~700-kDa apoptosome complex formation |

TABLE 1-continued

Overview of apoptosis inhibitors

| Apoptosis inhibitor | Description |
| --- | --- |
| Bax Channel Blocker, (±)-1-(3,6-Dibromocarbazol-9-yl)-3-piperazin-1-yl-propan-2-ol, bis TFA, iMAC1 | A cell-permeable dibromocarbazolo-piperazinyl derivative that displays anti-apoptotic properties. Effectively blocks Bid-induced cyctochrome c release from HeLa cell mitochondria (~80% inhibition at 5 μM) by inhibiting Bax channel-forming activity (IC50 = 520 nM in a liposome channel assay). |
| Bax-Inhibiting Peptide, V5 Peptide sequence: H-Val-Pro-Met-Leu-Lys-OH (SEQ ID NO: 1) | A cell-permeable pentapeptide based on the Ku70-Bax inhibiting domain that offers cytoprotection. Functions as effectively as the Caspase Inhibitor VI (Z-VAD-FMK; Cat. No. 219007) for Bax-mediated apoptosis (~50-200 μM). Also effectively blocks caspase-independent necrotic cell death. Shown to be Ku70 competitive, interact with Bax, prevent its conformational change and mitochondrial translocation. Displays extended stability in culture medium (~3 days). Negative control peptide is also available |
| Bcl-xL BH44-23, Human, Cell-Permeable | A cell-permeable peptide that prevents apoptotic cell death by directly binding to the voltage-dependent anion channel (VDAC) and blocking its activity. Leads to the inhibition of cytochrome c release and loss of mitochondrial membrane potential (ΔΨm). Contains the conserved N-terminal homology domain (BH4) of Bcl-xL (amino acids 4-23) that has been shown to be essential for inhibiting VDAC activity in liposomes and in isolated mitochondria. The BH4 domain is linked to a carrier peptide, a 10-amino acid HIV-TAT48-57 sequence with a β-alanine residue as a spacer for maximum flexibility. Following its uptake, it is mainly localized to the mitochondria |
| Bongkrekic Acid, Triammonium Salt | Acts as a ligand of the adenine nucleotide translocator. A potent inhibitor of mitochondrial megachannel (permeability transition pore). Significantly reduces signs of apoptosis induced by nitric oxide. Prevents the apoptotic breakdown of the inner mitochondrial transmembrane potential (ΔΨm), as well as a number of other phenomena linked to apoptosis |
| Daunorubicin, Hydrochloride | Potent cell-permeable anticancer agent whose potential target site may be mitochondrial cytochrome c oxidase. Has been shown to inhibit RNA and DNA synthesis. Inhibits eukaryotic topoisomerases I and II. Induces DNA single-strand breaks. Also induces apoptosis in HeLa S3 tumor cells. According to one embodiment, said compound is not used as stabilizer according to the present invention. |
| Humanin, Human, Synthetic | A 24-residue anti-apoptotic peptide that, when expressed intracellularly, offers protection against neuronal apoptosis induced by presenilin and APP (amyloid precursor protein) mutants associated with familial Alzheimer's disease (AD). Shown to reduce cytochrome c release in vitro by directly binding to Bax (Bcl-2-associated X protein; Kd ~2 nM) and preventing its association with isolated mitochondria |
| Phorbol-12-myristate-13-acetate | Most commonly-used phorbol ester. Extremely potent mouse skin tumor promoter. Activates protein kinase C in vivo and in vitro, even at nM concentrations. Promotes the expression of inducible NOS in cultured hepatocytes. Activates Ca2+-ATPase and potentiates forskolin-induced cAMP formation. Inhibits apoptosis induced by the Fas antigen, but induces apoptosis in HL-60 promyelocytic leukemia cells. Its binding is reversible |
| Pifithrin-α | A cell-permeable chemical inhibitor of p53. Reversibly inhibits p53-dependent transactivation of p53-responsive genes and reversibly blocks p53-mediated apoptosis. Inhibits p53-dependent growth arrest of human diploid fibroblasts in response to DNA damage but has no effect on p53-deficient fibroblasts. Protects normal tissues from the deleterious side effects of chemotherapy. Has been reported to protect neurons against β-amyloid peptide and glutamate-induced apoptosis |
| Pifithrin-μ | A cell-permeable sulfonamide that blocks p53 interaction with Bcl-xL and Bcl-2 proteins and selectively inhibits p53 translocation to mitochondria without affecting the transactivation function of p53. Effectively protects against γ radiation-induced cell death in vitro and animal lethality in vivo. Because Pifithrin-μ targets only the mitochondrial branch of the p53 pathway without affecting the important transcriptional functions of p53, it is superior to Pifithrin-α (Cat. No. 506132) in in vivo studies. Shown to selectively interact with inducible HSP70 and disrupt its functions |
| Pifithrin-α, Cyclic- | A cell-permeable and very stable analog of Pifithrin-α (Cat. No. 506132), with similar biological function, but with reduced cytotoxicity. A chemical inhibitor of p53. Reversibly inhibits p53-dependent transactivation of p53-responsive genes; also reversibly blocks p53-mediated apoptosis. Acts as a P-gp modulator by changing relative substrate specificity of the transporter. This compound has been reported to be a potent STAT6 transcriptional inhibitor |

TABLE 1-continued

Overview of apoptosis inhibitors

| Apoptosis inhibitor | Description |
|---|---|
| Pifithrin-α, p-Nitro | A cell-permeable p53 inhibitor that serves as the prodrug form of Pifithrin-α, p-Nitro, Cyclic (Cat. No. 506154). Although its in vitro efficacy (ED50 = 0.3 μM in protecting etoposide-induced cortical neuron death) is similar to that of Pifithrin-α (Cat. No. 506132), it is 100-fold more potent than Pifithrin-α when adminstered in rats in vivo due to its long-lasting, steady conversion to the corresponding cyclic form of active compound in biological systems (t½ = 8 h in neuron culture medium at 37° C.). |
| Pifithrin-α, p-Nitro, Cyclic | A cell-permeable p53 inhibitor that exhibits 10-fold higher potency (ED50 = 30 nM in protecting etoposide-induced cortical neuron death) and 50% longer half-life (t½ = 6 h in neuron culture medium at 37° C.) than Pifithrin-α (Cat. No. 506132). However, despite its in vitro efficacy, this inhibitor is not effective when adminstered in rats in vivo. For in vivo applications, please consider Pifithrin-α, p-Nitro (Cat. No. 506152). |
| STAT3 Inhibitor Peptide Peptide sequence: Ac-Pro-Tyr(PO3H2)-Leu-Lys-Thr-Lys-OH (SEQ ID NO: 2) | A Stat3-SH2 domain binding phosphopeptide that acts as a selective inhibitor of Stat3 (signal transducers and activators of transcription 3) signaling with a DB50 of 235 μM (concentration of peptide at which DNA-binding activity is inhibited by 50%). Significantly lowers the DNA-binding activity of Stat3 by forming an inactive Stat3:peptide complex and reduces the levels of active Stat3:Stat3 dimers that can bind DNA. Displays greater affinity for Stat3, and to a lesser extent Stat1, over Stat5. Supplied as a trifluoroacetate salt. |
| STAT3 Inhibitor Peptide, Cell-Permeable Peptide sequence: Ac-Pro-Tyr(PO3H2)-Leu-Lys-Thr-Lys-OH (SEQ ID NO: 2) | A cell-permeable analog of the Stat3-SH2 domain-binding phosphopeptide (Cat. No. 573095) that contains a C-terminal mts (membrane translocating sequence) and acts as a highly selective, potent blocker of Stat3 activation. Also suppresses constitutive Stat-3 dependent Src transformation with no effect on Stat-3 independent Ras transformation. The unphosphorylated inactive control peptide is also available under Cat. No. 573105. Supplied as a trifluoroacetate salt. |
| CAY10500, 6,7-dimethyl-3-{[methyl-[1-(3-trifluoromethyl-phenyl)-1H-indol-3-ylmethyl]-amino}-ethyl)-amino]-methyl}-chromen-4-one | Tumor necrosis factor α (TNFα) inhibitor that prevents binding to the TNF Receptor 1 (TNFR1).6 Binds to the biologically active TNFα trimer and promotes accelerated displacement of a single subunit to rapidly inactivate the cytokine. In a cell based assay, compound inhibited TNFα-mediated stimulation of IKB degradation. |
| Gambogic amide | A selective agonist for TrkA which mimics the actions of NGF. This compound possesses robust neurotrophic actvity, while it prevents neuronal cell death 1. |
| Maslinic Acid | A pentacyclic triterpene with antioxidant and anti-inflammatory properties. Shown to block the generation of nitric oxide, and inhibits the secretion of IL-6 and TNF-α induced by lipopolysaccharides |
| Naringin hydrate | A citrus bioflavonoid found to inhibit cytochrome P450 monooxygenase activity in mouse liver. It prevents toxin-induced cytoskeletal disruption and apoptotic liver cell death. |
| Necrostatin-1 | An inhibitor of necroptosis, a non-apoptotic cell death pathway. Does not affect Fas/TNFR-triggered apoptosis. According to one embodiment, said compound is not used as stabilizer according to the present invention. |
| NSC348884 hydrate, N1,N2-bis((3-imino-6-methyl-3H-indol-2-yl)methyl)-N1,N2-bis((6-methyl-1H-benzo[d]imidazol-2-yl)methyl)ethane-1,2-diamine hydrate | This product is a nucleolar phosphoprotein that displays several biological activities in ribosome biogenesis, cell proliferation, cytoplasmic/nuclear shuttle transportation, nucleic acid binding, ribonucleic cleavage, centrosome duplication and molecular chaperoning, and is found in higher levels in tumor cells. Overexpression has been shown to lead to inhibition of apoptosis. NSC34884 upregulates p53. |
| Orsellinic acid | Benzoic acid. Blocks PAF-mediated neuronal apoptosis. Shows free radical scavenging activity. |
| tetramethyl Nordihydroguaiaretic Acid | A synthetic derivative of NDGA and a non-selective lipoxygenase inhibitor. It inhibits Sp1 transcription factor binding at the HIV long terminal repeat promoter and at the α-ICP4 promoter (a gene essential for HSV replication). |
| GW 4869, 3,3'-(1,4-phenylene)bis[N-[4-(4,5-dihydro-1H-imidazol-2-yl)phenyl]-hydrochloride-2-propenamide | A cell-permeable, symmetrical dihydroimidazolo-amide compound that acts as a potent, specific, non-competitive inhibitor of N-SMase (neutral sphingomyelinase) [IC50 = ~1 μM, rat brain; Km for sphingomyelin ~13 μM]. Does not inhibit human A-SMase (acid sphingomyelinase) even at 150 μM. Weakly inhibits the activities of bovine protein phosphatase 2A and mammalian lyso-PAF PLC, while no inhibition is observed for bacterial phosphatidylcholine-specific PLC. Reported to offer complete protection against TNF-α or diamine-induced cell death in MCF7 breast cancer cells at 20 μM. Does not modify the intracellular glutathione levels or interfere with TNF-α or diamine-mediated signaling effects. |

TABLE 1-continued

Overview of apoptosis inhibitors

| Apoptosis inhibitor | Description |
|---|---|
| SP 600125, 1,9-Pyrazoloanthrone, Anthrapyrazolone | SP600125 is a JNK inhibitor (IC50 = 40 nM for JNK-1 and JNK-2 and 90 nM for JNK-3). This agent exhibits greater than 300-fold selectivity for JNK against related MAP kinases ERK1 and p38-2, and the serine threonine kinase PKA. [1] SP600125 is a reversible ATP-competitive inhibitor. In cells, SP600125 dose dependently inhibited the phosphorylation of c-Jun, the expression of inflammatory genes COX-2, IL-2, IFN-γ, TNF-α, and prevented the activation and differentiation of primary human CD4 cell cultures |
| Mdivi-1, 3-(2,4-Dichloro-5-methoxyphenyl)-2,3-dihydro-2-thioxo-4(1H)-quinazolinone, 3-(2,4-Dichloro-5-methoxyphenyl)-2-sulfanyl-4(3H)-quinazolinone | Mdivi-1 is a selective inhibitor of mitochondrial division in yeast and mammalian cells which acts via inhibiting the mitochondrial division dynamin. In cells, Mdivi-1 inhibits apoptosis by inhibiting mitochondrial outer membrane permeabilization. Mdivi-1 causes the rapid (<5 min) reversible and dose-dependent formation of net-like mitochondria in wild-type cells with an IC50 = ~10 μM. In yeast, time-lapse fluorescence microscopy revealed no detectable mitochondrial division after treatment with Mdivi-1 |
| Minocycline•hydrochloride | Tetracycline derivative with antimicrobial activity. Inhibitor of angiogenesis, apoptosis and poly(ADP-ribose) polymerase-1 (PARP-1). Anti-inflammatory and neuroprotective |
| Ro 08-2750 (C13H10N4O3) | Inhibitor of NGF-induced apoptosis. |
| RKTS-33 (C7H8O4) | selective inhibition of Fas ligand-dependent pathway alone |

2. Nucleic acids

| | |
|---|---|
| 3,4-Dichloroisocoumarin | Inhibitor of serine proteases –> granzyme B and blocks apoptotic internucleosomal DNA cleavage in thymocytes without the involvement of endonucleases. Does not affect thiol proteases and metalloproteases |
| Actinomycin D, *Streptomyces* sp. | Also acts as a competitive inhibitor of serine proteases; Classical anti-neoplastic drug. Cytotoxic inducer of apoptosis against tumor cells. A DNA dependent inhibitor of RNA synthesis, actinomycin promotes induction of apoptosis by some specific stimuli, for example, TRAIL and Fas (CD95). Actinomycin D can also alleviate or block the apoptotic process and decrease the cytotoxicity induced by several stimuli such as the dihydrofolate reductase inhibitor aminopterin and the prostaglandin derivative 15-deoxy-D12,14-prostaglandin J2, thus it can have both pro and anti-apoptotic activities in some systems. According to one embodiment, said compound is not used as stabilizer according to the present invention. |
| Aurintricarboxylic Acid | Inhibitor of DNA topoisomerase II |
| Baicalein | A cell-permeable flavone that inhibits the activity of 12-lipoxygenase (IC50 = 120 nM) and reverse transcriptase. Protects cortical neurons from β-amyloid induced toxicity. Reduces leukotriene biosynthesis and inhibits the release of lysosomal enzymes. Also inhibits cellular Ca2+ uptake and mobilization, and adjuvant-induced arthritis. Reported to inhibit microsomal lipid peroxidation by forming an iron-baicalein complex. Inhibits topoisomerase II and induces cell death in hepatocellular carcinoma cell lines. Potentiates contractile responses to nerve stimulation. Inhibits protein tyrosine kinase and PMA-stimulated protein kinase C |
| Camptothecin, *Camptotheca acuminata* | A cell-permeable DNA topoisomerase I inhibitor. Exhibits anti-leukemic and antitumor properties. Induces apoptosis in HL-60 cells and mouse thymocytes. Arrests cells at the G2/M phase |
| Diisopropylfluorophosphate | serine protease inhibitor |
| Phenylmethylsulfonyl Fluoride (PMSF) | Irreversible inhibitor of serine proteases. Its mechanism of action is analogous to that of diisopropylfluorophosphate. PMSF causes sulfonylation of the active-site serine residues. Also reported to inhibit internucleosomal DNA fragmentation in immature thymocytes. For a related, more stable inhibitor, see AEBSF |
| (−)-Huperzine A | An inhibitor of AChE. Antagonist of NMDA receptors. Protects against glutamate-mediated excitotoxicity. |
| Razoxane | Inhibits topoisomerase II without inducing DNA strand breaks (topo II catalytic inhibitor). |
| Suptopin-2 | Suppressor of topoisomerase II inhibition. Reverses cell cycle arrest; bypass of checkpoint function. Has inherent fluorescence and a distinct advantage in identification of molecule targets; effective concentraion in the μM range. |

3. Enzymes
3.1. Caspases

| | |
|---|---|
| Apoptosis Inhibitor; 2-(p-Methoxybenzyl)-3,4-pyrrolidinediol-3-acetate | Effects attributable to the inhibition of caspase-3 activation |

TABLE 1-continued

Overview of apoptosis inhibitors

| Apoptosis inhibitor | Description |
|---|---|
| cIAP-1, Human, Recombinant, E. coli | Recombinant, human cIAP-1 (amino acids 1-618) fused to the peptide sequence MATVIDH10SSNG at the N-terminus and expressed in E. coli. cIAP is a member of the inhibitor of apoptosis family of proteins that inhibits proteolytic activity of mature caspases by interaction of the BIR domain with the active caspase |
| CrmA, Recombinant | CrmA (cowpox viral serpin cytokine response modifier A) is purified from E. coli transformed with a construct containing the full-length coding region of the CrmA gene and 7 additional amino acids that do not affect the activity. CrmA is a natural inhibitor of human caspase-1 and granzyme B, enzymes that are involved in apoptosis |
| Group III Caspase Inhibitor I Peptide sequence: Ac-Ile-Glu-Pro-Asp-CHO, Ac-IEPD-CHO (SEQ ID NO: 3), Caspase-8 inhibitor III | A potent, cell-permeable, and irreversible inhibitor of Group III caspases (caspase-6, -8, -9, and -10), although more effective towards caspases-6 and -8. Also inhibits caspase-1 and caspase-3. When using with purified native or recombinant enzyme, pretreatment with an esterase is required. |
| Kaempferol | A cell-permeable phytoestrogen that inhibits topoisomerase I-catalyzed DNA religation in HL-60 cells. Offers protection against Aβ25-35-induced cell death in neonatal cortical neurons. Its protective effects are comparable to that of estradiol. Blocks the Aβ-induced activation of caspase-2, -3, -8, and -9, and reduces NMDA-induced neuronal apoptosis. Reported to be a potent inhibitor of monoamine oxidases. Acts as an inhibitor of COX-1 activity (IC50 = 180 μM), and of transcriptional activation of COX-2 (IC50 < 15 μM |
| Q-VD-OPH | General, Pancaspase |
| Boc-D(OMe)-FMK | General, Pancaspase |
| Z-D(OMe)E(OMe)VD(OMe)-FMK (SEQ ID NO: 4) | Caspase 3, 7 |
| Z-LE(OMe)TD(OMe)-FMK (SEQ ID NO: 5) | Caspase 8 |
| Z-YVAD(OMe)-FMK (SEQ ID NO: 6) | Caspase 1, 4 |
| Z-FA-FMK | Inhibits Cathepsin B |
| Z-FF-FMK | Cathepsin B, L |
| Mu-PheHphe-FMK | Cathepsin B, L |
| Z-AE(OMe)VD(OMe)-FMK (SEQ ID NO: 7) | Caspase 10 |
| Z-ATAD(OMe)-FMK (SEQ ID NO: 8) | Caspase 12 |
| Z-VK(Biotin)-D(OMe)-FMK | General Caspase |
| Z-LE(OMe)VD(OMe)-FMK (SEQ ID NO: 9) | Caspase 4 |
| Z-VAM-FMK | Antiviral peptide inhibitor, Inhibits HRV2 and HRV14 |
| 4'-Azidocytidine | HCV Inhibitor |
| Caspase-13 Inhibitor I Peptide sequence: Ac-Leu-Glu-Glu-Asp-CHO (SEQ ID NO: 10) | A potent, reversible inhibitor of caspase-13 (ERICE). |
| Caspase-13 Inhibitor II Peptide sequence: Z-Leu-Glu(OMe)-Glu(OMe)-Asp(OMe)-FMK (SEQ ID NO: 11) | A cell-permeable, irreversible inhibitor of caspase-13. When using with purified native or recombinant enzyme, pretreatment with an esterase is required. |
| Caspase-1 Inhibitor I Peptide sequence: Ac-Tyr-Val-Ala-Asp-CHO (SEQ ID NO: 12) | A potent, specific, and reversible inhibitor of caspase-1 (Ki = 200 pM for human recombinant caspase-1), caspase-4, and caspase-5. Strongly inhibits anti-APO-1 induced apoptosis in L929-APO-1 cells. |
| Caspase-1 Inhibitor I, Cell-Permeable Peptide sequence: Ac-Ala-Ala-Val-Ala-Leu-Leu-Pro-Ala-Val-Leu-Leu-Ala-Leu-Leu-Ala-Pro-Tyr-Val-Ala-Asp-CHO (SEQ ID NO: 13) | A cell-permeable inhibitor of caspase-1 (ICE; Interleukin-1β Converting Enzyme), caspase-4, and caspase-5. The C-terminal YVAD-CHO sequence of this peptide is a highly specific, potent, and reversible inhibitor of caspase-1 (Ki = 1 nM). The N-terminal sequence (amino acid residues 1-16) corresponds to the hydrophobic region (h-region) of the signal peptide of the Kaposi fibroblast growth factor (K-FGF) and confers cell-permeability to the peptide |
| Caspase-1 Inhibitor II Peptide sequence: Ac-Tyr-Val-Ala-Asp-CMK (SEQ ID NO: 14) | A cell-permeable and irreversible inhibitor of caspase-1 (Ki = 760 pM), caspase-4, and caspase-5. Inhibits Fas-mediated apoptosis and acidic sphingomyelinase activation |
| Caspase-1 Inhibitor IV Peptide sequence: Ac-Tyr-Val-Ala-Asp-AOM (AOM = 2,6-dimethylbenzoyloxymethyl ketone) (SEQ ID NO: 15) | A highly selective, competitive, cell-permeable, and irreversible inhibitor of caspase-1, caspase-4, and caspase-5. Inactivates the enzyme with a rate limited by diffusion and is relatively inert toward other bionucleophiles such as glutathione, making it an excellent candidate for in vivo studies of enzyme inhibition |

TABLE 1-continued

Overview of apoptosis inhibitors

| Apoptosis inhibitor | Description |
|---|---|
| Caspase-1 Inhibitor V<br>Peptide sequence:<br>Z-Asp-CH2-DCB | A potent inhibitor of caspase-1-like proteases. Blocks apoptotic cell death in human myeloid leukemia U937 cells and blocks etoposide-induced DNA fragmentation |
| Caspase-1 Inhibitor VI<br>Peptide sequence:<br>Z-Tyr-Val-Ala-Asp(OMe)—CH2F*<br>(SEQ ID NO: 16) | A potent, cell-permeable, and irreversible inhibitor of caspase-1 (ICE), caspase-4, and caspase-5 |
| Caspase-2 Inhibitor I<br>Peptide sequence:<br>Z-Val-Asp(OMe)-Val-Ala-Asp(OMe)—CH2F*<br>(SEQ ID NO: 17) | A cell-permeable and irreversible inhibitor of caspase-2 (ICH-1 |
| Caspase-2 Inhibitor II<br>Peptide sequence:<br>Ac-Leu-Asp-Glu-Ser-Asp-CHO<br>(SEQ ID NO: 18) | A reversible inhibitor of caspase-2 and caspase-3 |
| Caspase-3/7 Inhibitor I<br>Peptide sequence:<br>5-[(S)-(+)-2-(Methoxy-methyl)pyrrolidino]sulfonylisatin | A potent, cell-permeable, and specific, reversible inhibitor of caspase-3 (Ki = 60 nM) and caspase-7 (Ki = 170 nM). |
| Caspase-3 Inhibitor I<br>Peptide sequence:<br>Ac-Asp-Glu-Val-Asp-CHO<br>(SEQ ID NO: 19) | A very potent, specific, and reversible inhibitor of caspase-3 (IC50 = 200 pM), caspase-6, caspase-7, caspase-8, and caspase-10. |
| Caspase-3 Inhibitor I, Cell-Permeable<br>Peptide sequence:<br>Ac-Ala-Ala-Val-Ala-Leu-Leu-Pro-Ala-Val-Leu-Leu-Ala-Leu-Leu-Ala-Pro-Asp-Glu-Val-Asp-CHO (SEQ ID NO: 20) | A cell-permeable inhibitor of caspase-3, as well as caspase-6, caspase-7, caspase-8, and caspase-10. The C-terminal DEVD-CHO sequence of this peptide is a highly specific, potent, and reversible inhibitor of caspase-3 (Ki < 1 nM) that has also been shown to strongly inhibit PARP cleavage in cultured human osteosarcoma cell extracts (IC50 = 200 pM). The N-terminal sequence (amino acid residues 1-16) corresponds to the hydrophobic region (h-region) of the signal peptide of Kaposi fibroblast growth factor (K-FGF) and confers cell-permeability to the peptide. A 5 mM (1 mg/100 μl) solution of Caspase-3 Inhibitor I, Cell-permeable (Cat. No. 235427) in DMSO is also available. |
| Caspase-3 Inhibitor II<br>Peptide sequence:<br>Z-Asp(OCH3)-Glu(OCH3)-Val-Asp(OCH3)-FMK<br>(SEQ ID NO: 21) | A potent, cell-permeable, and irreversible inhibitor of caspase-3 as well as caspase-6, caspase-7, caspase-8, and caspase-10. When using with purified native or recombinant enzyme, pretreatment with an esterase is required. A 5 mM (250 μg/75 μl) solution of Z-DEVD-FMK (Cat. No. 264156) in DMSO is also available |
| Caspase-3 Inhibitor III<br>Peptide sequence:<br>Ac-Asp-Glu-Val-Asp-CMK<br>(SEQ ID NO: 22) | A potent, cell-permeable, and irreversible inhibitor of caspase-3 as well as caspase-6, caspase-7, caspase-8, and caspase-10 |
| Caspase-3 Inhibitor IV<br>Peptide sequence.<br>Ac-Asp-Met-Gln-Asp-CHO<br>(SEQ ID NO: 23) | A specific inhibitor of caspase-3. This tetrapeptide inhibitor has been used with the caspase-6 inhibitor Ac-VEID-CHO to dissect the pathway of caspase activation in Fas-stimulated Jurkat cells |
| Caspase-3 Inhibitor V<br>Peptide sequence:<br>Z-Asp(OMe)-Gln-Met-Asp(OMe)—CH2F*<br>(SEQ ID NO: 24) | A potent, cell-permeable, and irreversible inhibitor of caspase-3, also recognizes caspase-1. When using with purified native or recombinant enzyme, pre-treatment with an esterase is required |
| Caspase-3 Inhibitor VII<br>Peptide sequence:<br>2-(4-Methyl-8-(morpholin-4-ylsulfonyl)-1,3-dioxo-1,3-dihydro-2H-pyrrolo[3,4-c]quinolin-2-yl)ethyl acetate | A cell-permeable, non-peptidyl pyrroloquinoline compound that acts as a potent, reversible, and non-competitive inhibitor of caspase-3 (IC50 = 23 nM) with 10-100-fold greater selectivity. Shown to display higher anti-apoptotic activity than Z-VAD-FMK (Cat. No. 627610) in a model of Staurosporine- (Cat. No. 569397) induced apoptosis in human Jurkat T cells. |
| Caspase-4 Inhibitor I<br>Peptide sequence:<br>Ac-Leu-Glu-Val-Asp-CHO<br>(SEQ ID NO: 25) | A reversible caspase-4 inhibitor |
| Caspase-4 Inhibitor I, Cell-Permeable<br>Peptide sequence:<br>Ac-Ala-Ala-Val-Ala-Leu-Leu-Pro-Ala-Val-Leu-Leu-Ala-Leu-Leu-Ala-Pro-Leu-Glu-Val-Asp-CHO (SEQ ID NO: 26) | A potent, cell-permeable, and reversible inhibitor of caspase-4. The N-terminal sequence (amino acid residues 1-16) corresponds to the hydrophobic region of the signal peptide of Kaposi fibroblast growth factor and confers cell permeability to the peptide. |
| Caspase-5 Inhibitor I<br>Peptide sequence:<br>Z-Trp-Glu(OMe)-His-Asp(OMe)—CH2F*<br>(SEQ ID NO: 27) | A potent, cell-permeable, and irreversible inhibitor of caspase-5. Strongly inhibits caspase-1. Also inhibits caspase-4 and caspase-8 |

TABLE 1-continued

Overview of apoptosis inhibitors

| Apoptosis inhibitor | Description |
|---|---|
| Caspase-6 Inhibitor I<br>Peptide sequence:<br>Z-Val-Glu(OMe)-Ile-Asp(OMe)—CH2F*<br>(SEQ ID NO: 28) | A cell-permeable, irreversible inhibitor of caspase-6. When using with purified native or recombinant enzyme, pretreatment with an esterase is required |
| Caspase-6 Inhibitor II, Cell-Permeable<br>Peptide sequence:<br>Ac-Ala-Ala-Val-Ala-Leu-Leu-Pro-Ala-Val-Leu-Leu-Ala-Leu-Leu-Ala-Pro-Val-Glu-Ile-Asp-CHO (SEQ ID NO: 29) | A potent, cell-permeable, and reversible inhibitor of caspase-6. The N-terminal sequence (amino acids 1-16) corresponds to the hydrophobic region of the signal peptide of Kaposi fibroblast growth factor and confers cell permeability to the peptide |
| Caspase-8 Inhibitor I, Cell-Permeable<br>Peptide sequence:<br>Ac-Ala-Ala-Val-Ala-Leu-Leu-Pro-Ala-Val-Leu-Leu-Ala-Leu-Leu-Ala-Pro-Ile-Glu-Thr-Asp-CHO (SEQ ID NO: 30) | A potent, cell-permeable, and reversible inhibitor of caspase-8 and Granzyme B. The N-terminal sequence (amino acids 1-16) corresponds to the hydrophobic region of the signal peptide of Kaposi fibroblast growth factor and confers cell permeability to the peptide |
| Caspase-8 Inhibitor II<br>Peptide sequence:<br>Z-Ile-Glu(OMe)-Thr-Asp(OMe)—CH2F*<br>(SEQ ID NO: 31) | A potent, cell-permeable, and irreversible inhibitor of caspase-8 and granzyme B. Effectively inhibits influenza virus-induced apoptosis in HeLa cells. Also inhibits granzyme B. When using with purified native or recombinant enzyme, pretreatment with an esterase is required. A 5 mM (250 μg/76 μl) solution of Z-IETD-FMK (Cat. No. 218840) in DMSO is also available. |
| Caspase-9 Inhibitor I<br>Peptide sequence:<br>Z-Leu-Glu(OMe)-His-Asp(OMe)—CH2F*<br>(SEQ ID NO: 32) | A potent, cell-permeable, and irreversible inhibitor of caspase-9. May also inhibit caspase-4 and caspase-5. When using with purified native or recombinant enzyme, pretreatment with an esterase is required. A 5 mM (250 μg/72 μl) solution of Z-LEHD-FMK (Cat. No. 218841) in DMSO is also available |
| Caspase-9 Inhibitor II, Cell-Permeable<br>Peptide sequence:<br>Ac-Ala-Ala-Val-Ala-Leu-Leu-Pro-Ala-Val-Leu-Leu-Ala-Leu-Leu-Ala-Pro-Leu-Glu-His-Asp-CHO (SEQ ID NO: 33) | A potent, cell-permeable, and reversible inhibitor of caspase-9. May also inhibit caspase-4 and caspase-5. The N-terminal sequence (amino acids 1-16) corresponds to the hydrophobic region of the signal peptide of Kaposi fibroblast growth factor and confers cell permeability to the peptide |
| Caspase-9 Inhibitor III<br>Peptide sequence:<br>Ac-Leu-Glu-His-Asp-CMK<br>(SEQ ID NO: 34) | A potent, irreversible inhibitor of caspase-9. Reported to reduce myocardial infarct size during reperfusion (~70 nM). |
| Caspase Inhibitor I<br>Peptide sequence:<br>Z-Val-Ala-Asp(OMe)—CH2F* | A cell-permeable, irreversible, pan-caspase inhibitor. Inhibits Fas-mediated apoptosis in Jurkat cells and staurosporine-induced cell death in corneal epithelial cells. When using with purified native or recombinant enzyme, pre-treatment with an esterase is required. |
| Caspase Inhibitor II<br>Peptide sequence:<br>Ac-Val-Ala-Asp-CHO | A potent and reversible pan-caspase inhibitor. |
| Caspase Inhibitor II, Cell-Permeable<br>Peptide sequence:<br>Ac-Ala-Ala-Val-Ala-Leu-Leu-Pro-Ala-Val-Leu-Leu-Ala-Leu-Leu-Ala-Pro-Val-Ala-Asp-CHO<br>(SEQ ID NO: 35) | A cell-permeable, reversible pan-caspase inhibitor produced by attaching the N-terminal sequence (amino acids 1-16) of the Kaposi fibroblast growth factor signaling peptide, which imparts cell-permeability to VAD peptide. |
| Caspase Inhibitor III<br>Peptide sequence:<br>Boc-Asp(OMe)—CH2F* | A cell-permeable, irreversible, broad-spectrum caspase inhibitor. |
| Caspase Inhibitor IV<br>Peptide sequence:<br>Boc-Asp(OBzl)-CMK | A general, irreversible caspase inhibitor. |
| Caspase Inhibitor VI<br>Peptide sequence:<br>Z-Val-Ala-Asp-CH2F* | An irreversible general caspase inhibitor. Useful for studies involving recombinant, isolated, and purified caspase enzymes. Unlike Caspase Inhibitor I (Cat. No. 627610), this inhibitor does not require pretreatment with esterase for in vitro studies. A 10 mM (1 mg/221 μl) solution of Caspase Inhibitor VI (Cat. No. 219011) in DMSO is also available |
| Caspase Inhibitor VIII<br>Peptide sequence:<br>Ac-Val-Asp-Val-Ala-Asp-CHO<br>(SEQ ID NO: 36) | A potent, reversible inhibitor of caspase-2 (Ki = 3.5 nM), caspase-3 (Ki = 1 nM) and caspase-7 (Ki = 7.5 nM). Also serves as an inhibitor of DRONC (*Drosophila* caspase), a glutamate/aspartate protease. |
| Caspase Inhibitor X<br>Peptide sequence:<br>BI-9B12 | A benzodioxane containing 2,4-disubstituted thiazolo compound that acts as a selective, reversible and competitive inhibitor of caspases (Ki = 4.3 μM, 6.2 μM and 2.7 μM for caspase-3, -7 and -8, respectively). The benzodioxane moiety is shown to fit in the 'aspartate hole' of the caspases and possibly disrupt caspase-8 |

TABLE 1-continued

Overview of apoptosis inhibitors

| Apoptosis inhibitor | Description |
|---|---|
| Caspase-1 Inhibitors | assisted cleavage of BID, a proapoptotic protein. Weakly affects the activity of anthrax lethal factor, a metalloprotease, at ~20 μM Including, but not limited to Ac-N-Me-Tyr-Val-Ala-Asp-aldehyde (pseudo acid) (SEQ ID NO: 37) Ac-Trp-Glu-His-Asp-aldehyde (pseudo acid) (SEQ ID NO: 38) Ac-Tyr-Val-Ala-Asp-aldehyde (pseudo acid) (SEQ ID NO: 39) Ac-Tyr-Val-Ala-Asp-chloromethylketone (SEQ ID NO: 40) Ac-Tyr-Val-Ala-Asp-2,6-dimethylbenzoyloxymethylketone (SEQ ID NO: 41) Ac-Tyr-Val-Ala-Asp(OtBu)-aldehyde-dimethyl acetal (SEQ ID NO: 42) Ac-Tyr-Val-Lys-Asp-aldehyde (pseudo acid) (SEQ ID NO: 43) Ac-Tyr-Val-Lys(biotinyl)-Asp-2,6-dimethylbenzoyloxymethylketone Biotinyl-Tyr-Val-Ala-Asp-chloromethylketone Biotinyl-Val-Ala-DL-Asp-fluoromethylketone Fluorescein-6-carbonyl-Tyr-Val-Ala-DL-Asp(OMe)-fluoromethylketone Fluorescein-6-carbonyl-Val-Ala-DL-Asp(OMe)-fluoromethylketone Z-Asp-2,6-dichlorobenzoyloxymethylketone Z-Tyr-Val-Ala-Asp-chloromethylketone Z-Val-Ala-DL-Asp-fluoromethylketone Z-Val-Ala-DL-Asp(OMe)-fluoromethylketone |
| Caspase-2 Inhibitors | Including, but not limited to Ac-Val-Asp-Val-Ala-Asp-aldehyde (pseudo acid) (SEQ ID NO: 44) Fluorescein-6-carbonyl-Val-Asp(OMe)-Val-Ala-DL-Asp(OMe)-fluoromethylketone (SEQ ID NO: 45) Z-Val-Asp(OMe)-Val-Ala-DL-Asp(OMe)-fluoromethylketone |
| Caspase-3 Precursor Protease Inhibitors | Including, but not limited to Ac-Glu-Ser-Met-Asp-aldehyde (pseudo acid) (SEQ ID NO: 46) Ac-Ile-Glu-Thr-Asp-aldehyde (pseudo acid) (SEQ ID NO: 47) |
| Caspase-3 Inhibitors | Including, but not limited to Ac-Asp-Glu-Val-Asp-aldehyde (pseudo acid) (SEQ ID NO: 48) Ac-Asp-Met-Gln-Asp-aldehyde (pseudo acid) (SEQ ID NO: 49) Biotinyl-Asp-Glu-Val-Asp-aldehyde (pseudo acid) Caspase-3/7 Inhibitor II Fluorescein-6-carbonyl-Asp(OMe)-Glu(OMe)-Val-DL-Asp(OMe)-fluoromethylketone Z-Asp(OMe)-Gln-Met-DL-Asp(OMe)-fluoromethylketone (SEQ ID NO: 50) Z-Asp-Glu-Val-Asp-chloromethylketone (SEQ ID NO: 51) Z-Asp(OMe)-Glu(OMe)-Val-DL-Asp(OMe)-fluoromethylketone (SEQ ID NO: 52) |
| Caspase-4 Inhibitors | Including, but not limited to Ac-Leu-Glu-Val-Asp-aldehyde (pseudo acid) (SEQ ID NO: 53) Z-Tyr-Val-Ala-DL-Asp-fluoromethylketone (SEQ ID NO: 54) |
| Caspase-6 Inhibitors | Including, but not limited to Ac-Val-Glu-Ile-Asp-aldehyde (pseudo acid) (SEQ ID NO: 55) Fluorescein-6-carbonyl-Val-Glu(OMe)-Ile-DL-Asp(OMe)-fluoromethylketone (SEQ ID NO: 56) Z-Val-Glu(OMe)-Ile-DL-Asp(OMe)-fluoromethylketone |
| Caspase-8 Inhibitors | Including, but not limited to Ac-Ile-Glu-Pro-Asp-aldehyde (pseudo acid) (SEQ ID NO: 57) Boc-Ala-Glu-Val-Asp-aldehyde (pseudo acid) (SEQ ID NO: 58) Fluorescein-6-carbonyl-Ile-Glu(OMe)-Thr-DL-Asp(OMe)-fluoromethylketone (SEQ ID NO: 59) Fluorescein-6-carbonyl-Leu-Glu(OMe)-Thr-DL-Asp(OMe)-fluoromethylketone (SEQ ID NO: 60) Z-Ile-Glu(OMe)-Thr-DL-Asp(OMe)-fluoromethylketone Z-Leu-Glu(OMe)-Thr-DL-Asp(OMe)-fluoromethylketone Z-LE(OMe)TD(OMe)-FMK |
| Caspase-9 Inhibitors | Including, but not limited to Ac-Leu-Glu-His-Asp-aldehyde (pseudo acid) (SEQ ID NO: 61) Ac-Leu-Glu-His-Asp-chloromethylketone (SEQ ID NO: 62) Fluorescein-6-carbonyl-Leu-Glu(OMe)-His-DL-Asp(OMe)-fluoromethylketone |
| Caspase-10 Inhibitors | Including, but not limited to Fluorescein-6-carbonyl-Ala-Glu(OMe)-Val-DL-Asp(OMe)-fluoromethylketone Z-Ala-Glu-Val-DL-Asp-fluoromethylketone (SEQ ID NO: 63) |

3.2. Calpain

| | |
|---|---|
| Calpain Inhibitor III Peptide sequence: Z-Val-Phe—CHO | A potent, cell-permeable inhibitor of calpain I and II (Ki = 8 nM). Reduces capsaicin-mediated cell death in cultured dorsal root ganglion. Reported to block A23187-induced suppression of neurite outgrowth in isolated hippocampal pyramidal neurons. Exhibits neuroprotective effect in glutamate-induced toxicity. |

TABLE 1-continued

Overview of apoptosis inhibitors

| Apoptosis inhibitor | Description |
|---|---|
| Calpain Inhibitor IV<br>Peptide sequence:<br>Z-Leu-Leu-Tyr-CH2F | A potent, cell-permeable, and irreversible inhibitor of calpain II (k2 = 28,900 M–1s–1). Also acts as an inhibitor of cathepsin L (k2 = 680,000 M–1s–1). |
| Calpain Inhibitor V<br>Peptide sequence:<br>Mu-Val-HPh—CH2F<br>(Mu = morpholinoureidyl;<br>HPh = homophenylalanyl) | A potent, cell-permeable, and irreversible inhibitor of calpain |
| Ac-Leu-Leu-Nle-al | Cell-permeable, peptide aldehyde inhibitor of calpain I (Ki = 190 nM), calpain II (Ki = 150 nM), cathepsin L (Ki = 0.5 nM) and other neutral cysteine proteases. Inhibits cell cycle progression at G1/S and metaphase/anaphase in CHO cells by inhibiting cyclin B degradation. Also stimulates HMG-CoA synthase transcription by inhibiting degradation of active SREBP-1 (sterol regulatory element-binding protein 1). Protects against neuronal damage caused by hypoxia and ischemia. Inhibits apoptosis in thymocytes and metamyelocytes. Also prevents nitric oxide production by activated macrophages by interfering with the transcription of inducible nitric oxide synthase (iNOS; NOS II). Inhibits proteolytic degradation of IkBalpha and IkBβ in RAW macrophages induced with LPS. It also prolong association of MHC class I molecules with the transporters associated with antigen processing |
| Z-LLY-FMK | Calpain |
| N-Acetyl-Leu-Leu-Met | Calpain I |
| N-Acetyl-Leu-Leu-Nle-CHO | Calpain I |

3.3. others

| | |
|---|---|
| BAPTA/AM | Membrane-permeable form of BAPTA. Can be loaded into a wide variety of cells, where it is hydrolyzed by cytosolic esterases and is trapped intracellularly as the active chelator BAPTA. Prevents cocaine-induced ventricular fibrillations. Abolishes vitamin D3-induced increase in intracellular Ca2+. Induces inactivation of protein kinase C. Also inhibits thapsigargin-induced apoptosis in rat thymocytes. |
| Granzyme B Inhibitor I<br>Peptide sequence:<br>Z-Ala-Ala-Asp-CH2Cl<br>(SEQ ID NO: 64) | A weak inhibitor of the human and murine granzyme B. Also inhibits the apoptosis-related DNA fragmentation in lymphocytes by fragmentin 2, a rat lymphocyte granule protease homologous to granzyme B (ID50 = 300 nM). |
| Granzyme B Inhibitor II<br>Peptide sequence:<br>Ac-Ile-Glu-Thr-Asp-CHO<br>(SEQ ID NO: 65) | A potent, reversible inhibitor of granzyme B and caspase-8 (Ki = 1 nM). Also inhibits caspase-1 (<6 nM), caspase-6 (5.6 nM), and caspase-10 (27 nM). |
| Granzyme B Inhibitor IV<br>Peptide sequence:<br>Ac-Ile-Glu-Pro-Asp-CHO | A reversible inhibitor of granzyme B and caspase-8 |
| Leupeptin, Hemisulfate, Microbial | A reversible inhibitor of trypsin-like proteases and cysteine proteases. Also known to inhibit activation-induced programmed cell death and to restore defective immune responses of HIV+ donors |
| N-Ethylmaleimide | Sulfhydryl alkylating reagent that inhibits H+-ATPase and suppresses the short circuit current (IC50 = 22 μM) in pancreatic duct cells. Inactivates NADP-dependent isocitrate dehydrogenase. Also a potent inhibitor of both Mg2+ and Ca2+/Mg2+-stimulated DNA fragmentation in rat liver nuclei. Stimulates arachidonic acid release through activation of PLA2 in endothelial cells |
| Nα-Tosyl-Lys Chloromethyl Ketone, Hydrochloride (TLCK) | Inhibits trypsin-like serine proteinases. Irreversibly inactivates trypsin without affecting chymotrypsin. Prevents nitric oxide production by activated macrophages by interfering with transcription of the iNOS gene. Blocks cell-cell adhesion and binding of HIV-1 virus to the target cells. In macrophages, blocks nitric oxide synthase induced by interferon-γ and lipopolysaccharides (EC50 = 80 μM). Prevents endonucleolysis accompanying apoptotic death of HL-60 leukemia cells and normal thymocytes |
| Omi/HtrA2 Protease Inhibitor, Ucf-101 | A cell-permeable furfurylidine-thiobarbituric acid compound that acts as a potent, specific, competitive, and reversible inhibitor of the pro-apoptotic, heat-inducible, mitochondrial serine protease Omi/HtrA2 (IC50 = 9.5 μM for His-Omi134-458). Shows very little activity against various other serine proteases tested (IC50 ≥ 200 μM). Reported to block Omi/HtrA2 induced cell death in caspase-9 (–/–) null fibroblasts. |
| Phenylarsine Oxide | A membrane-permeable protein tyrosine phosphatase inhibitor (IC50 = 18 μM). Stimulates 2-deoxyglucose transport in insulin-resistant human skeletal muscle and activates p56lck protein tyrosine kinase. Blocks TNF-α-dependent activation of NF-κB in human myeloid ML-1a cells. PAO inhibits the protease activities of |

TABLE 1-continued

Overview of apoptosis inhibitors

| Apoptosis inhibitor | Description |
|---|---|
| | recombinant human caspases as well as endogenous caspases that are active in extracts of pre-apoptotic chicken DU249 cells (S/M extracts). |
| Phorbol-12,13-dibutyrate | Strong irritant for mouse skin, but only moderately active as a tumor promoter. Activates protein kinase C. Stimulates the phosphorylation of Na+, K+-ATPase, thereby inhibiting its activity. Promotes the expression of inducible NOS in cultured hepatocytes. Commonly used in binding studies or in applications requiring high concentrations of phorbol compounds. |
| Hypericin | Inhibits PKC, CKII, MAP Kinase, Insulin R, EGFR, PI-3 Kinase and also noted to possess antiviral activity. |
| Butyrolactone I | A cell-permeable and highly selective inhibitor of cyclin-dependent protein kinases (Cdks) that inhibits cell cycle progression at the G1/S and G2/M transitions. Inhibits p34cdk1/cyclinB (Cdk1; IC50 = 680 nM). Also selectively inhibits Cdk2 and Cdk5 kinases. Has little effect on casein kinase I, casein kinase II, EGF receptor kinase, MAP kinase, PKA, and PKC. Shown to prevent the phosphorylation of retinoblastoma protein and H1 histone. Also blocks Fas-induced apoptosis in HL-60 cells and shows antitumor effects on human lung cancer cell lines |
| Nilotinib | Spezifischer BCR-ABL-Tyrosinkinase-Inhibitor |
| Quercetin(Sophoretin) | Quercetin is a PI3K and PKC inhibitor with IC50 of 3.8 µM and 15 µg/ml. It strongly abrogated PI3K and Src kinases, mildly inhibited Akt1/2, and slightly affected PKC, p38 and ERK1/2. [1][2] Quercetin is a naturally-occurring polar auxin transport inhibitor with IC50 of 0.8, 16.7, 6.1, 11.36 µM for the inhibition of LDH % release, the inhibition of TNF-induced PMN-EC adhesion, TNF-induced inhibition of DNA synthesis and proliferation. It is a type of plant-based chemical, or phytochemical, known as a flavonol and a plant-derived flavonoid found in fruits, vegetables, leaves and grains. It also may be used as an ingredient in supplements, beverages or foods. In several studies, it may have anti-inflammatory and antioxidant properties, and it is being investigated for a wide range of potential health benefits |

EXAMPLES

In the following examples, materials and methods of the present invention are provided. It should be understood that these examples are for illustrative purpose only and are not to be construed as limiting this invention in any manner.

I. Materials and Methods

A test system was designed, wherein cell-containing biological samples, here whole blood samples, were incubated at room temperature (RT) for up to 6 or 7 days. Therein, the sample stabilizing properties of the additives of the present invention were tested on day 0, day 3 and day 6/7 the samples. The samples were processed according to the following protocols, where applicable (for details, see also the specific examples in the results section):

1. Measurement of Blood Cell Integrity by Fluorescence Activated Cell Sorting (FACS)

1.1. Lysis of Red Blood Cells

Transfer of 2 ml blood sample into a fresh 15 ml Falcon tube
Addition of 5-fold Buffer EL (QIAGEN)
Inverting of the sample (10×)
Incubation on ice (10 min.)
Centrifugation for 10 min. @400×g and 4° C.
Discard of the supernatant
Addition of 2-fold Buffer EL (QIAGEN) to the white blood cell pellet
Resolution of the pellet in Buffer EL (QIAGEN) by slight vortexing
Centrifugation for 10 min @ 400×g
Discard of the supernatant
Addition of 500 µl FACS Flow (Becton, Dickinson Plymouth, UK) to the white blood cell pellet
Resolution of the pellet in FACS Flow by slight vortexing
Transfer of 1 ml FACS Flow into a fresh FACS tube
Transfer of 100 µl of the resolved pellet into a FACS tube
Red blood cells are lysed because otherwise, the decisive cell populations (which can release e.g. genomic DNA) are not distinguishable in the FACS analysis due to the high amount of red blood cells.

1.2. Measurement of Cell Integrity by Flow Cytometry

The measurement was performed according to manufacturer's instruction (FACSCalibur; Becton, Dickinson Plymouth, UK).

2. Separation of Blood Plasma

To separate the blood plasma from the whole blood, the blood samples were centrifuged for 15 min at 5000 rpm, and the obtained plasma samples were again centrifuged for 10 min at 16.000×g at 4° C.

The resulting blood plasma was used for isolating the nucleic acids contained therein.

3. Nucleic Acid Purification

The circulating, extracellular nucleic acids were purified from the obtained plasma samples using the QIAamp® Circulating NA Kit (according to the handbook). In brief:
10 ml sample input;
lysis: 1 ml Proteinase K and 8 ml Buffer ACL (QIAGEN)
binding: 18 ml Buffer ACB (QIAGEN)
wash-steps: unchanged and according to handbook
elution in 60 µl Buffer AVE (QIAGEN)

4. Analysis of the Eluates

The eluates obtained according to 3. were stored at −20° C. till all samples (including day 6/7 samples) were purified. Afterwards, eluates of the same condition were pooled and treated as follows:

4.1. Measurement of the blood cell stability/DNA release by the determination of DNA size distribution using a chip gel electrophoresis (2100 Bioanalyzer; Agilent Technologies; Inc., USA) according to manufacturer's instruction (see handbook Agilent DNA 7500 and DNA 12000 Kit Guide), but 1.5 µl instead of 1 µl sample were transferred to the wells.

4.2. DNA quantification with a real time PCR assay, sensitive for DNA degradation (target: 500 and 66 bp long ribosomal 18S DNA coding sequences).

The DNA duplex assay was carried out according to the QuantiTect® Multiplex PCR handbook (Qiagen) with the following adaptions:

Primer concentration was up scaled from 8 µM to 16 µM.
Annealing/extension step was extended from 1 to 2 min. (samples were diluted 1:10 before amplification)

4.3. RNA detection using real time PCR assays, sensitive for variations in circulating cell-free RNA levels (target: 18S rRNA, IL8, c-fos and p53). The RNA assays were carried out according to the conditions described in Tables 2 to 4.

TABLE 2 shows compositions of PCR reagents and cycling conditions of the p53 mRNA one step real time PCR.

TaqMan MasterMix (MM)

| component | single reaction | master-mix (x-fold) | c | p53 | FAM-BHQ + HEX-BHQ |
|---|---|---|---|---|---|
| x-fach | 1 x | 182 | 1 x | | 20.00 mastermix/reaction |
| RNA | 5.000 | / | var. | | 5 µl RNA |
| A. dest (PCR grade) | 3.813 | 693.9 | / | | 25.00 µl reaction volume |
| 2x QuantiTect Probe RT-PCR MasterMix (Puffer) | 12.500 | 2275.0 | 1 x | | |
| forw. primer (20 µM) | 0.500 | 91.0 | 400 nM | | |
| rev. primer (20 µM) | 0.500 | 91.0 | 400 nM | | |
| probe (20 µM) | 0.313 | 56.9 | 250 nM | | |
| RNAsin (40 U/µl; Promega) | 0.125 | 22.8 | 0.2 U/µl | | |
| MgCl2 (25 mM) | 2.000 | 364.0 | 6 mM | | |
| QuantiTect RT-PCR Mix (Enzym Mix) | 0.250 | 45.5 | U/µl | | |
| Reaction volume [µl] | 25.000 | 3640.0 | | | |

Cycling:
30 min 50° C.
15 min 95° C.
40 cycles
15 seq. 95° C.

TABLE 3 shows compositions of PCR reagents and cycling conditions of the IL8 mRNA one step real time PCR.

| component | single reaction | master-mix (x-fold) | final konc. | IL8 | FAM-BHQ |
|---|---|---|---|---|---|
| x-fold | 1 x | 106 | 1 x | | 20.00 µl mastermix/reaction |
| RNA | 5.000 | / | var. | | 5 µl RNA |
| A. dest (PCR grade) | 3.751 | 397.6 | / | | 25.00 µl reaction volume |
| 2x QuantiTect Probe RT-PCR MasterMix (Puffer) | 12.500 | 1325.0 | 1 x | | |
| forw. primer (40 µM) | 0.562 | 59.6 | 900 nM | | |
| rev. primer (40 µM) | 0.562 | 59.6 | 900 nM | | |
| probe (20 µM) | 0.250 | 26.5 | 200 nM | | |
| RNAsin (40 U/µl; Promega) | 0.125 | 13.3 | 0.2 U/µl | | |
| MgCl2 (25 mM) | 2.000 | 212.0 | 6 mM | | |
| QuantiTect RT-PCR Mix (Enzym Mix) | 0.250 | 26.5 | U/µl | | |
| Reaction volume [µl] | 25.000 | 2120.0 | | | |

Cycling:
30 min 50° C.
15 min 95° C.
40 cycles
15 seq. 95° C.
1 min. 60° C.

TABLE 4 shows compositions of PCR reagents and cycling conditions
of the c-fos mRNA/18S rRNA duplex real time PCR.

| Chemicals CFOS | for single reaction | MM x-fold | FAM-JOE |
|---|---|---|---|
| x-fold | 1x | 220 | 17.6 μl mastermix/reaction |
| Template | 2.4 | / | 2.4 μl RNA |
| A. dest | 1.00 | 220 | 20 μl reaction volume |
| 2x QuantiTec Mastermix | 10 | 2200 | |
| forw. primer (20 μM); c-fos | 0.900 | 198 | |
| rev. primer (20 μM); c-fos | 0.900 | 198 | |
| probe (10 μM); c-fos | 0.500 | 110 | |
| forw. primer (10 μM); 18 S | 0.800 | 176 | |
| rev. primer (10 μM); 18 S | 0.800 | 176 | |
| probe (10 μM); 18 S | 0.800 | 176 | |
| RNasin (40 U/μl; Promega) | 0.100 | 22 | |
| MgCl2 (25 mM) | 1.6 | 352 | |
| QuantiTect RT-PCR Mix (Enzym Mix) | 0.2 | 44 | |
| reaction volume [μl] | 20.0 | 3872 | |

Cycling:
30 min 50° C.
15 min 95° C.
40 cycles
15 sec. 95° C.
1.30 min. 60° C.

TABLE 5 summarizes the information of the used DNA target sequences detected in 4.2 and 4.3

| target | description | position | amplicon size [bp] | position | sequence 5'-3' | length [nt] | dye |
|---|---|---|---|---|---|---|---|
| 18 S | human ribosomal DNA | p12-region of chromosome 13, 14, 15, 21, 22 | 66 | forward | GCCGCTAGAGGT GAAATTCTTG (SEQ ID NO: 66) | 22 | 5' Cy5-BHQ 3' |
| | | | | reverse | CATTCTTGGCAA ATGCTTTCG (SEQ ID NO: 67) | 21 | |
| | | | | probe | ACCGGCGCAAGA CGGACCAGA (SEQ ID NO: 68) | 21 | |
| 18 S | human ribosomal DNA | p12-region of chromosome 13, 14, 15, 21, 22 | 500 | forward | GTCGCTCGCTCC TCTCCTACTT (SEQ ID NO: 69) | 22 | 5' FAM-BHQ 3' |
| | | | | reverse | GGCTGCTGGCAC CAGACTT (SEQ ID NO: 72) | 19 | |
| | | | | probe | CTAATACATGCC GACGGGCGCTGA C (SEQ ID NO: 71) | 25 | |

II. Performed Experiments and Results

Subsequently, the details on the performed experiments are explained. Details to the methods used in the examples were described above under I.

Example 1

Stabilization by the Addition of a Caspase-Inhibitor

Two different oligopeptides, Q-VD-OPh and Z-Val-Ala-Asp(OMe)-FMK acting as broad spectrum caspase-inhibitors, were tested:

TABLE 6

Tested caspase inhibitors

| inhibitor name | moleculare weight | solubility | structure |
|---|---|---|---|
| Q-VD-OPH | 513.49 | 20 mM, add 97 µl DMSO<br>10 mM, add 194 µl DMSO<br>5 mM, add 388 µl DMSO | 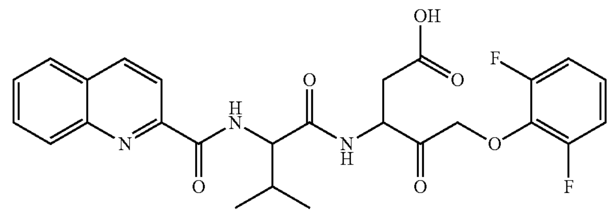 [SMILES: CC(C)C(NC(=O)c1ccc2ccccc2n1)C(=O)NC(CC(=O)O)C(=O)COc1c(F)cccc1F] |
| Z-Val-Ala-Asp(Ome)-FMK | 467.49 | 20 mM, add 107 µl DMSO<br>10 mM, add 214 µl DMSO<br>5 mM, add 428 µl DMSO | 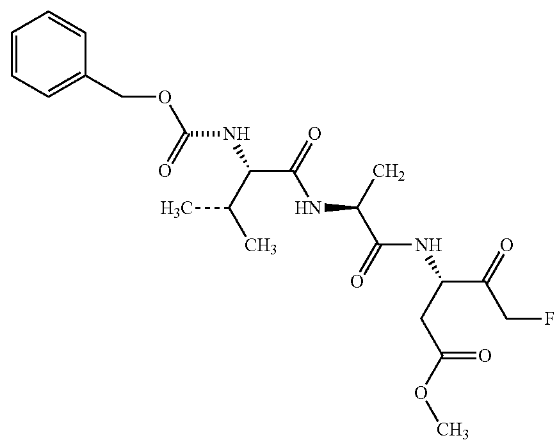 |

Each tested caspase inhibitor was added to whole blood samples (20 µM end concentration in 10 ml blood; blood was collected into Vacutainer K2E Tubes; BD). The whole blood sample was processed as described in section I, see 2. (plasma preparation) and 3. (nucleic acid isolation).

Results of the Chip Gel Electrophoresis

The eluted circulating cell-free DNA was separated by size using chip gel electrophoresis (for details on the method see above, I, 4.1). FIG. 1a shows the obtained results. The DMSO control and the K2E blood (not treated according to the teachings of the present invention) show the same ladder-like pattern of bands. This pattern occurs in samples where apoptosis takes place. During apoptosis, endonucleases degrade genomic DNA at inter-nucleosomal linker regions and produce DNA fragments of circa 180 bp or multiples of 180 bp. Thus, apoptosis occurs in samples which show a clear ladder-like pattern. Furthermore, the strength (darkness) of the pattern is decisive. The darker the bands, the more genomic DNA was released from the cells and thus contaminates the extracellular nucleic acid population.

Figure 1B:
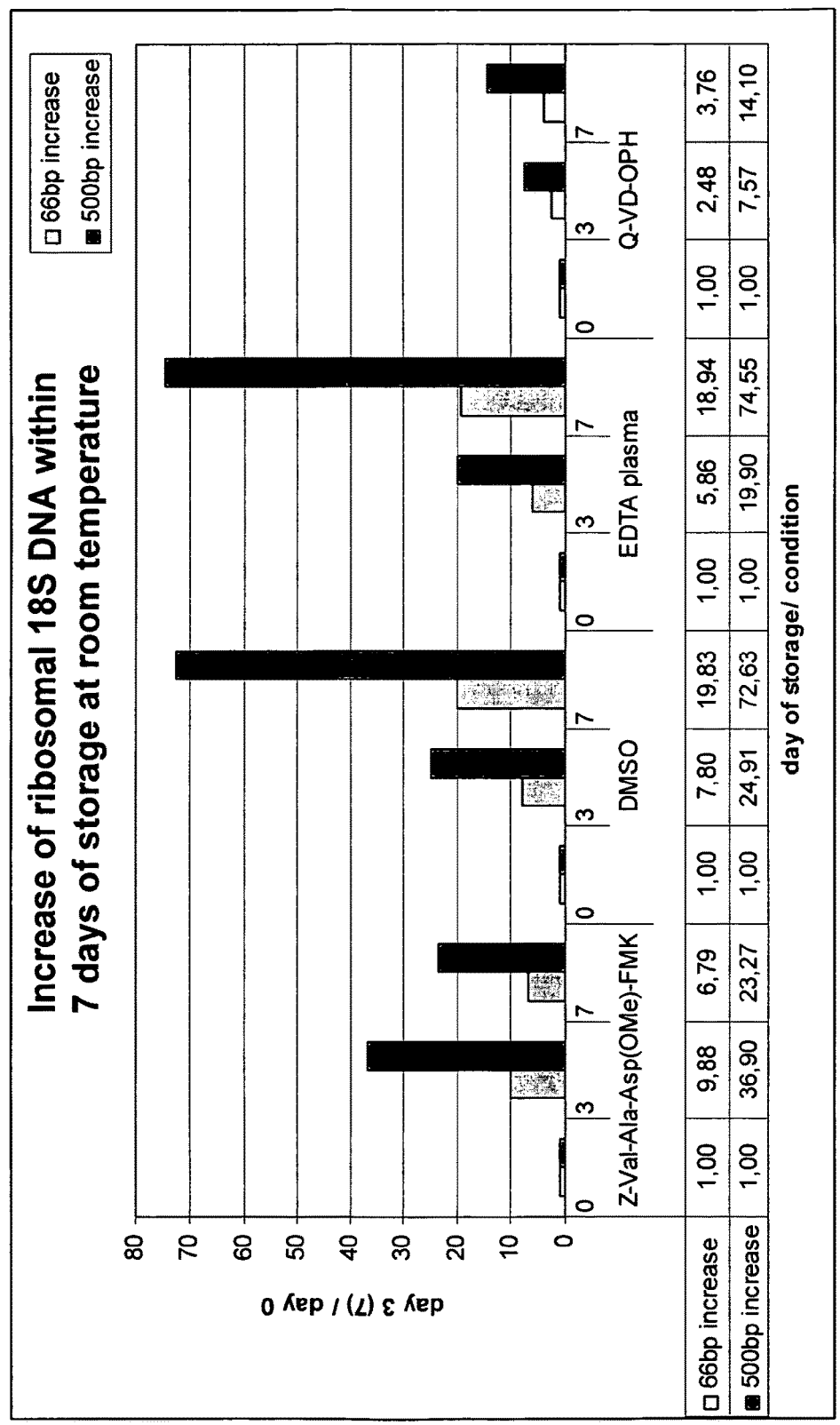
FIG. 1b is a diagram showing the effect of caspase inhibitors on the increase of ribosomal 18S DNA in plasma (Example 1).

FIG. 1 a) shows that the DMSO control and the K2E blood samples show a strong ladder-like pattern already on day 3, which becomes even stronger on day 7. Thus, genomic DNA was released from the cells contained in the sample and was also degraded. This released and degraded DNA contaminates the cell-free nucleic acids contained in the sample. Hence, no acceptable stabilisation is achieved with these samples.

In contrast, whole blood samples treated with Z-Val-Ala-Asp(OMe)-FMK show a reduced ladder-like pattern in particular on day 7 compared to the controls, indicating an inhibition of the release of genomic DNA, respectively genomic DNA fragmentation caused by apoptosis. This effect is confirmed by the results shown in FIG. 1 b) (see below). The effect is even more prominent in the blood samples treated with Q-VD-OPh, which show significantly reduced ladder-like patterns already on day 3 and day 7. Thus, the release and degradation of genomic DNA is effectively prevented, respectively reduced by the addition of the caspase inhibitor Q-VD-OPh.

Results of the DNA Quantification

The eluted circulating cell-free DNA was also quantified with the real time PCR assay that is sensitive for DNA degradation (for details on the method see above, I, 4.2). FIG. 1 b) shows the effect of the tested caspase-inhibitors on the stabilisation of the extracellular nucleic acid population (18S DNA duplex assay) within 7 days of storage at RT, here the increase in DNA.

Detection of ribosomal 18S DNA by quantitative real-time PCR, makes it possible to calculate the x-fold increase of DNA from day 0 to day 3 or 7 (calculation: division of day 3 (or 7) copies by day 0 copies). Surprisingly, the results shown in FIG. 1 b) demonstrate a reduced increase of DNA when a caspase-inhibitor, especially Q-VD-OPh, was added to whole blood samples. The stabilising effect of Z-Val-Ala-Asp(OMe)-FMK compared to the standard samples was more prominent on day 7, thereby confirming the results shown in FIG. 1 a).

SUMMARY

Summarizing the results of the real time PCR and the gel electrophoresis, it was demonstrated that the addition of Q-VD-OPh or Z-Val-Ala-Asp(OMe)-FMK inhibits DNA fragmentation and furthermore, reduces the release of genomic DNA into blood plasma. Thus, adding a caspase inhibitor to whole blood is effective in stabilising the sample and in particular the extracellular nucleic acid population even at room temperature. Thus, using the stabilisation method according to the present invention, allows to ship whole blood samples even at room temperature without jeopardizing the quality of the sample. To completely prevent release of genomic DNA also during longer storage periods, the concentration of Q-VD-OPh may also be increased.

Example 2

Influence of Lower Concentrations of Caspase-Inhibitor Q-VD-OPh on Blood Stability In this example, lower concentrations of the caspase inhibitor Q-VD-OPh was tested in combination with glucose, wherein the glucose was added as combination partner to support that the blood cells stay alive (by preventing cell damage). 21.4 mM glucose and 4 µM, 1 µM or no Q-VD-OPh were added to 10 ml blood drawn into BD Vacutainer tubes and stored for up to 7 days at room temperature. The whole blood sample was processed as described in section I, see 2. (plasma preparation) and 3. (nucleic acid isolation).

Results of the Chip Gel Electrophoresis

Figure 2A:
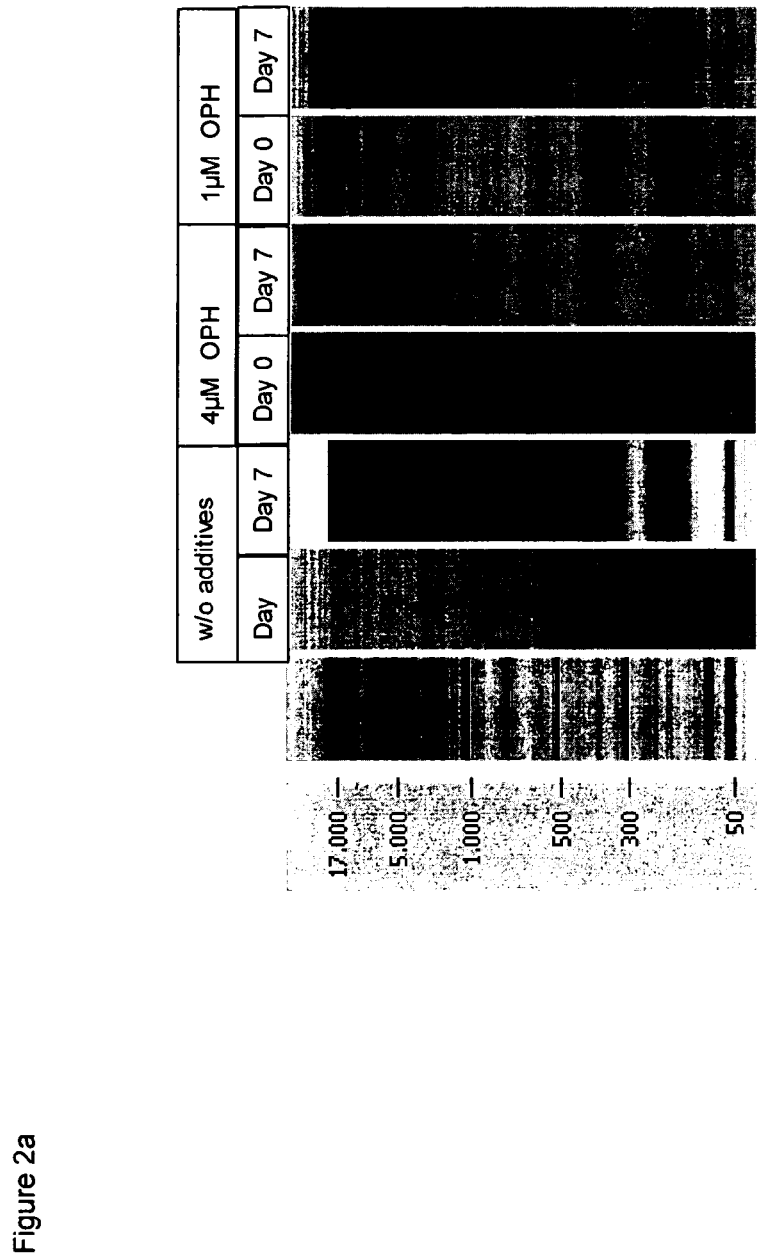
FIG. 2a shows a gel picture after chip electrophoresis of DNA isolated from samples treated with different concentrations of the caspase inhibitor Q-VD-OPH in combination (Example 2).

The eluted DNA was separated by size using chip gel electrophoresis (for details on the method see above, I, 4.1). FIG. 2a shows that compared to the control samples, wherein no caspase inhibitor was added, already 1 µM caspase inhibitor significantly reduced the genomic DNA release/fragmentation on day 7. The effect is improved if 4 µM caspase inhibitor is used. Thus, already very low concentrations of the caspase inhibitor are effective in stabilising the blood sample, in particular when combined with a carbohydrate.

Results of the DNA Quantification

Figure 2B:
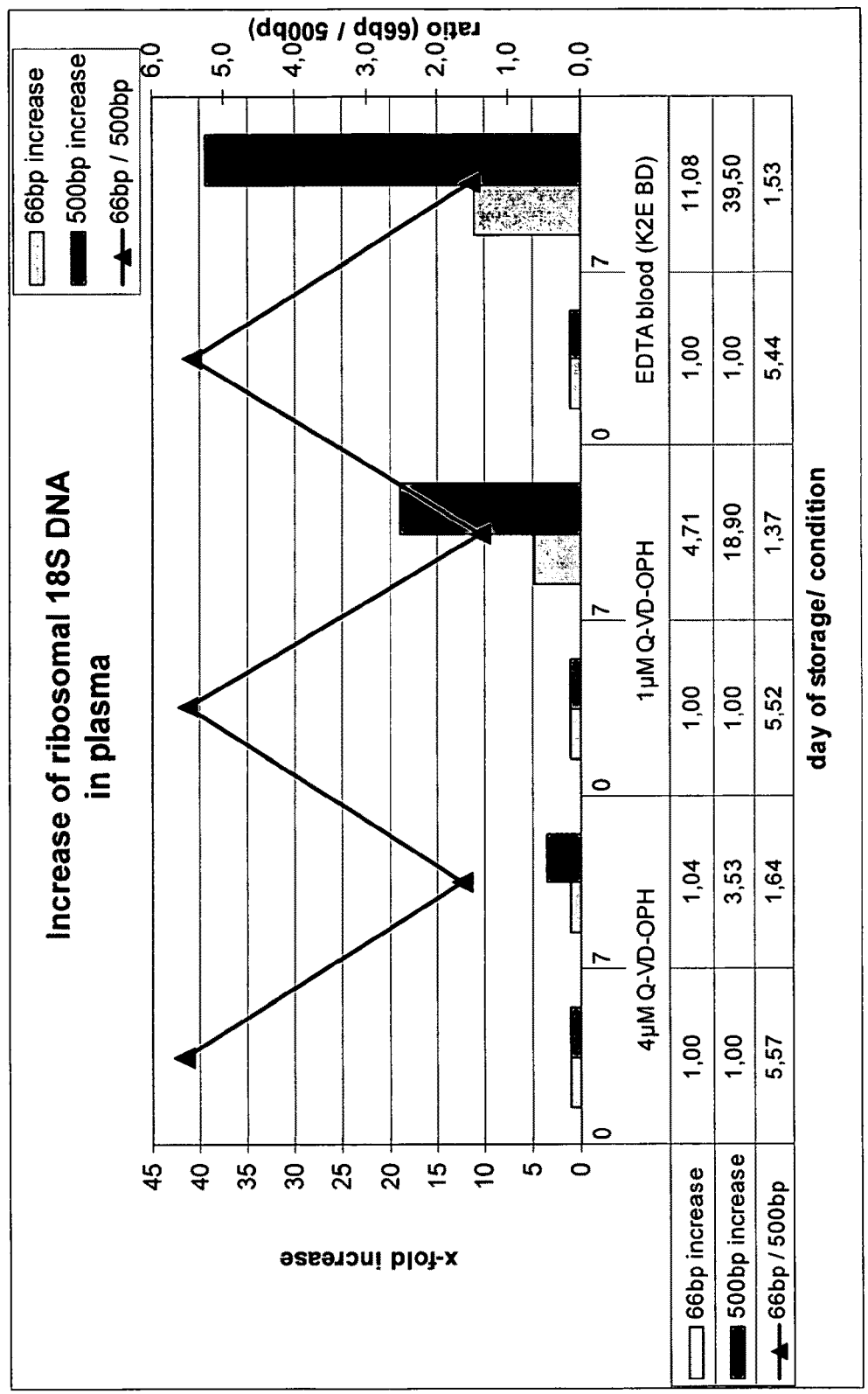
FIG. 2b is a diagram showing the effects of different concentrations of the caspase-inhibitor Q-VD-OPH in combination with glucose on the increase of ribosomal 18S DNA in the plasma (Example 2).

FIG. 2b shows the effects of the tested concentrations of the caspase-inhibitor Q-VD-OPh in combination with 21 mM glucose on the increase of genomic DNA in the plasma (18S DNA duplex assay) within 7 days of storage at RT. The addition of Q-VD-OPh in combination with glucose significantly reduces the release of genomic DNA into plasma. FIG. 2b shows only a minor increase of genomic DNA within 7 days of storage even if only 1 µM Q-VD-OPH was added to the whole blood sample for stabilisation. The addition of 4 µM Q-VD-OPh inhibits the release of genomic DNA to plasma to a maximum of a 4-fold increase. In contrast, drawing whole blood in K2E Tubes without stabilisation according to the present invention leads to approximately 40-fold increase of DNA in plasma.

Thus, also FIG. 2 b) confirms that the caspase inhibitor has a stabilisation effect on whole blood even at low concentrations.

Example 3

Stabilizing Blood Cells by Osmotic Effects

Surprisingly it was also found by the inventors that blood cells can be stabilized by adding a reagent that acts as a hypertonic medium in whole blood. Generating a hypertonic medium by the addition of, for example, hydroxylated organic compound(s) to whole blood results in a slight release of water from the contained blood cells and results in increased stability by cell shrinking. It is assumed that said cell shrinking stabilises the cells against mechanical forces.

Dihydroxyacetone (DHA) is an intermediate product of the fructose metabolism and its phosphate form dihydroxyacetone phosphate (DHAP) is part of the glycolysis. DHA was tested as hypertonic agent. Addition of this reagent sensitively forces blood cells to shrink without damaging them. DHA was first dissolved in PBS (purchased from SIGMA-Aldrich Kat. No: D8537) or 3×MOPS (diluted from 1 litre of 10×MOPS: 200 mM MOPS; 50 mM NaAc, 10 mM EDTA; pH 5; assuming that an acid medium also stabilizes ccf RNA) obtaining 4.2M solved DHA. Then 2 ml of 4.2M DHA dissolved in Buffer PBS or buffer 3×MOPS were added to 10 ml of blood to obtain a final concentration of 0.7M DHA in whole blood. The two different solvents of DHA were compared to PAXgene® Blood DNA tubes (QIAGEN), a state-of-the-art blood collection tube for DNA stabilization.

Results of the FACS Analysis

Figure 3:
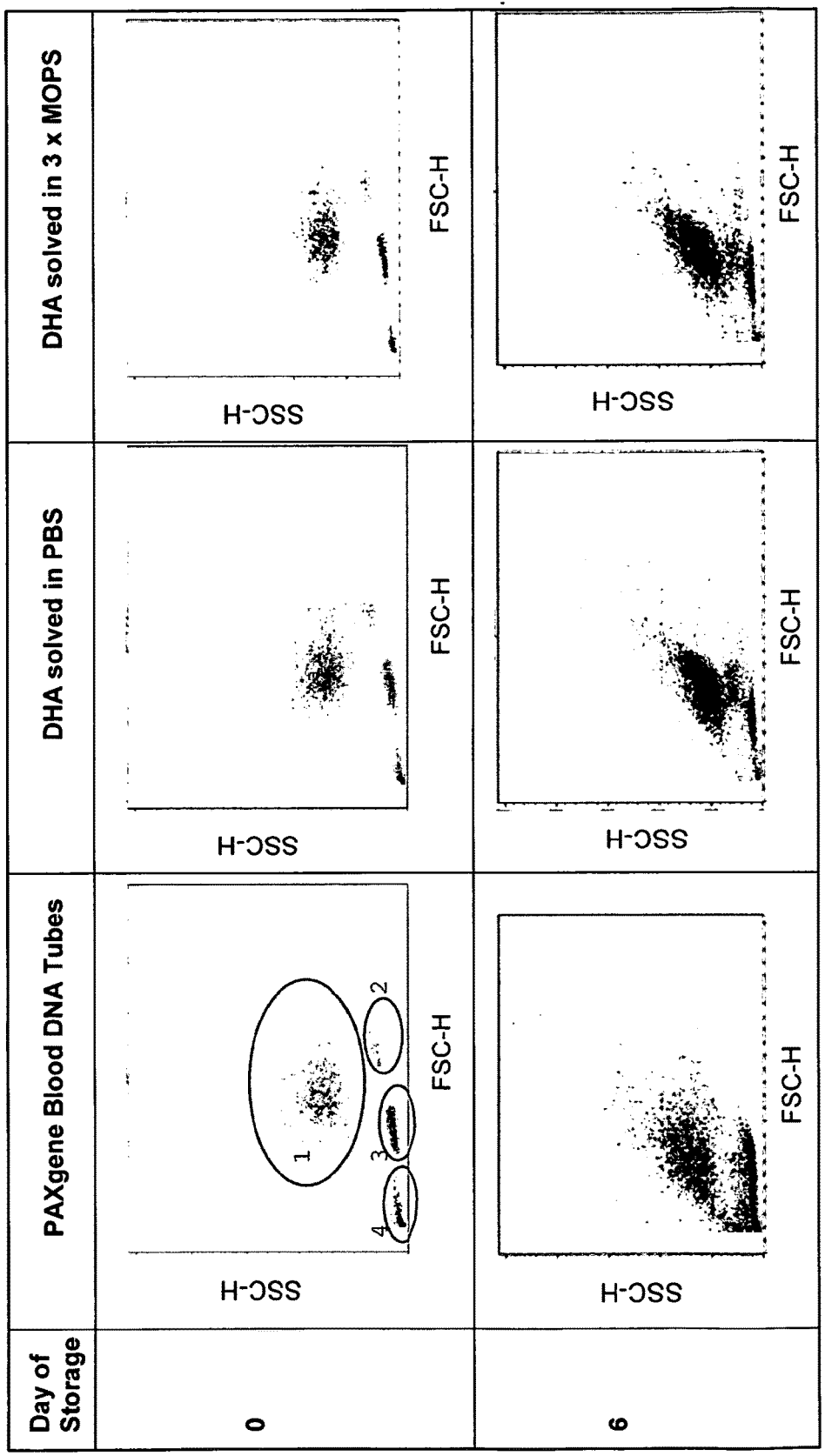
FIG. 3 shows the blood cell integrity measured by flow cytometry for blood cells treated with dihydroxyacetone dissolved in different buffers (Example 3).

The blood cell integrity was analysed using FACS (for details on the method see above, I, 1). FIG. 3 shows the blood cell integrity measured by flow cytometry. The Dot-Plots visualize three different cell populations: granulocytes (1), monocytes (2) and lymphocytes (3). The cloud (4) in the lower left field of the plot represents the debris, mainly generated by the lysis of erythrocytes.

The results in FIG. 3 show that blood cells collected and stored in PAXgene® Blood DNA tubes are not distinguishable from each other and the debris on day 6 of storage. The addition of DHA enables a differentiation of the subpopulations of blood cells on day 6 of storage even though these cells become smaller as a result of the cell shrinking. This indicates that the cells contained in the sample were stabilised by the addition of DHA.

Results of the Chip Gel Electrophoresis

Figure 4A:
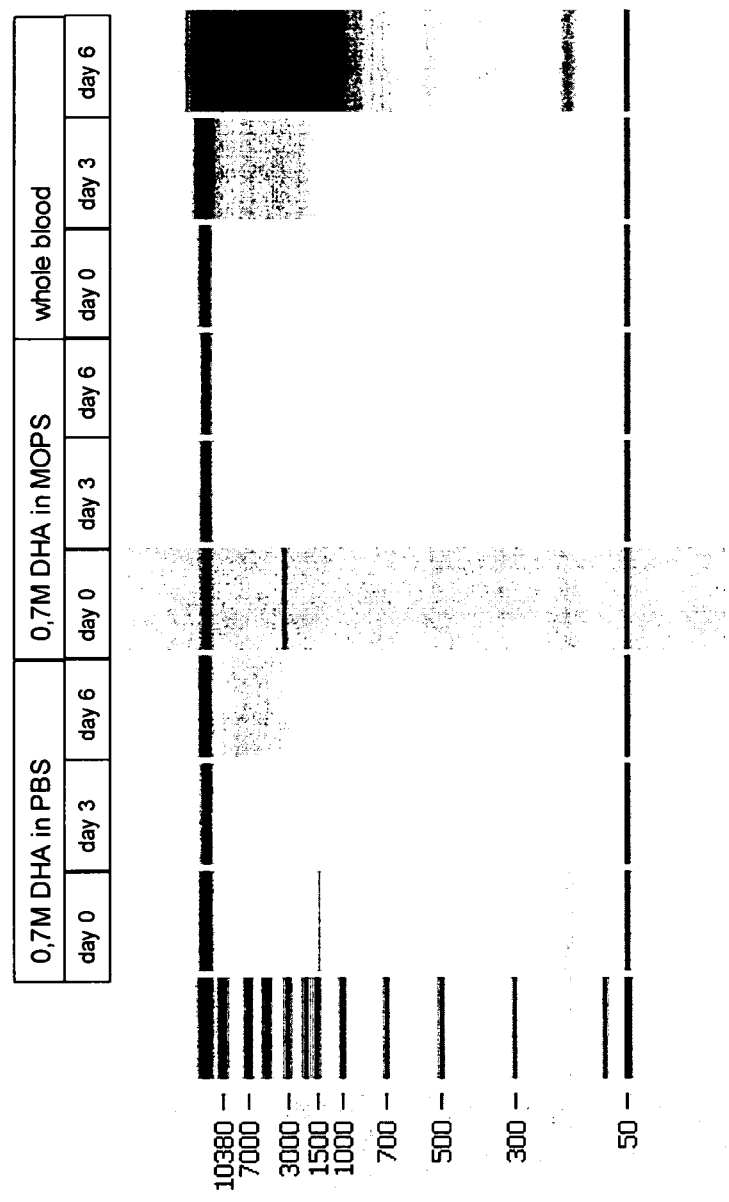
FIG. 4a shows a gel picture after chip electrophoresis of DNA isolated from samples treated with dihydroxyacetone dissolved in different buffers (Example 3).

The results presented in FIG. 4a also shows a stabilisation of the blood samples by the addition of DHA, because the release of genomic DNA is significantly lower with the DHA treated samples than in samples stored in PAXgene® Blood DNA tubes. Furthermore, as is evident from FIG. 4a, DHA-stabilized samples do not show ladder-like degradation pattern suggesting that apoptosis, respectively a degradation of DNA is efficiently prevented.

Results of the DNA Quantification

Figure 4B:
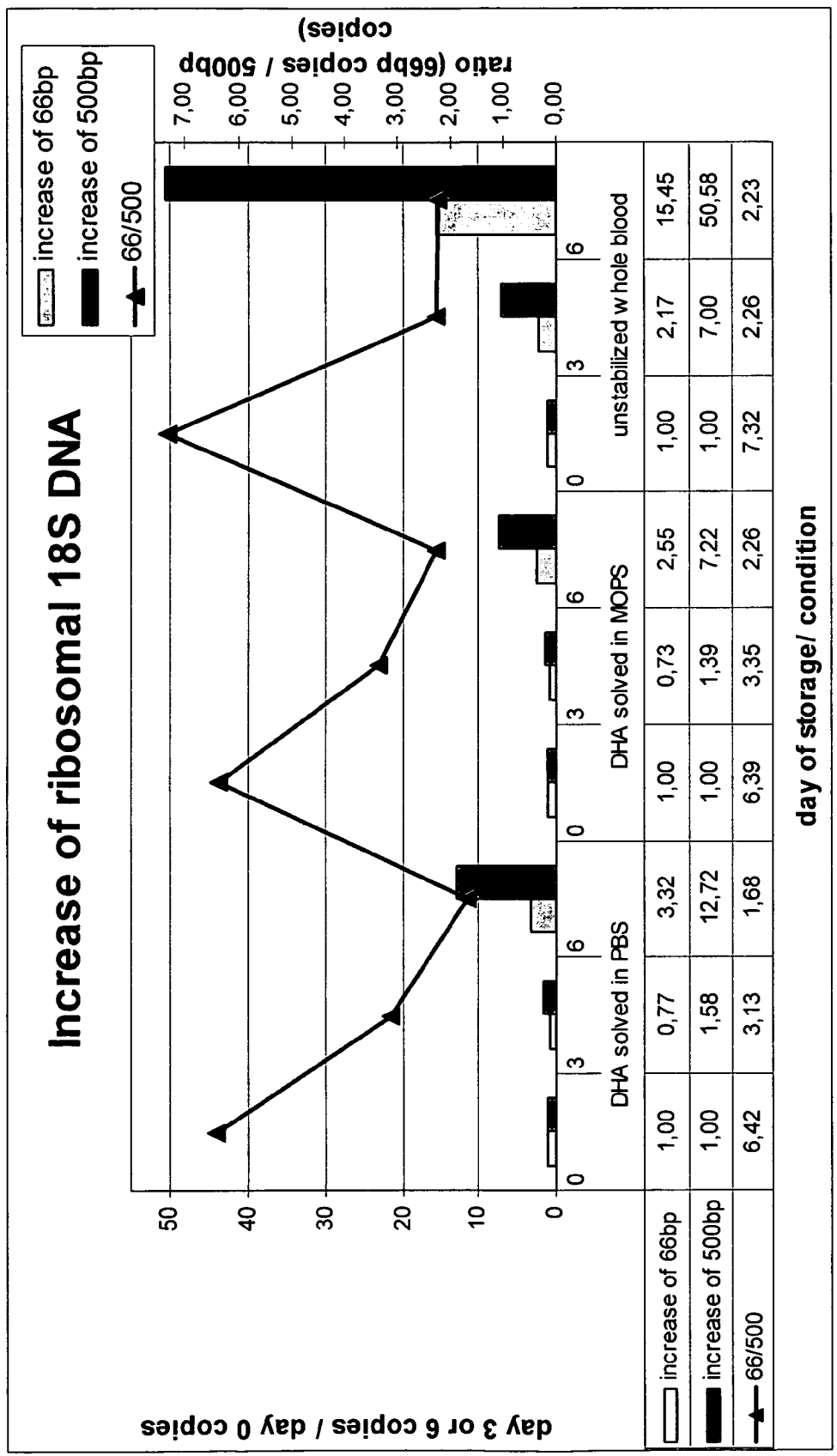
FIG. 4b is a diagram showing the effect of dihydroxyacetone on the increase of ribosomal 18S DNA (Example 3).

FIG. 4b shows the effect of DHA on the increase of DNA (18S DNA duplex assay) within 6 days of storage at RT. DHA dissolved in 3×MOPS provided the best results, because the level of ribosomal 18S DNA seems to remain constant till day 3 of storage.

The division of short amplicon copy number by long amplicon copy number (66 by/500 bp) indicates whether the amount of detected short or long amplicons changes over time in a similar way. A decrease of this ratio implies a stronger release of longer rather than of shorter DNA molecules and can be interpreted as release of high molecular weight genomic DNA from blood cells. The diagram shown in FIG. 4b indicates the release of genomic DNA for all three conditions. The results show that the presence of DHA slows this process down. Thus, also this experiment shows that the addition of DHA to whole EDTA blood stabilizes blood cells and hence preserves the ccfDNA population in the cell-free plasma fraction and avoids contaminations with DNA released from the cells contained in the sample e.g. due to mechanical breakup.

Example 4

Testing Different Concentrations of Dihydroxyacetone

In this example, the stabilising effect of different concentrations of DHA (0.7M, 0.5M and 0.2M) was tested.

Results of the FACS Analysis

Figure 5:
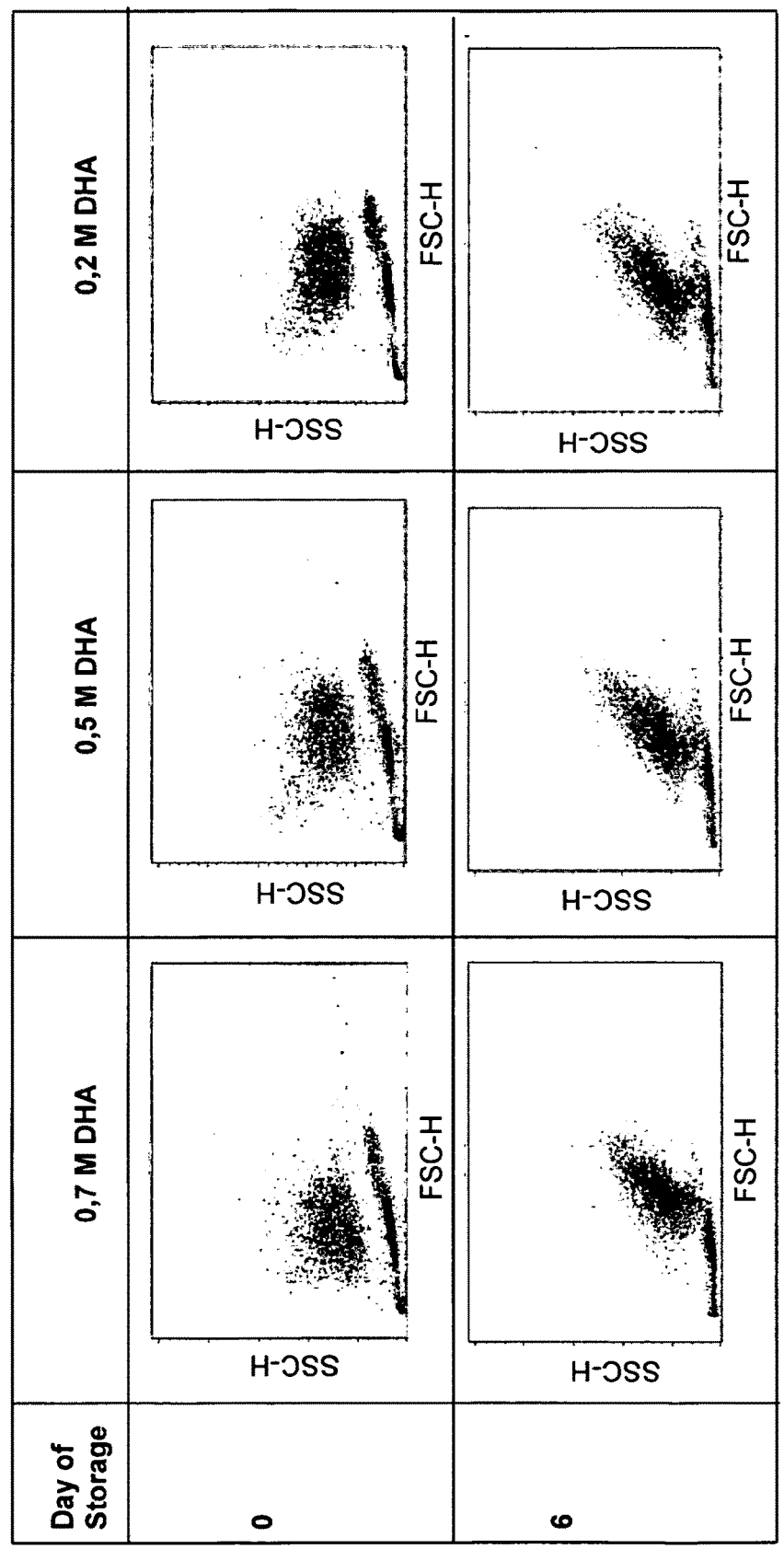
FIG. 5 shows the blood cell integrity measured by flow cytometry for blood cells treated with different concentrations of dihydroxyacetone (Example 4).

FIG. 5 shows the blood cell integrity measured by flow cytometry. The Dot-Plots visualize three different cell populations: granulocytes (1), monocytes (2) and lymphocytes (3). The cloud in the lower left field of the plot represents the debris, mainly caused by the lysis of erythrocytes.

Figure 6A:
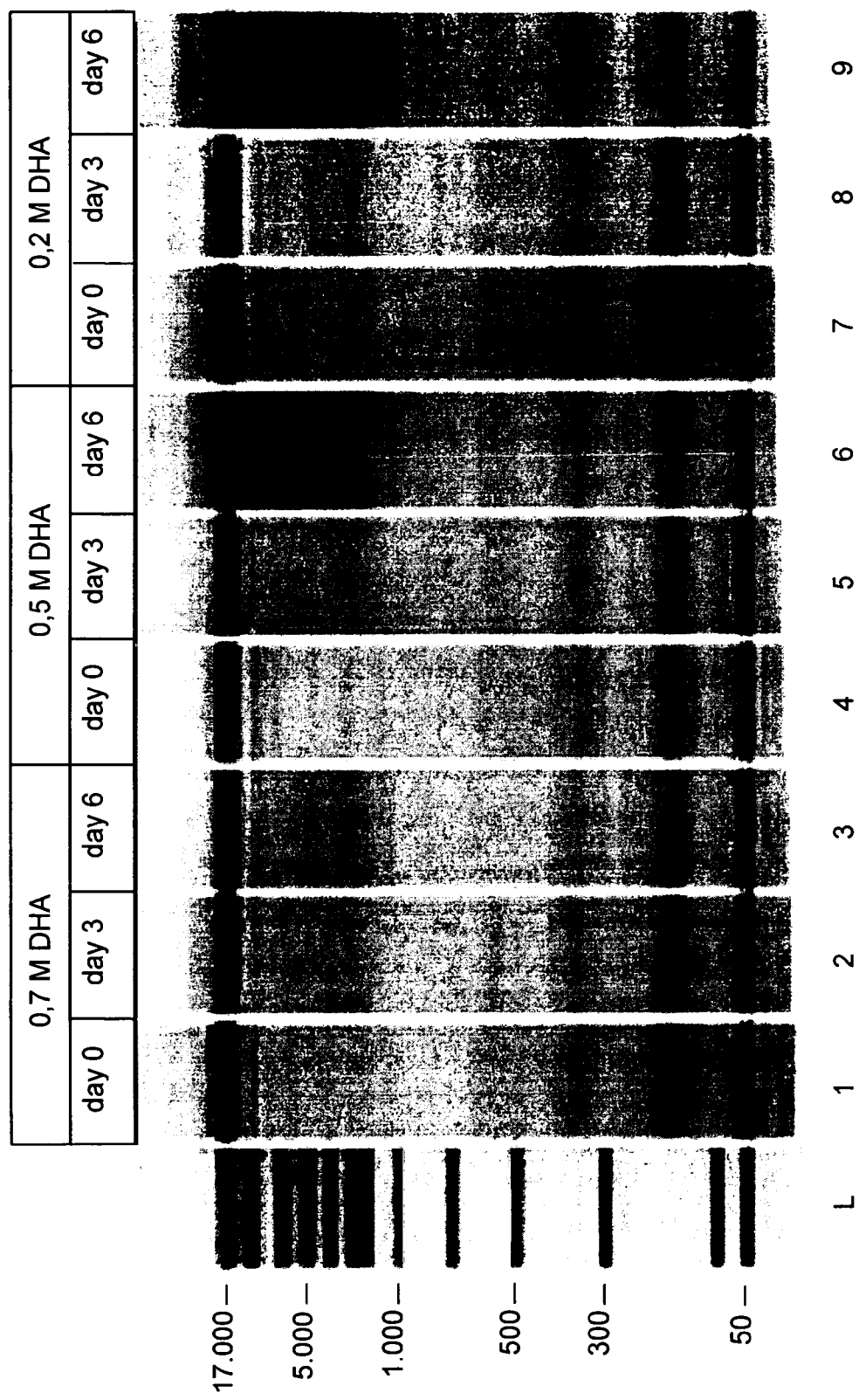
FIG. 6a shows a gel picture after chip electrophoresis of DNA isolated from samples treated with different concentrations of dihydroxyacetone (Example 4).

Due to the addition of DHA to whole blood the different cell populations can be distinguished even on day 6 of storage regardless of the DHA concentration. Although the results of the flow cytometry analysis (FIG. 5) do not show differences in cell integrity between the different concentrations of DHA Results of the Chip Gel Electrophoresis The results presented in FIG. 6a also show a stabilisation of the blood samples by the addition of the different concentrations of DHA, because the release of genomic DNA and the degradation of the DNA is efficiently prevented.

Results of the DNA Quantification

Figure 6B:
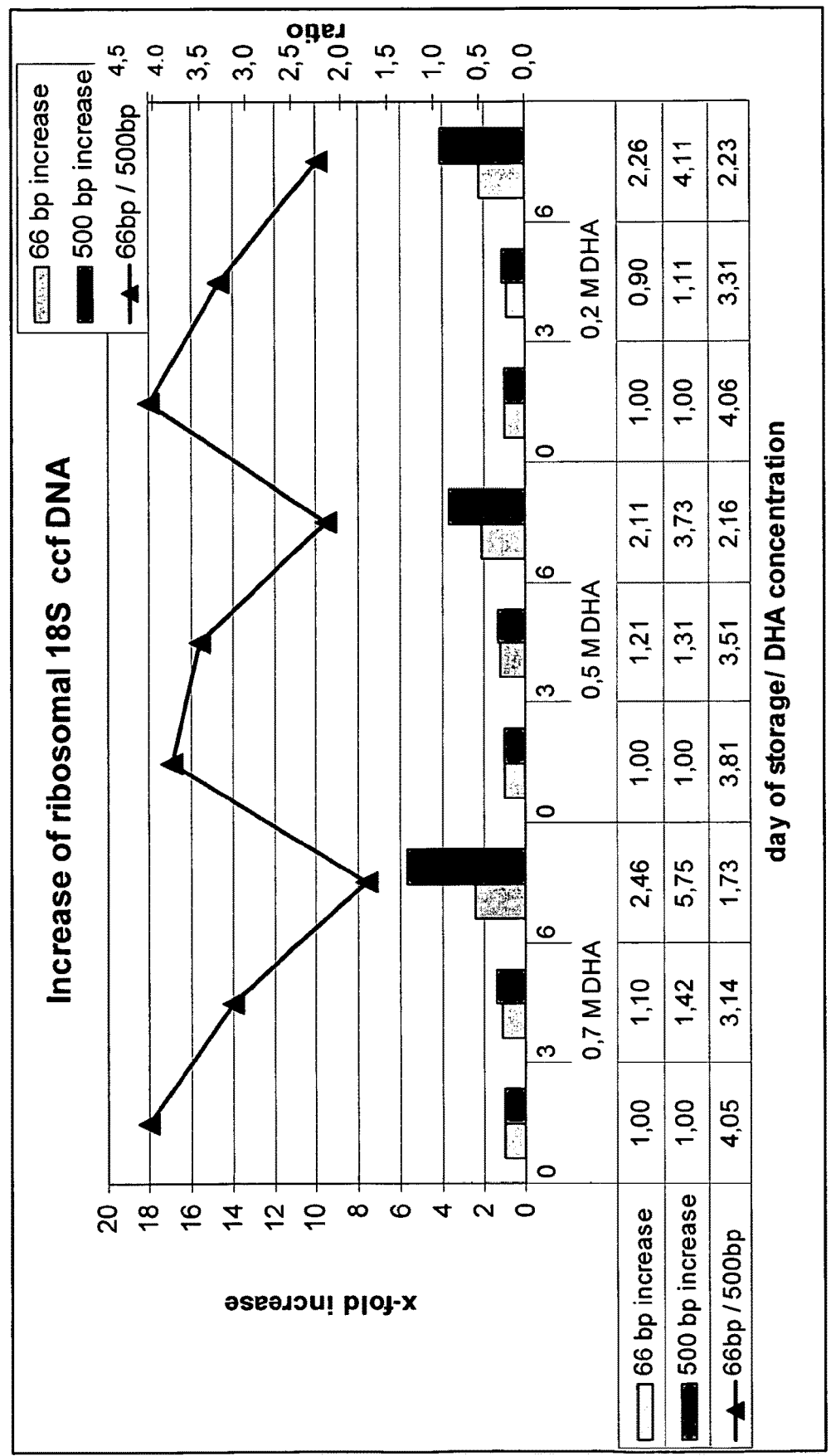
FIG. 6b is a diagram showing the effect of different dihydroxyacetone concentrations on the increase of ribosomal 18S DNA (Example 4).

FIG. 6b shows the effect of different DHA concentrations on the increase of DNA (18S DNA duplex assay) within 6 days of storage at RT. As shown in FIG. 6b, 0.5M DHA in whole blood prevents most efficiently the release of genomic DNA. Furthermore, the ratio of short to long amplicon copy numbers stays constant for up to 3 days and only decreases slightly till day 6. These results demonstrate the remarkable effect of the hypertonic agent DHA on the stabilisation of whole blood.

Example 5

Combination of an Apoptosis Inhibitor, an Osmotically Active Compound and an Anticoagulant An increase of EDTA in blood collection tubes inhibits micro- and macroclotting as it is known for PAXgene® Blood DNA tubes. Hence, higher concentrations of EDTA may support stabilization of blood cells and extracellular nucleic acids in plasma. Furthermore, the experiments presented above show an inhibitory effect of the caspase inhibitor, in particular Q-VD-OPh, and the osmotically active compound DHA on blood cell damage and in particular show that an increase of genomic DNA, in particular fragmented genomic DNA, in the extracellular nucleic acid population is efficiently reduced. Surprisingly, the caspase inhibitors tested also prevented/inhibited the leakage of genomic DNA into the cell-free (plasma) fraction. Hence, the combination of these reagents results in an improved stabilization of extracellular nucleic acids, in particular extracellular DNA, in whole blood that lasts at least for 6 days, and furthermore, results in an efficient stabilization of blood cells, thereby preventing the release of genomic DNA, what otherwise would result in a dilution of the natural extracellular nucleic acid level in plasma.

In this example, DHA was dissolved in 2 ml 3×MOPS (3M DHA in 2 ml 3×MOPS), 50 mg $K_2$EDTA and 2.4 µl of 5 nM Q-VD-OPh were added and then transferred into 10 ml whole blood, that was collected in K2E Tubes. Plasma samples were centrifuged for 10 min at 16.000×g, 4° C. and then purified using the QIAamp® Circulating NA Kit (Qiagen) (details are described above in section I).

Results of the FACS Analysis

Figure 7A:
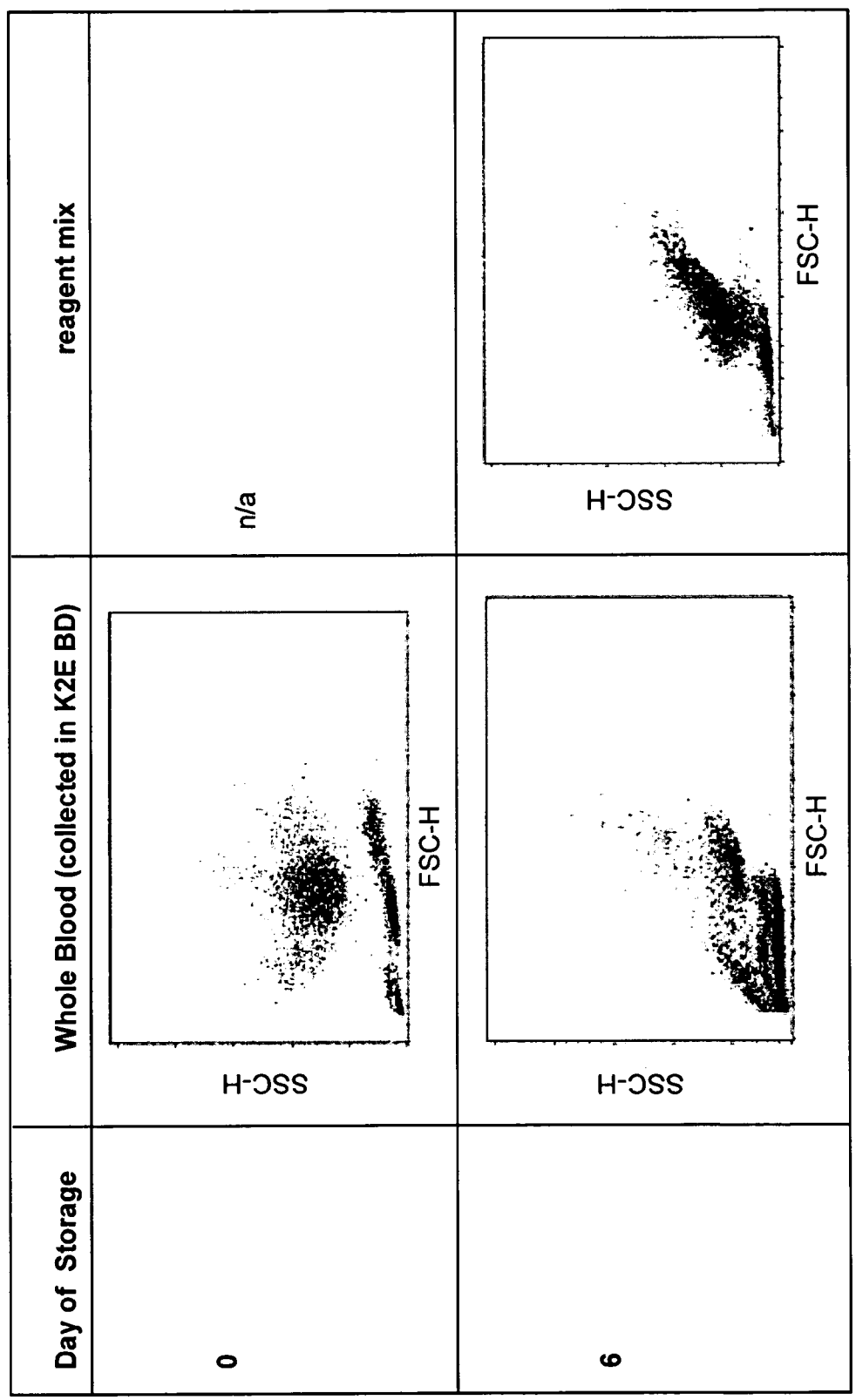
FIG. 7a shows the blood cell integrity measured by flow cytometry for blood cells treated with a combination of elevated $K_2$EDTA, Q-VD-OPH and DHA (Example 5).

FIG. 7a shows the blood cell integrity measured by flow cytometry. The Dot-Plots visualize three different cell populations: granulocytes (1), monocytes (2) and lymphocytes (3). The cloud in the lower left field of the plot represents the debris, mainly caused by the lysis of remaining erythrocytes.

The addition of the caspase inhibitor, the hypertonic agent and the complexing agent to whole blood resulted in a distinguishable pattern of blood cell populations after 6 days of storage. Thus, the cells contained in the blood sample were efficiently stabilised.

Results of the DNA Quantification

Figure 7B:
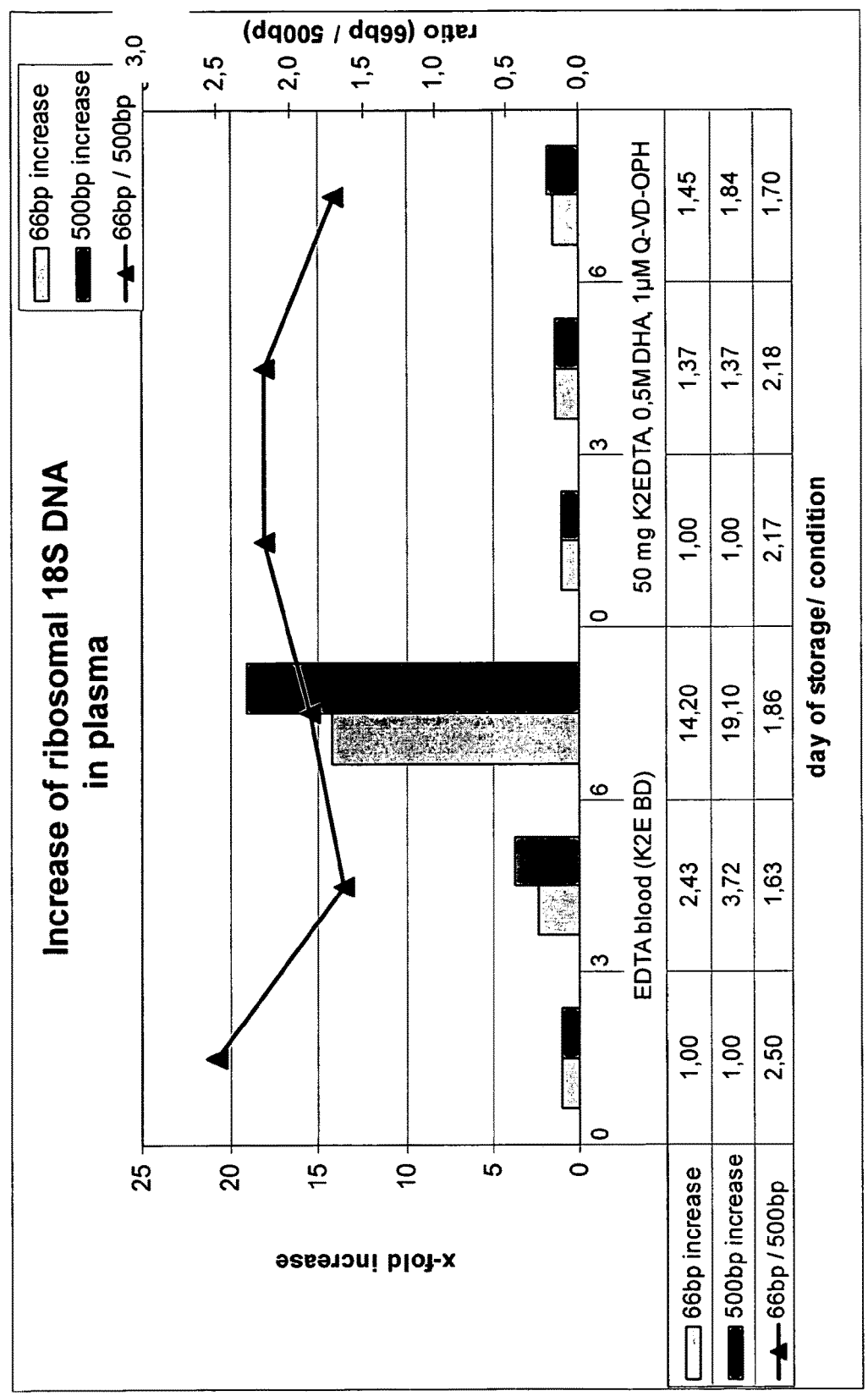
FIG. 7b is a diagram showing the effect of the combination of EDTA, DHA and Q-VD-OPH on the increase of 18S DNA (Example 5).

FIG. 7b shows the effect of the combination of EDTA, DHA and the caspase-inhibitor Q-VD-OPH on the increase of DNA (18S DNA duplex assay) within 6 days of storage at RT. The results indicate that the combination of EDTA, DHA and Q-VD-OPH leads to a remarkably strong stabilization of extracellular DNA in plasma (level of measured 18S rDNA remains constant till day 6) and to a strong prevention of the release of genomic DNA from blood cells (ratio of short to long amplicon copy numbers remains constant) till day 3 of storage. Only a slight increase of genomic DNA into plasma becomes visible between day 3 and day 6 of storage.

Thus, the tested combination of stabilising agents is particularly efficient in stabilising whole blood samples.

Example 6

Effect of an Apoptosis Inhibitor, an Osmotically Active Compound and a Preventing Agent on Free Circulating RNA in Whole Blood As a combination of $K_2$EDTA, Q-VD-OPh and DHA showed remarkable stabilizing effects on free circulating DNA and the integrity of blood cells in whole blood, the stabilising capacities of these agents on free circulating RNA was also analysed. To preserve a constant level of free circulating RNA in plasma (as present when collecting the blood), the stabilizing reagent(s) should not only protect RNAs from degradation and prevent the release of RNAs from decaying blood cells, but should also inhibit the metabolic pathways, respectively have the effect that changes in the metabolic pathway do not affect the extracellular RNA plasma level, respectively should reduce respective effects. Hence experiment 5 was repeated and the level of mRNA was measured by real time RT-PCR.

Figure 8:
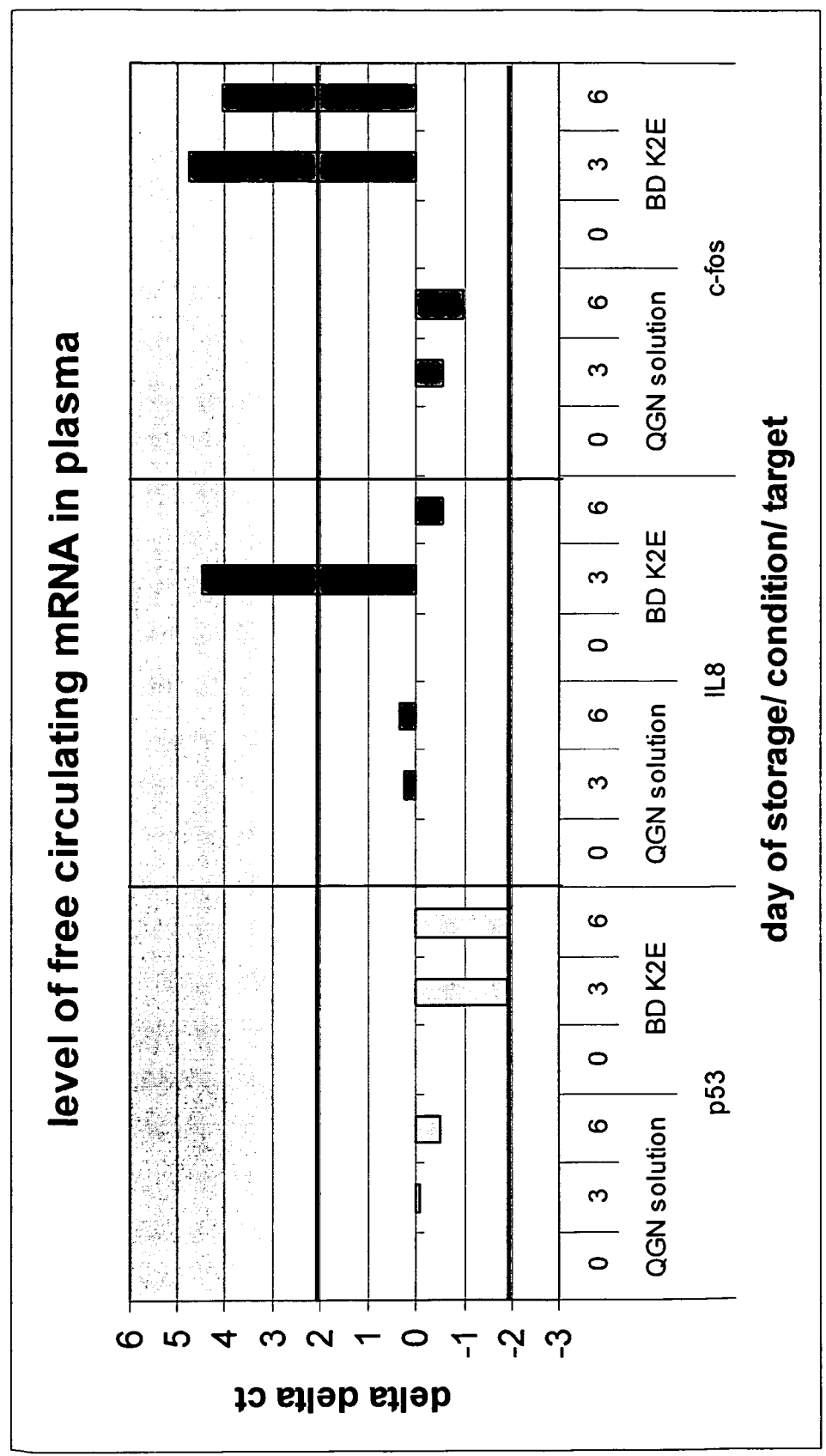
FIG. 8 is a diagram showing the effect of the combination of EDTA, DHA and Q-VD-OPH on the transcript level of free circulating mRNA in plasma (Example 6).
Figure 9:
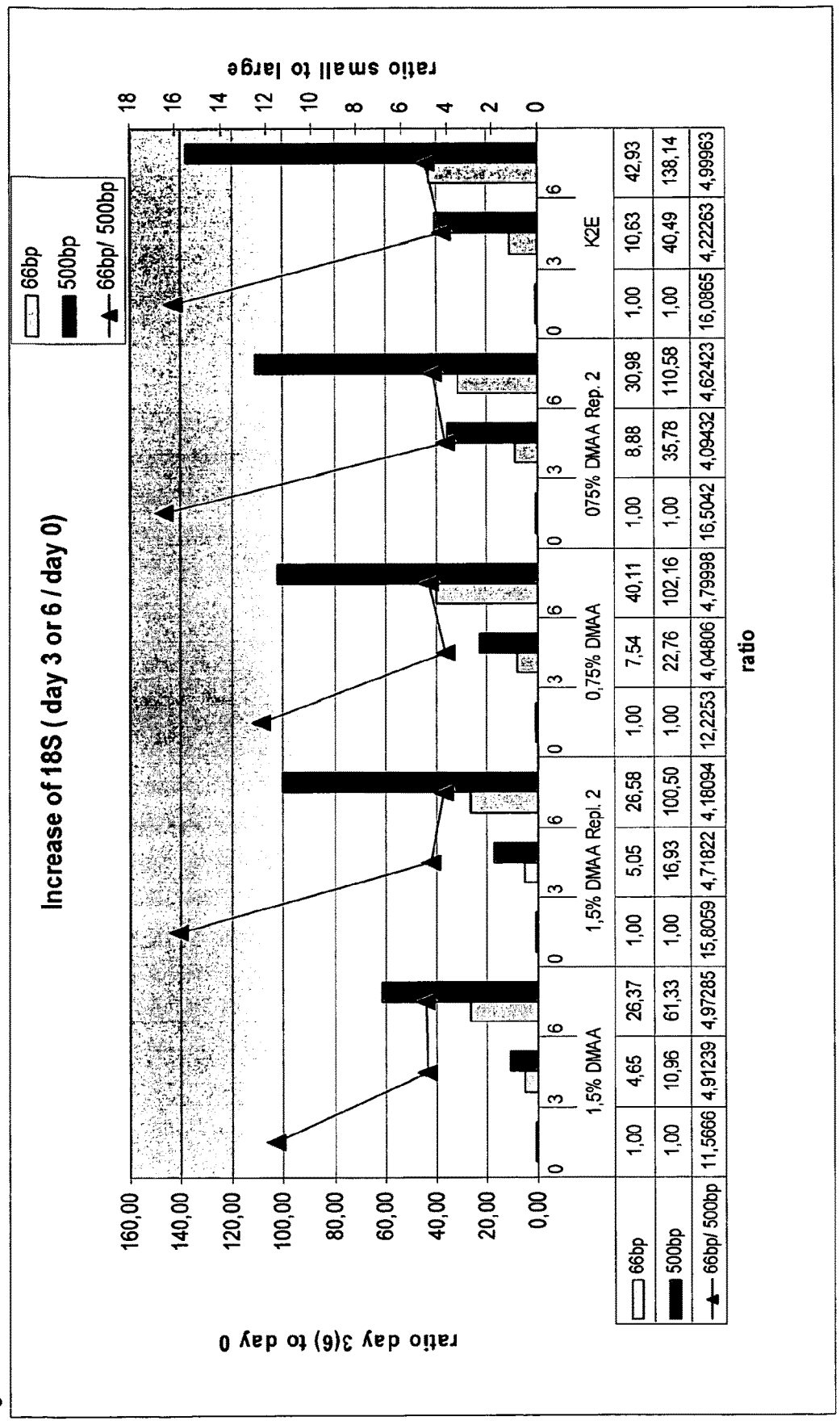
FIG. 9 is a diagram showing the effects of different concentrations of DMAA on the increase of ribosomal 18S DNA in the plasma.

FIG. 8 shows the effect of the combination of EDTA, DHA and the tested caspase-inhibitor on the transcript level in plasma within 6 days of storage. In order to measure variations in RNA levels, target mRNAs were referred to as reference target (18S rRNA) by calculating a ΔCt between p53, IL8 or c-fos and the internal standard (18S rRNA). Subtracting the ΔCt of day 3 or 6 samples with the ΔCt of day 0 samples defines the 4 ΔCt visualizing a relative decrease (– values) or increase (+ values) of mRNA transcript levels. IL8 and c-fos are genes whose transcription is induced after blood draw. Therefore, transcript levels of these targets would rise dramatically when cells release their contents; the addition of the stabilizing solution according to the preferred embodiment of present invention (combination of elevated EDTA, dihydroxyacetone, caspase inhibitor Q-VD-OPh) strongly prevents nucleic acid release from blood cells till day 3 of storage. But the data in the diagram above show—surprisingly—no significant increase of c-fos and IL8 mRNA till day 6 of storage. Thus, apparently the stabilization prevents the degradation of RNA (p53) and the release of mRNA (IL8/c-fos)

The transcription of p53 is repressed during continued metabolism after blood draw and, hence, a degradation or down-regulation of p53 mRNA would result in a decrease of (−)ΔΔcts. However, the results show that the tested QGN stabilisation solution prevents the p53 mRNA-level from being degraded during whole blood storage for up to 6 days.

This experiment demonstrated that the addition of a combination of elevated EDTA, dihydroxyacetone, caspase inhibitor Q-VD-OPh to freshly drawn whole blood acts to preserve the circulating plasma mRNA population which was present at the time of blood draw, reducing mRNA-specific changes in mRNA concentration. This is of particular importance for the analysis of circulating mRNA in plasma, e.g., for identification and characterization of potential tumor-specific mRNA species. Such studies require that the mRNA population in plasma remains substantially unchanged between blood draw and nucleic acid extraction and analysis.

Example 7

Stabilisation by the Addition of Dimethylacetamide (DMAA)

Two different concentrations of DMAA along with $K_2EDTA$ were tested and compared to EDTA alone (K2E BD; 18 mg $K_2EDTA$).

DMAA was added to replicates of whole blood samples (0.75% and 1.5% end concentration in 10 ml blood; blood was collected into Vacutainer K2E Tubes; BD).

Blood samples were incubated for up to 6 days at room temperature. On day 0, 3 and 6, whole blood samples were centrifuged at 1912×g for 15 min at room temperature, followed by a centrifugation of the plasma samples at 16.000×g for 10 min at 4° C. 1 ml of the sample input was used for DNA isolation following the protocol described in the materials & methods section. DNA was eluted in 80 µl EB buffer and quantified with the RT PCR assay described in I, 4.2.

Results of the DNA Quantification

Figure 11:
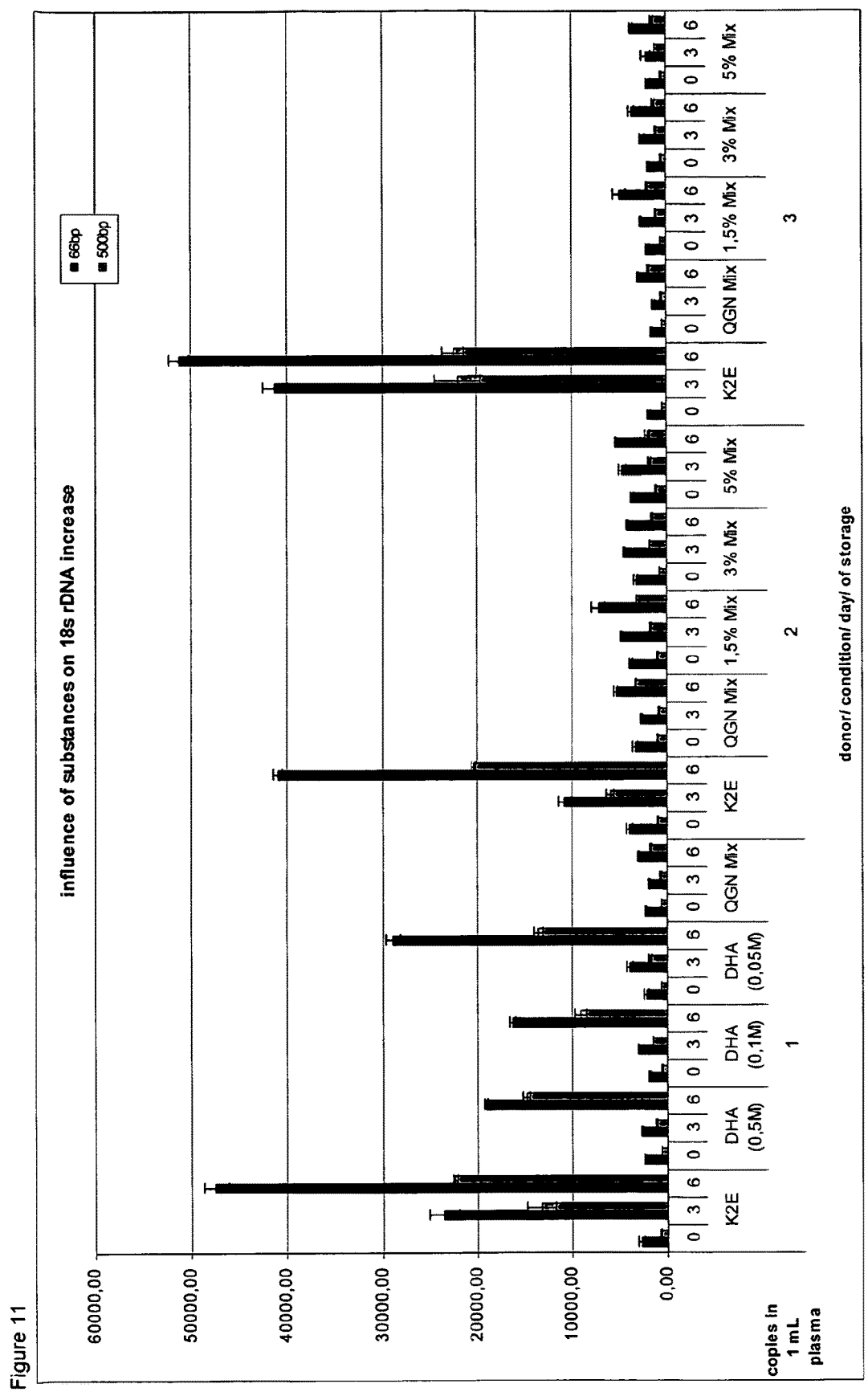
FIG. 11 is a diagram showing the influence of substances on the increase of 18S rDNA (Example 9)

FIG. 11 shows the effects of the tested concentrations of DMAA on the increase of genomic DNA in the plasma. Addition of DMAA significantly reduces the release of genomic DNA into plasma. The more DMAA is added to whole blood, the less DNA is released. Only a minor increase of cell-free DNA within 6 days of storage was observed if 1.5% DMAA was added to the whole blood sample. Furthermore, as the addition of 1.5% DMAA stabilizes cell-free DNA levels in whole blood samples more efficiently than 0.75% and the ratio of short to long measured 18S DNA copies decreases from day 0 to day 6, higher DMAA concentrations of than 1.5% can result in more efficient stabilization effects.

In summary, the addition of DMAA reduces the release of genomic DNA into blood plasma. Thus, adding DMAA to a blood sample is effective in stabilising the sample even at room temperature.

Example 8

Influence of Sugar Alcohols on Preserving the ccfDNA Status in Whole Blood 10 ml whole blood samples of two donors were first collected in BD Vacutainer K2E-EDTA (4.45 mM EDTA=Reference). Afterwards, 2 ml of the following stabilization solutions were added (given concentrations represent final concentration in stabilized blood solution):

| Stabilization Solution | Inositol (M) | Maltitol (M) | Mannitol (M) | Sorbitol (M) | DHA (M) | None (K2E) |
|---|---|---|---|---|---|---|
| 1 | 0.1 | | | | | |
| 2 | 0.05 | | | | | |
| 3 | 0.01 | | | | | |
| 4 | | 0.1 | | | | |
| 5 | | 0.05 | | | | |
| 6 | | 0.01 | | | | |
| 7 | | | 0.1 | | | |
| 8 | | | 0.05 | | | |
| 9 | | | 0.01 | | | |
| 10 | | | | 0.1 | | |
| 11 | | | | 0.05 | | |
| 12 | | | | 0.01 | | |
| 13 | | | | | 0.5 | |
| 14 | | | | | | X |

Figure 10:
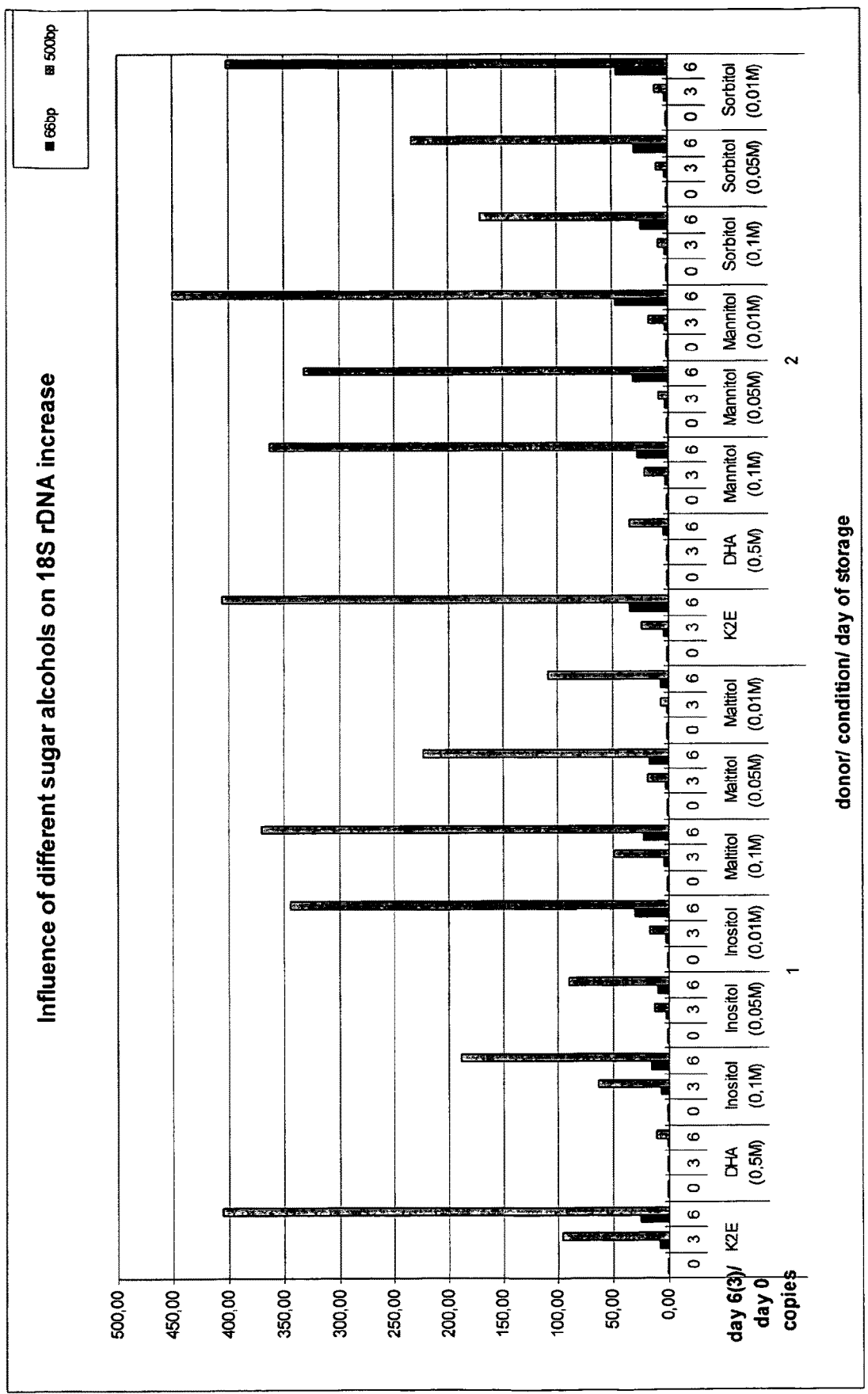
FIG. 10 is a diagram showing the influence of different sugar alcohols on the increase of 18S rDNA (Example 8)

The respectively stabilized samples were incubated at room temperature for up to six days. On day 0, day 3 and day 6, replicates were processed as follows. The samples were centrifuged at 3.000 rpm for 10 minutes at room temperature in order to collect plasma. The collected plasma was centrifuged at 16,000×g for 10 minutes at 4° C. The cleared plasma fraction was collected and the extracellular nucleic acids were isolated using the QIAamp Circulating nucleic acid kit (1 ml input material, 60 µl elution volume). The results are shown in relative change compared to the test time point 0 days (day X copies/day 0 copies) in FIG. 10. Values that are close to 1 imply preserved levels of ccfDNA. The higher the value, the less stabilization is achieved. From the sugar alcohols tested, very good results were achieved with DHA (0.5 M). Here, the lowest increase of ccfDNA levels in the plasma fraction was observed. Other suitable alternatives are inositol in concentrations of for example 0.05 M and maltitol in concentrations ≤0.01M. Furthermore, stabilization effects over 3 days were also seen with mannitol.

Example 9

Influence of DMAA, DHA and Glycine on ccfDNA Level 10 ml whole blood samples of three donors were first collected in BD Vacutainer K2E-EDTA (4.45 mM EDTA=reference). Afterwards, 2 ml of the following solutions were added (given concentrations represent final concentration in stabilized blood solution):

| Stabilization Solution | DHA (M) | DMAA (%) | EDTA | OPH (caspase inhibitor) | None (K2E) |
|---|---|---|---|---|---|
| 1 | 0.5 | | | | |
| 2 | 0.1 | | | | |
| 3 | 0.05 | | | | |
| 4 (QGN mixture) | 0.5 | | 14 mM | 1 µM | |
| 5 | | 1% | 14 mM | 1 µM | |
| 6 | | 3% | 14 mM | 1 µM | |
| 7 | | 5% | 14 mM | 1 µM | |
| 8 | | | | | X |

The samples were processed as described in example 8. The results as well as the test conditions are shown in FIG. 11. As can be seen, DHA alone stabilizes the level of ccfDNA for up to three days (see donor 1). Particularly stable ccfDNA levels were obtained when using the QGN mixture. Results comparable to the QGN mixture could be obtained when adding DMAA to the sample in combination with e.g. increasing the EDTA concentrations and adding a caspase inhibitor.

Example 10

Influence of Sugar Alcohol in Combination with Caspase Inhibitor and Increased EDTA Concentrations on ccfDNA Level 10 ml whole blood samples of two donors were first collected in the BD Vacutainer K2E-EDTA (4.45 mM EDTA=reference). Then, 2 ml of the following solutions were added (given concentrations represent final concentration in stabilized blood solution):
1: 0.5 M DHA, 1 µM OPH, 14 mM EDTA (QGN mixture);
2: 0.5 M Inositol in QGN mix (without DHA);
3: 0.01M Maltitol in QGN mix (without DHA).

Figure 12:
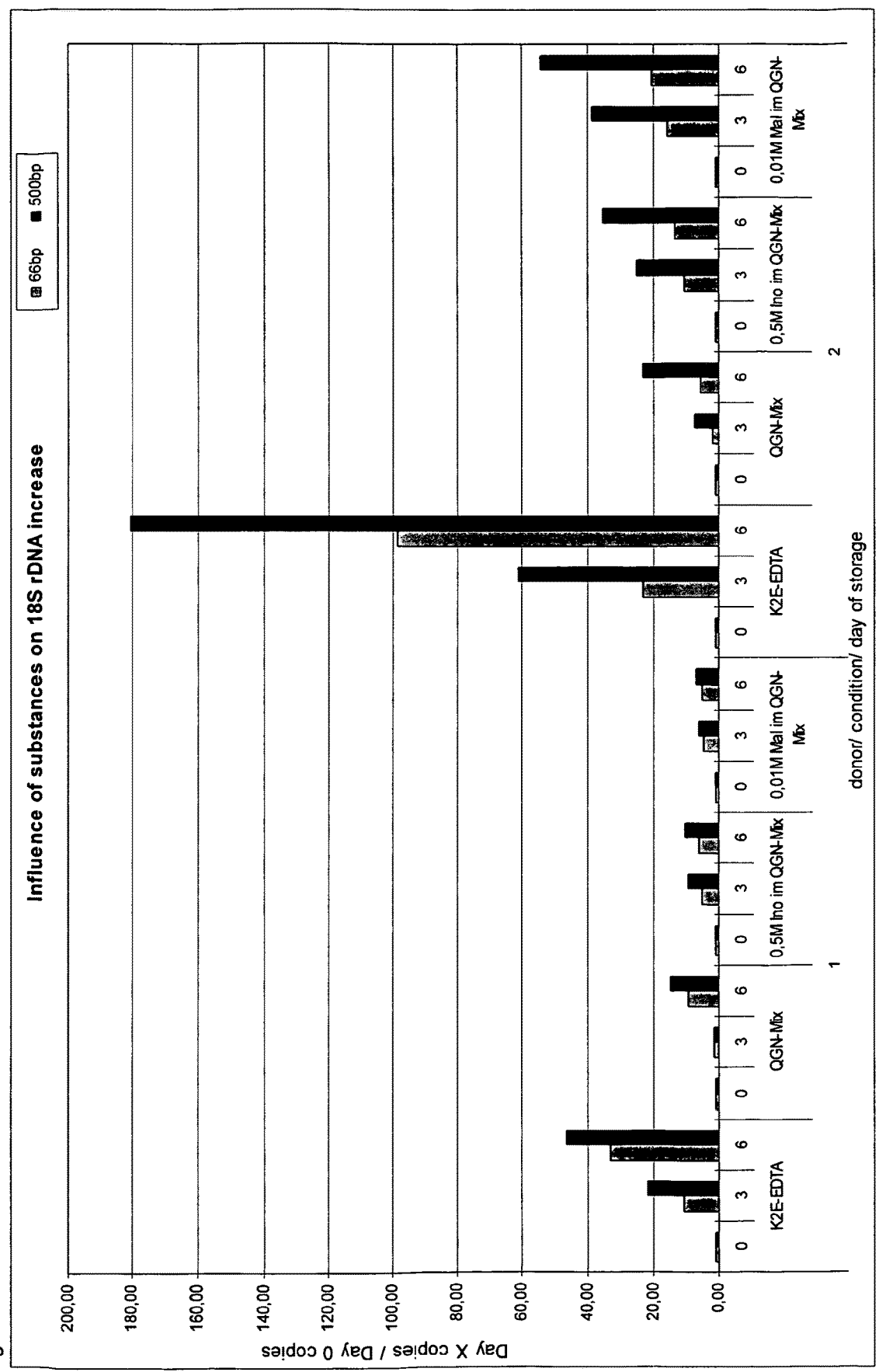
FIG. 12 is a diagram showing the influence of substances on the increase of 18S rDNA (Example 10)

The samples were then processed as described in example 8. The results are shown in FIG. 12. The best results were obtained for the QGN mixture. Combinations of sugar alcohol to the QGN mixture also showed stabilizing effects when compared to the EDTA stabilized samples.

Example 11

Influence of Combinations of DMAA and OPH (Caspase Inhibitor) Concentrations on ccfDNA Levels 10 ml whole blood samples were first collected in BD Vacutainer K2E-EDTA (4.45 mM EDTA=reference). Then, 2 ml of the following solutions were added (given concentrations represent final concentration in stabilized blood solution). Each condition was tested with six tubes from different donors.
1: EDTA reference (BD Vacutainer K2E);
2: QGN mixture;
3: 50 mg EDTA, 1 µM OPH;
4: 50 mg EDTA, 2 µM OPH;
5: 50 mg EDTA, 1 µM OPH, 5% DMAA;
6: 50 mg EDTA, 1 µM OPH, 10% DMAA;
7: 50 mg EDTA, 2 µM OPH, 5% DMAA;
8: 50 mg EDTA; 2 µM OPH and 10% DMAA.

Figure 13:
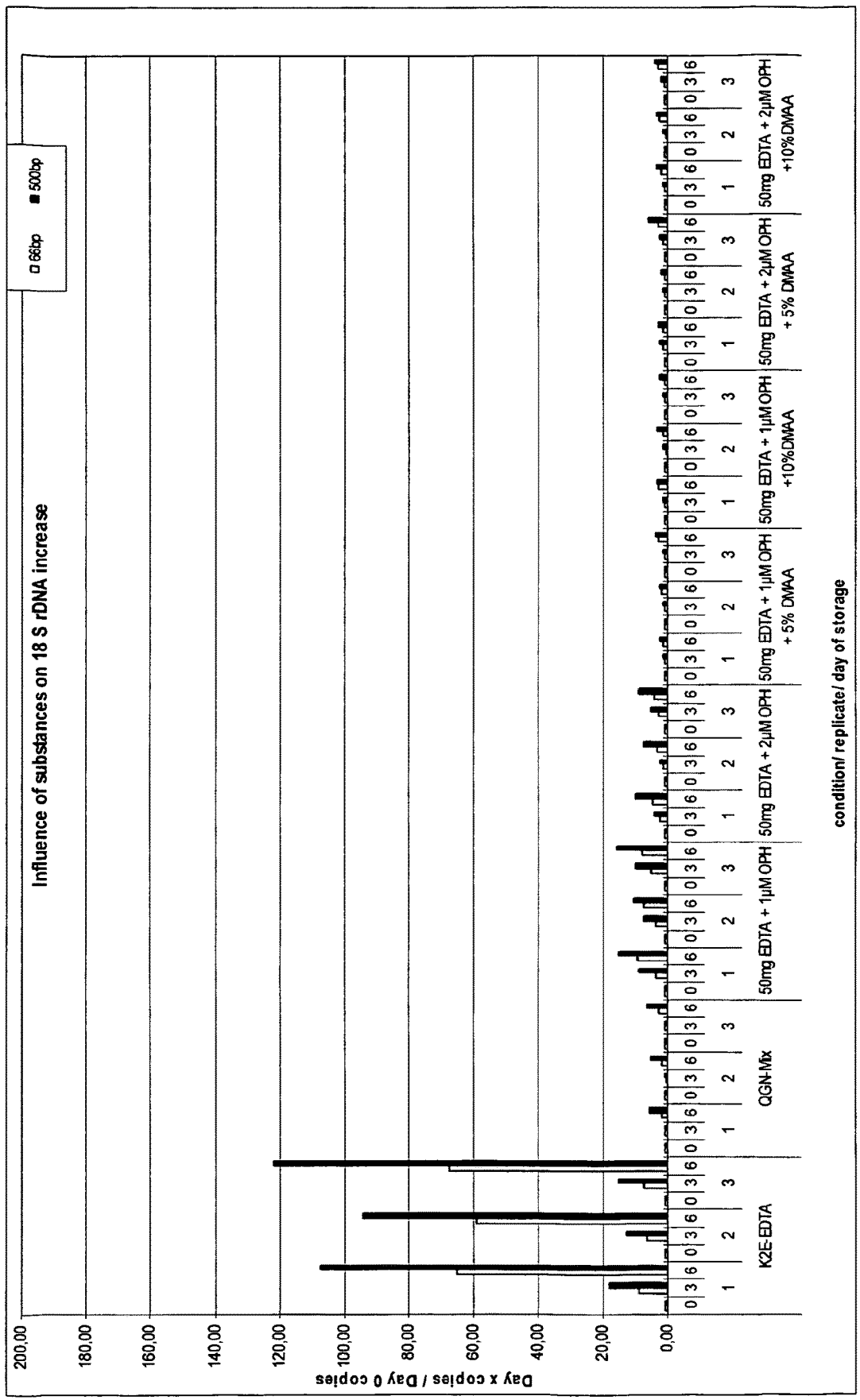
FIG. 13 is a diagram showing the influence of substances on the increase of 18S rDNA (Example 11)
Figure 14:
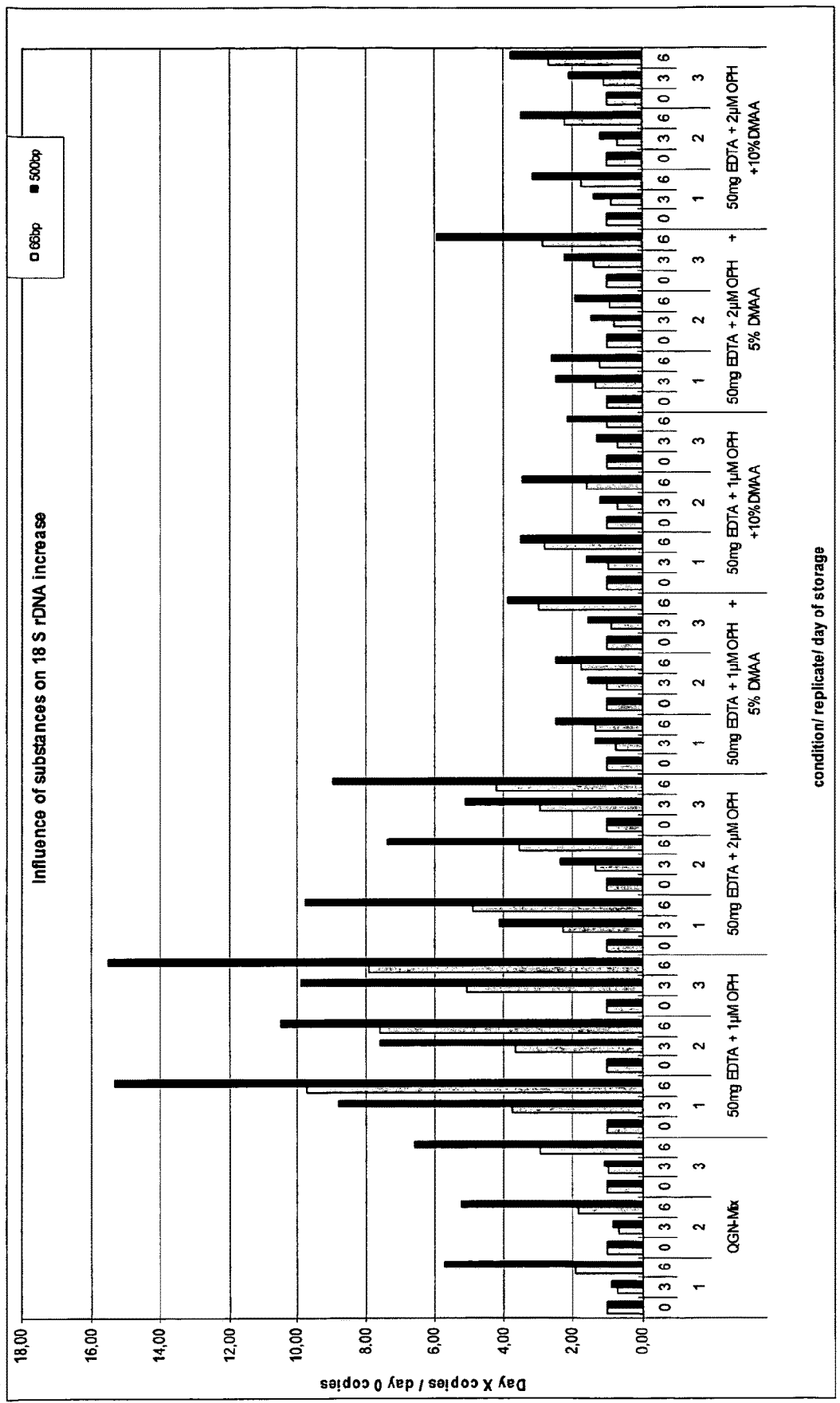
FIG. 14 is a diagram showing the influence of substances on the increase of 18S rDNA (Example 11)

The sample incubation, isolation of plasma and isolation from nucleic acids from the cleared plasma fraction were performed as described in example 8. However, after the first centrifugation step at 3.000 rpm, plasma samples of identical stabilization conditions were pooled before the second centrifugation step for plasma clearing (16.000×g) was carried out. The results are shown in FIG. 13. As can be seen, different DMAA concentrations in combination to different OPH concentrations show comparable results to the QGN mixture. FIG. 14 shows the influence of combinations of DMAA and OPH concentrations on ccfDNA levels (different scaling due to exclosure of reference data).

Example 12

Influence of Combination of QGN Mixture with Sugar Alcohols on ccfDNA Level 10 ml whole blood samples were collected in BD Vacutainer K2E-EDTA (4.45 mM EDTA=reference). Afterwards, 2 ml of the following solutions was added (given concentrations represent final concentration in stabilized blood solution). Each condition was tested with six tubes and thus six different donors.
1: EDTA reference (BD Vacutainer K2E);
2: QGN mixture (0.01M DHA, 14 mM EDTA, 1 µM OPH);
3: 0.01M DHA;
4: 5% DMAA, 14 mM EDTA, 1 µM OPH;
5: 0.01M DHA, 3% DMAA, 1 µM OPH, 14 mM EDTA;
6: 1 µM OPH, 14 mM EDTA, 0.01M DHA, 0.01M Maltitol;
7: 1 µM OPH, 14 mM EDTA, 0.01M DHA, 0.05 M Inositol;
8: 1 µM OPH, 14 mM EDTA, 0.01M DHA, 0.05M Inositol, 0.01M Maltitol.

Figure 15:
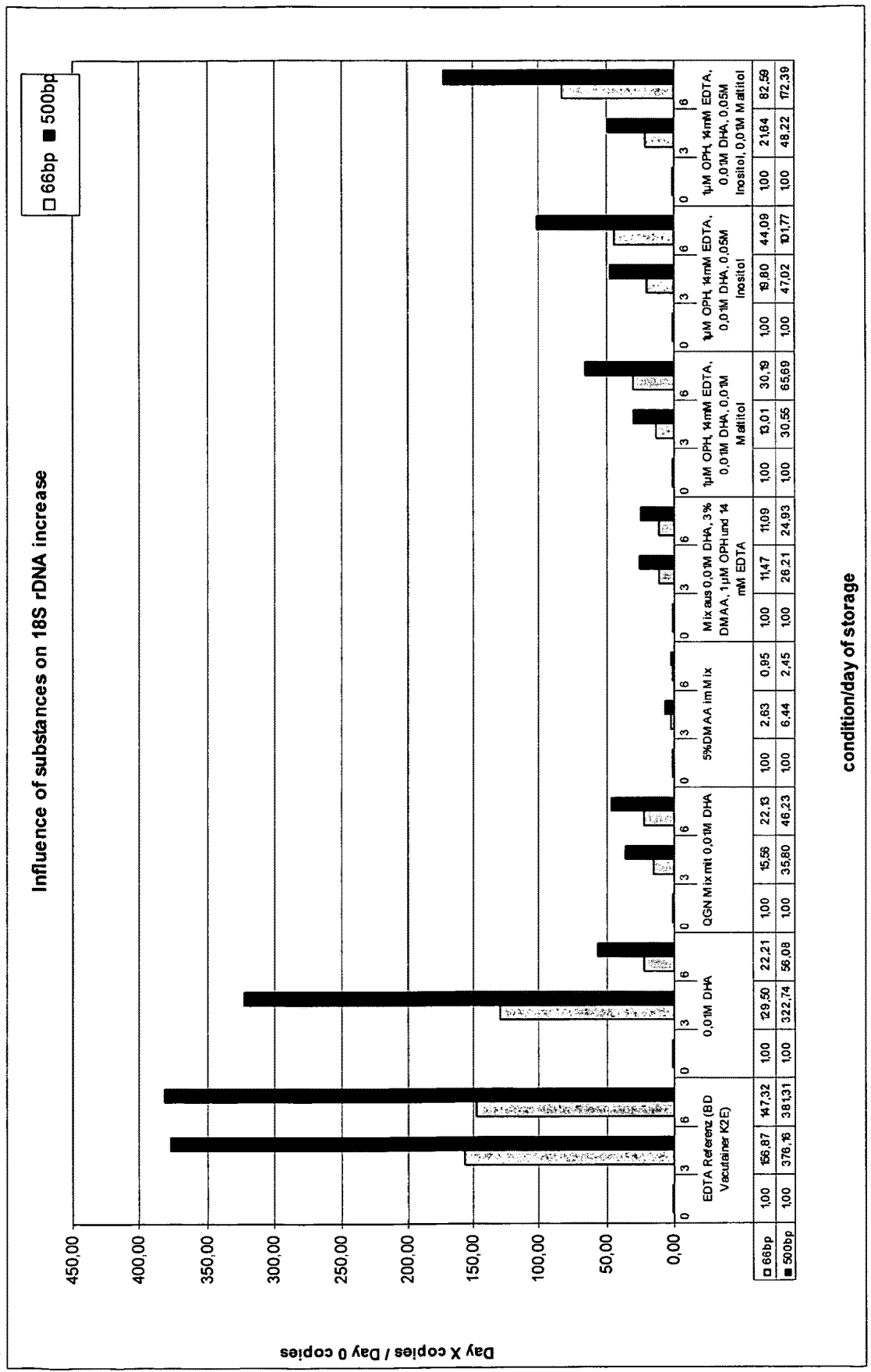
FIG. 15 is a diagram showing the influence of substances on the increase of 18S rDNA

The samples were processed as described in example 11. However, the samples were not stored at room temperature, but at 37° C. instead. The results are shown in FIG. 15. As can be seen, stable levels of ccfDNA were achieved, especially when 5% DMAA was added in combination with 14 mM EDTA and 1 µM OPH. Therefore, unexpectedly, a very good stabilization of ccfDNA in whole blood could be achieved even if at elevated temperatures (37° C.).

Example 13

Incubation at 37° C.—Analysis of Single Donor Samples

Whole blood samples from six different donors were collected in BD Vacutainers K2E, and then 2 ml of the following stabilization solutions were added per 10 ml whole blood (given concentrations represent final concentration in stabilized blood solution):
1: 2 µM OPH, 14 mM EDTA, 5% DMAA;
2: 1 µM OPH, 14 mM EDTA, 3% DMAA;
3: 1 µM OPH, 14 mM EDTA, 0.01M DHA, 3% DMAA.

Figure 16:
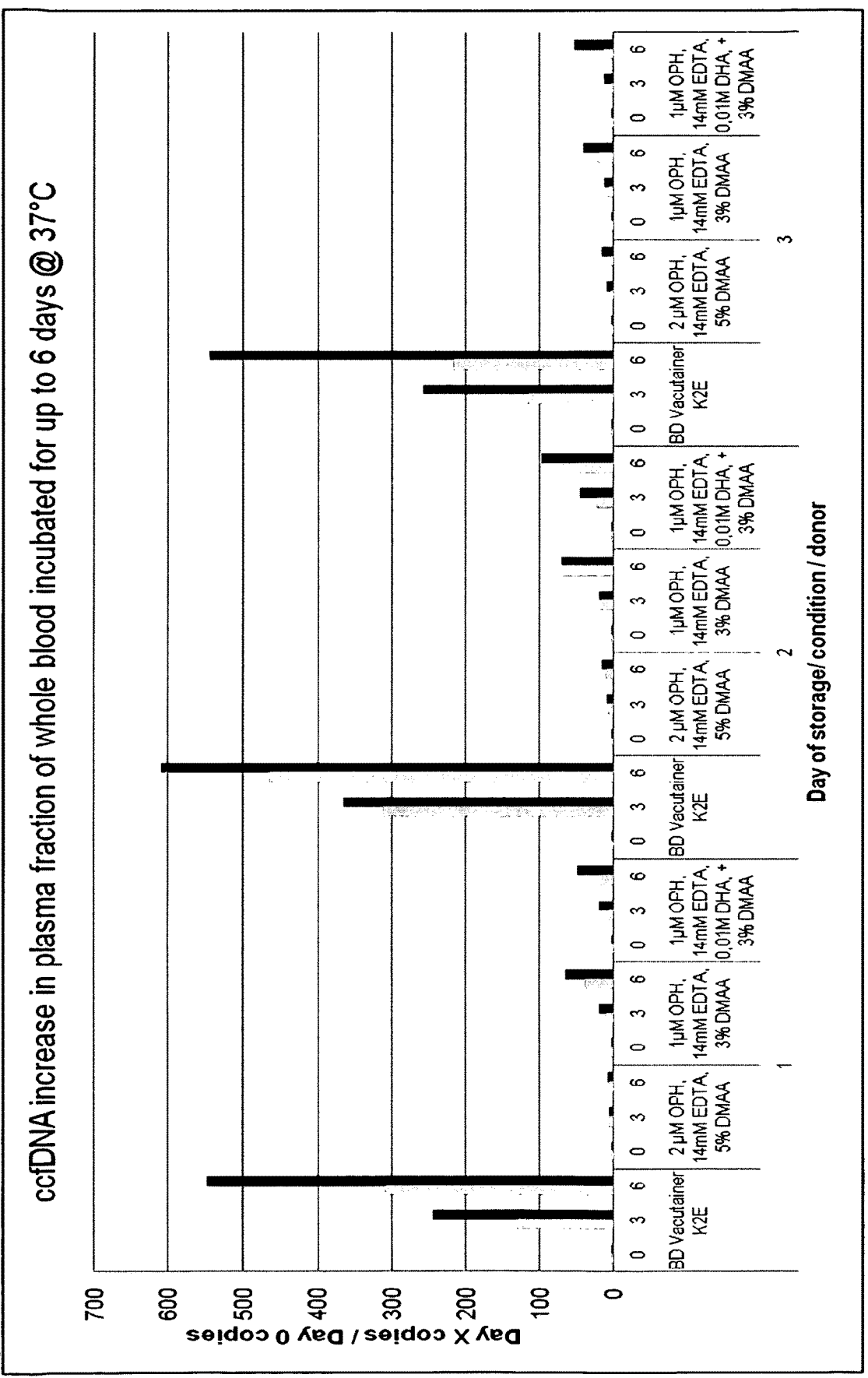
FIG. 16 is a diagram showing the ccfDNA increase in plasma fraction of whole blood incubated for up to 6 days at 37° C. (Example 13)
Figure 17:
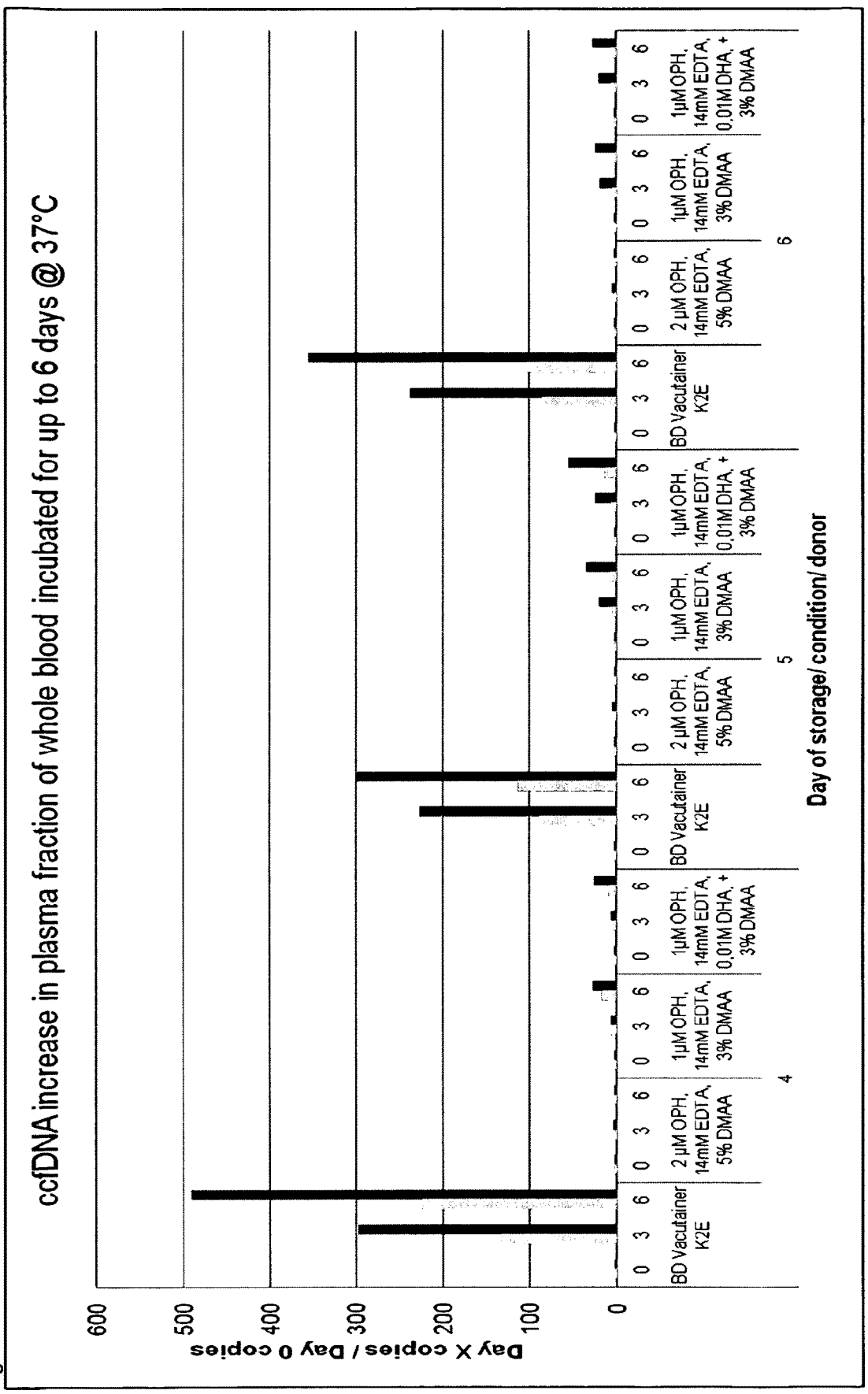
FIG. 17 is a diagram showing the ccfDNA increase in plasma fraction of whole blood incubated for up to 6 days at 37° C. (Example 13)

The samples were incubated at 37° C. for up to six days. Otherwise, the same procedure as in example 8 was followed. The results are shown in FIGS. 16 and 17. As can be seen, for all six donors, the level of ccfDNA was preserved when different concentrations of DMAA in combination with OPH and EDTA were added to the blood samples. Therefore, an efficient stabilization can be achieved with the method according to the present invention.

Example 14

Limit of Detection (LoD)

Extracellular nucleic acids are often comprised in very small amounts in the sample. Therefore, it is important to have a stabilization procedure which not only efficiently preserves the extracellular nucleic acids within the stabilized sample, but additionally allows to subsequently isolate the extracellular nucleic acids with high yield from the stabilized sample. Example 14 demonstrates that the stabilization method according to the present invention is superior to prior art stabilization methods in that the extracellular nucleic acids can be isolated with higher yield from the stabilized samples. This advantageously reduces the limit of detection and thus, allows to reliably determine also rare target nucleic acids within the population of extracellular nucleic acids.

The following stabilization solutions/tubes were compared:
1. Cell-free RNA BCT (Streck Inc, cat. #:218976—comprises a formaldehyde releaser as stabilizer)

2. BD Vacutainer K2E (BD, Cat. #: 367525—comprises EDTA)=reference
3. QGN stabilization (5% DMAA, 14 mM EDTA, 2 μM OPH (caspase inhibitor))

Whole blood samples were collected in cell-free RNA BCT and BD Vacutainer K2E tubes. To one half of blood collected in BD tubes, the QGN stabilization solution was added. Thus, the sample stabilized according to the invention comprise an additional amount of EDTA that is contributed by the BD Vacutainer stabilization. The samples were centrifuged at 3.000×rpm for 10 minutes, and the obtained plasma was aliquoted to 1.5 ml replicates. Afterwards, the following amounts of DNA spike-in control (1.000 bp) were added per sample: 1.000 copies, 5000 copies, 100 copies, 50 copies and 10 copies.

8 replicates of 500 to 10 copies/sample, 4 replicates of 1.000 copies/sample and 5 copies/sample were prepared. The samples were incubated for 3 days at room temperature. The sample preparation was done on the QIAsymphony SP automated system, using the QIAsymphony virus/bacteria Cell-free 1000 application which allows isolating extracellular nucleic acids from plasma samples. The nucleic acids were eluted in 60 μl; the subsequent PCR was performed in triplicates.

Figure 18:
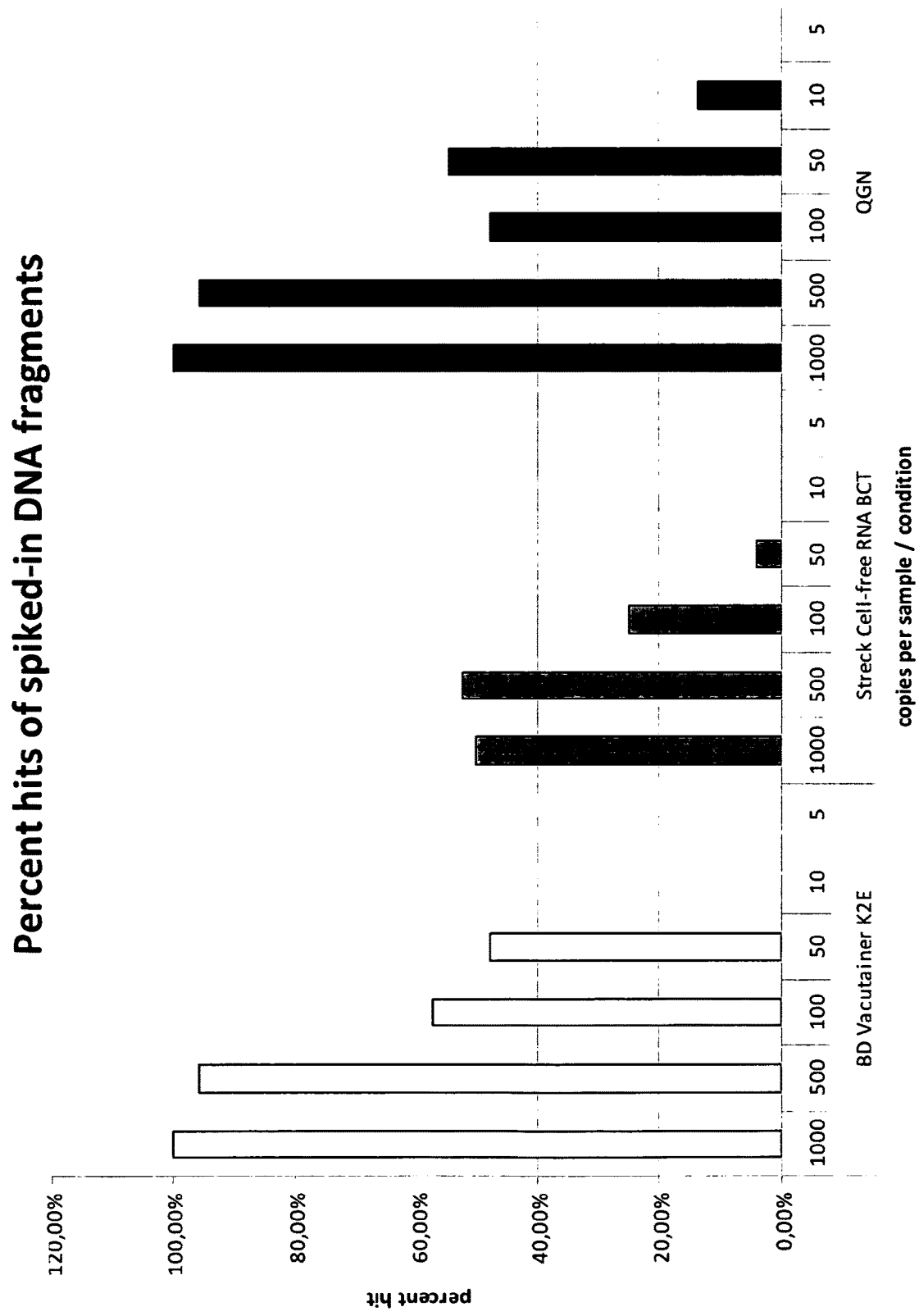
FIG. 18 is a diagram showing the percent hits of spiked-in DNA fragments (Example 14)

The results are shown in FIG. 18. As can be seen, 100% hit >1.000 copies per sample was obtained when using either the BD EDTA tubes or the stabilization solution according to the present invention. This shows that the isolation of nucleic acids is not impaired when using the stabilization solution according to the present invention. In contrast, the stabilization that is based on the use of a formaldehyde releaser (Streck) shows a strong inhibition of the nucleic acid isolation. As can be seen, significantly less nucleic acids could be isolated from the respective samples, even with those samples wherein 500 or even 1.000 copies were spiked in. Furthermore, FIG. 18 shows that the best sensitivity was obtained with a sample stabilized according to the present invention. Even for those embodiments wherein only 10 copies per sample were spiked in, still 13% positive PCR hits were obtained. Thus, the method according to the present invention not only efficiently stabilizes the samples such as blood samples but furthermore allows the subsequent recovery of even very low-abundant extracellular nucleic acids. This is an important advantage because it makes this method particularly suitable for diagnostic applications and e.g. the detection of rare target extracellular nucleic acids such as e.g. tumor derived extracellular nucleic acids or fetal nucleic acids. In particular, in the lower copy numbers, the stabilization solution that is based on the use of formaldehyde releasers had a very low performance and showed the highest limit of detection.

This is also confirmed by the following table:

| DNA Fragment | Tube/stabilizing | Dose for centile 95 [copies] | 95% confidence interval min [copies] | max [copies] |
| --- | --- | --- | --- | --- |
| 1000 bp | BD K2E | 386 | 230 | 995 |
| | Streck RNA | 9902 | 2909 | 164606 |
| | QGN | 599 | 319 | 1749 |

As can be seen from said table, for the 1.000 by fragment, the results achieved with EDTA sample and the stabilization solution of the present invention is comparable. Thus, the stabilization according to the invention does not impair the subsequent isolation of nucleic acids. Stabilization using a formaldehyde releaser showed the highest limit of detection and thus demonstrates that the subsequent isolation of the nucleic acid was strongly impaired. Therefore, the stabilization according to the present invention is suitable for sensitive detection of rare ccfDNA targets, which is not achieved by using state of the art methods.

Figure 19:
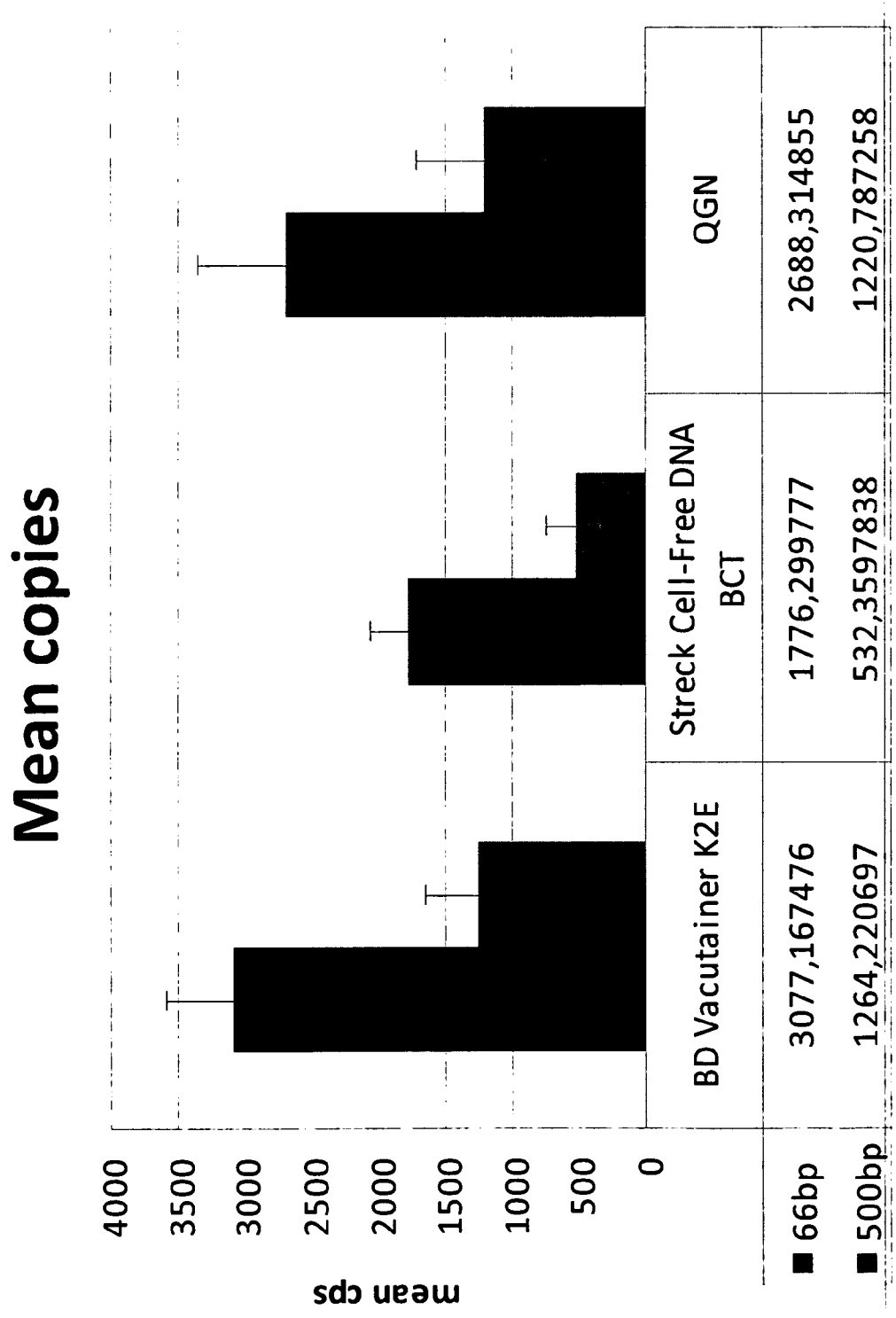
FIG. 19 is a diagram showing the mean copies (Example 14)
Figure 20:
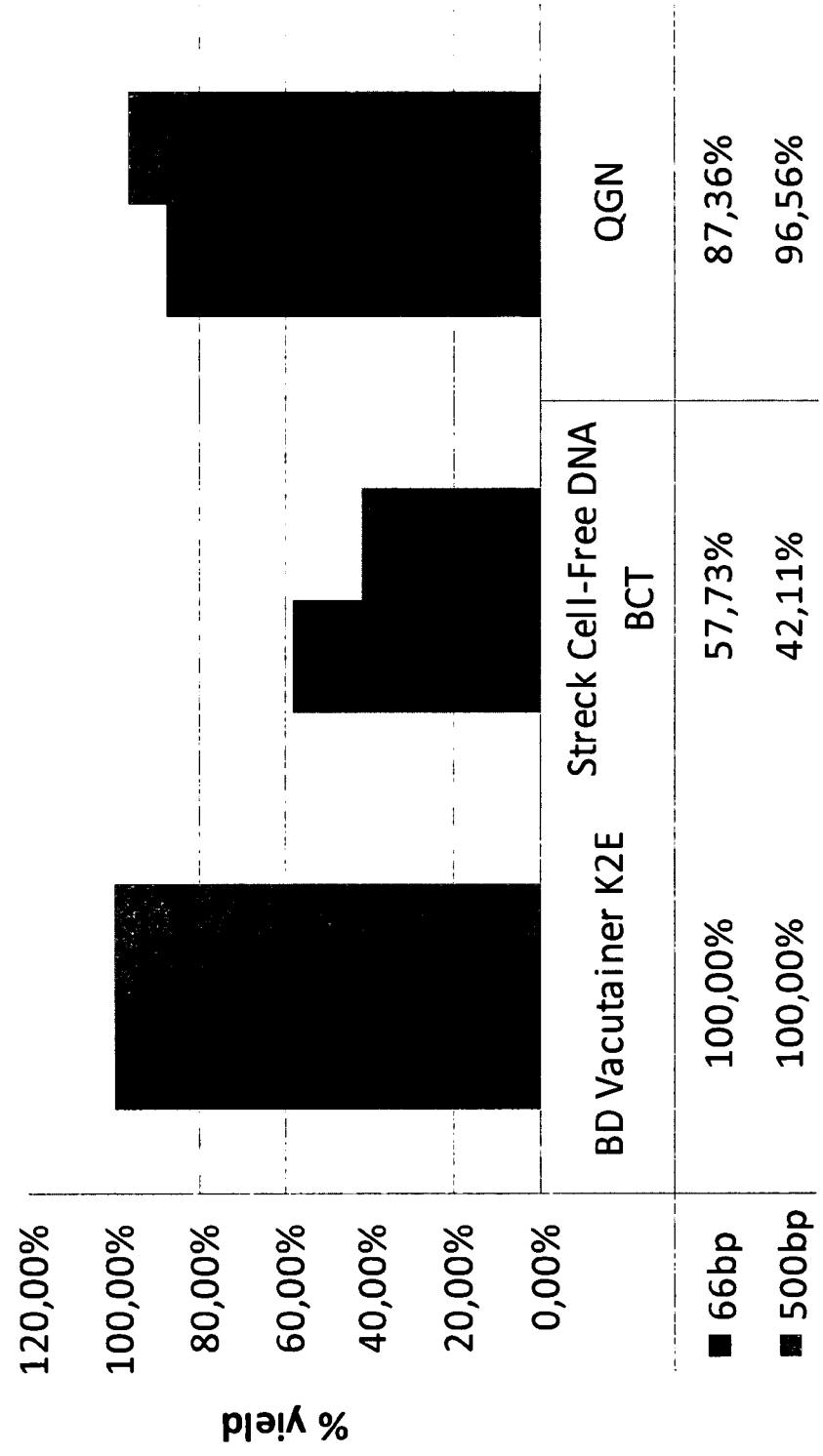
FIG. 20 is a diagram showing the percent of 18S compared to BD Vacutainer K2E (Example 14)

This is also confirmed by the results shown in FIGS. 19 and 20. As can be seen, comparable ccfDNA yields are obtained for EDTA stabilized samples and samples stabilized using the method according to the present invention (measured by 18 S rDNA qPCR). However, reduced ccfDNA yields were obtained for the stabilization, which involves the use of formaldehyde releasers (Streck tubes). The yield of formaldehyde stabilized samples was reduced by approximately 50% compared to the EDTA stabilized samples. In contrast, the stabilization reagent according to the present invention has no adverse effect on ccfDNA yield, when using conventional nucleic acid isolation methods. This is an important advantage as it allows to integrate the stabilization method according to the present invention into existing nucleic acid isolation procedures and workflows.

Example 15

Spike-In of 10^4 IU/ml HIV, HCV to Whole Blood Samples of 3 Donors

Whole blood samples were collected in BD Vacutainer 2KE tubes. Afterwards 2 ml of the following stabilization solution was added (given concentrations represent final concentration in stabilized blood solution). Then, HIV and HCV were added to the whole blood samples at 10^4 IU/ml.
1: 5% DMAA, 50 mg EDTA, 1 μM OPH, 0.05 M Inositol;
2: 5% DMAA, 50 mg EDTA, 1 μM OPH, 0.01M Maltitol;
3: 5% DMAA, 50 mg EDTA, 1 μM OPH, 0.05 M Inositol; 0.01M Maltitol;
4: 2% Inositol, 4% Sorbitol.

BD Vacutainer K2E stabilized samples served again as reference.

Figure 21:
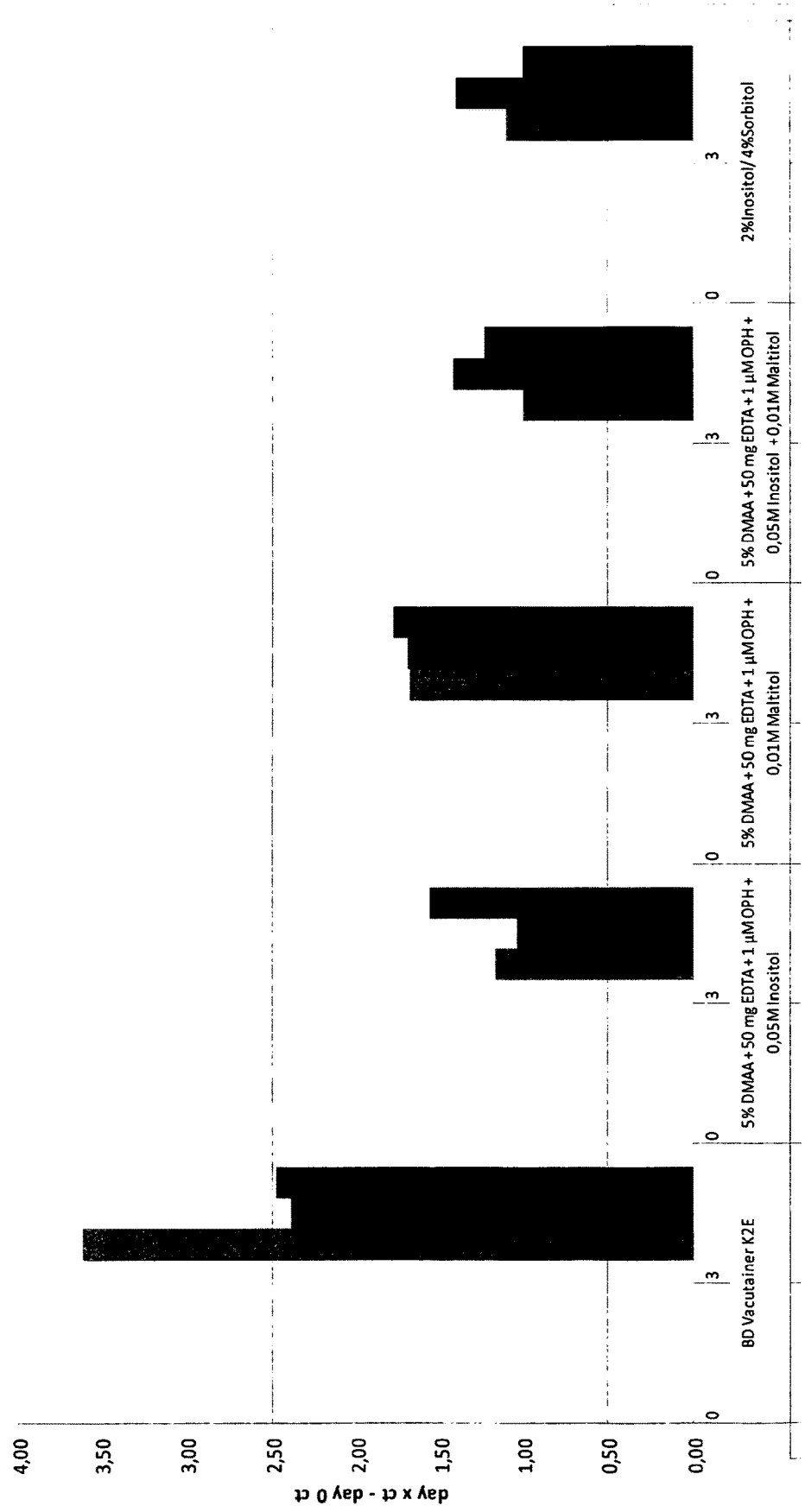
FIG. 21 is a diagram showing the decrease of HIV, incubated in whole blood at 37° C., purified from plasma (Example 15)

The samples were incubated at room temperature for up to six days at 37° C. On day 0 and day 3, replicates were processed as follows: the samples were centrifuged at 3.000 rpm, for 15 minutes at room temperature to collect the plasma. The obtained plasma was then again centrifuged at 16.000×g for 10 minutes, at 4° C. Extracellular nucleic acids obtained from the cleared plasma supernatant was purified using the QIAsymphony virus/bacteria Cell-free 1000 protocol. 1 ml plasma was used as input material, 60 μl volume was used for elution. The results are shown in FIG. 21. As can be seen, combining DMAA, EDTA and OPH with sugar alcohols allows to stabilize viral nucleic acids levels for up to three days at 37° C. Therefore, the method according to the present invention is particularly suitable for diagnostic applications and is also suitable for stabilizing the samples in environments wherein potentially no refrigerating facilities are available. ΔCt between day 0 and day 3 is reduced (ΔCt of approximately 2.5 to ΔCt of approximately 1) compared to the EDTA blood reference. Furthermore, stabilization effects were seen with a combination of Sorbitol in combination with Inositol (ΔCt of approximately 1 to 1.4).

Figure 22:
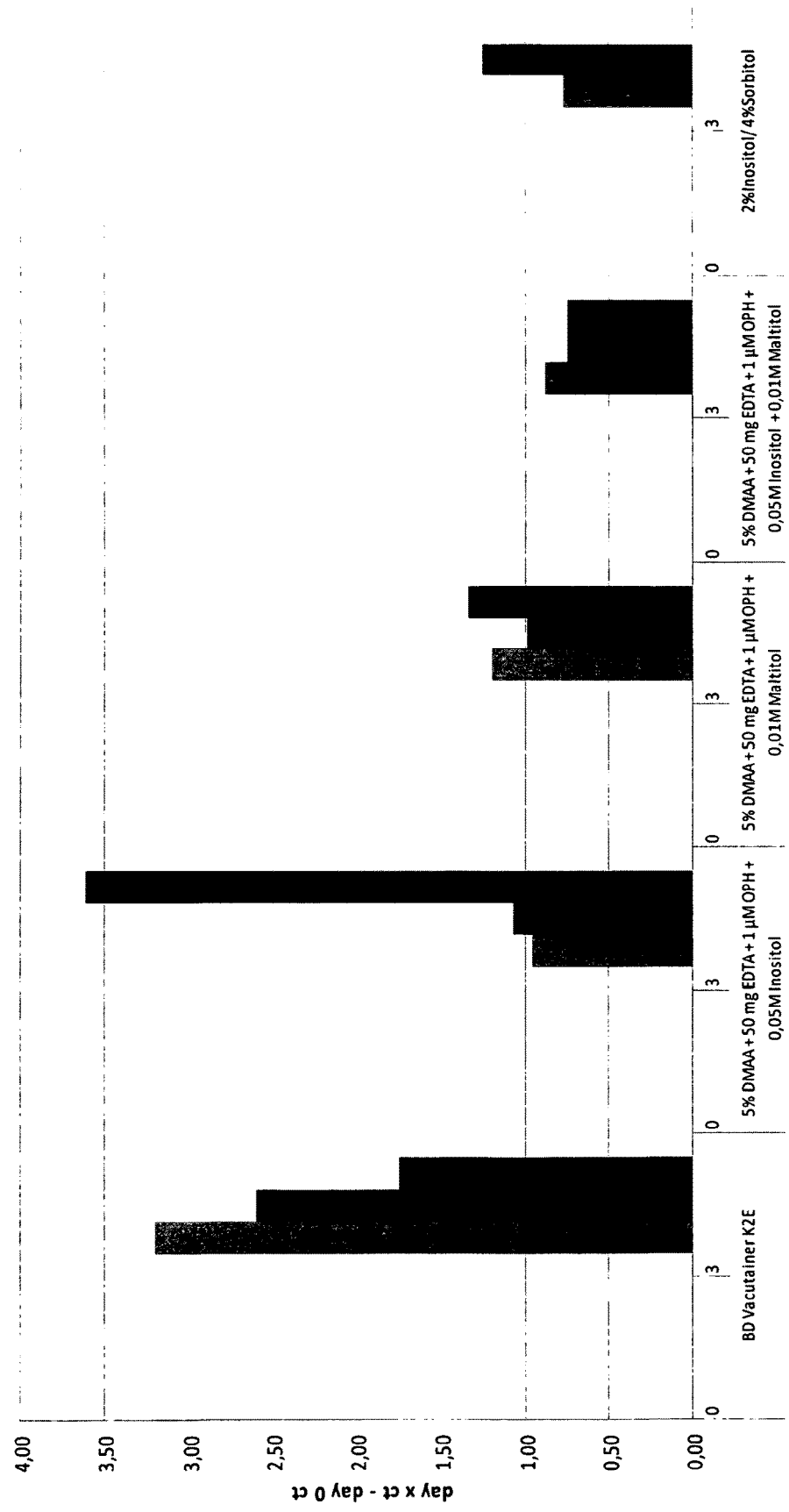
FIG. 22 is a diagram showing the decrease of HCV, incubated in whole blood at 37° C., purified from plasma (Example 15)

FIG. 22 shows the decrease of HCV in whole blood that was incubated at 37° C. Again, it is shown that when combining DMAA, EDTA and OPH with sugar alcohols, the HCV nucleic acid level is stabilized, indicated by a slowed decline in viral RNA levels, for three days at 37° C. ΔCt between day 0 and day 3 is reduced (ΔCt of approximately 1) compared to the EDTA blood reference (ΔCt of approximately 2-3). Furthermore, good stabilizing effects were achieved for Sorbitol in combination with Inositol.

Example 16

Stabilization with N,N Dimethylpropanamid and Caspase Inhibitor

Blood from two different donors was collected into 10 ml K2 EDTA tubes (BD). 4.5 ml of the respectively collected blood was mixed with 0.9 ml stabilization solution containing (per ml of stabilization solution): 34.2 mg K2 EDTA, 1.2 ml Quinoline-Val-Asp-CH2-OPH (caspase inhibitor) solution (1 mg dissolved in 388 μl DMSO) and 0.15 g or 0.3 g, or 0.45 g N,N dimethylpropanamide or 0.3 ml DMAA, respectively. Thereby, the following final concentration in the blood/stabilization mixture was obtained which is as follows:

5.7 mg K2 EDTA, 1 μM Quinoline-Val-Asp-CH2-OPH (caspase inhibitor) and 2.5, 5 or 7.5% (w/v) NN dimethylpropanamide or 5% (v/v) DMAA, respectively.

All stabilized blood samples were set up in triplicates per condition and test time point. At time point 0 (reference), immediately after mixing the stabilization solution and blood, plasma was generated and the ccfDNA was extracted. The residual blood sample was stored for three days and six days at room temperature. As a control, the EDTA stabilized blood sample was also stored for 3 and 6 days. The plasma was generated from the stabilized and unstabilized (EDTA) blood samples by inverting the blood containing tubes for four times. Then, the tubes were centrifuged for 15 minutes at 3.000 rpm/1912×g. 2.5 ml of the plasma fraction was transferred into a fresh 15 ml falcon tube and centrifuged for 10 minutes at 16.000×g. 2 ml of the respectively cleared plasma was used for isolating the extracellular nucleic acid using the QIAamp circulating nucleic acid kit.

Figure 23:
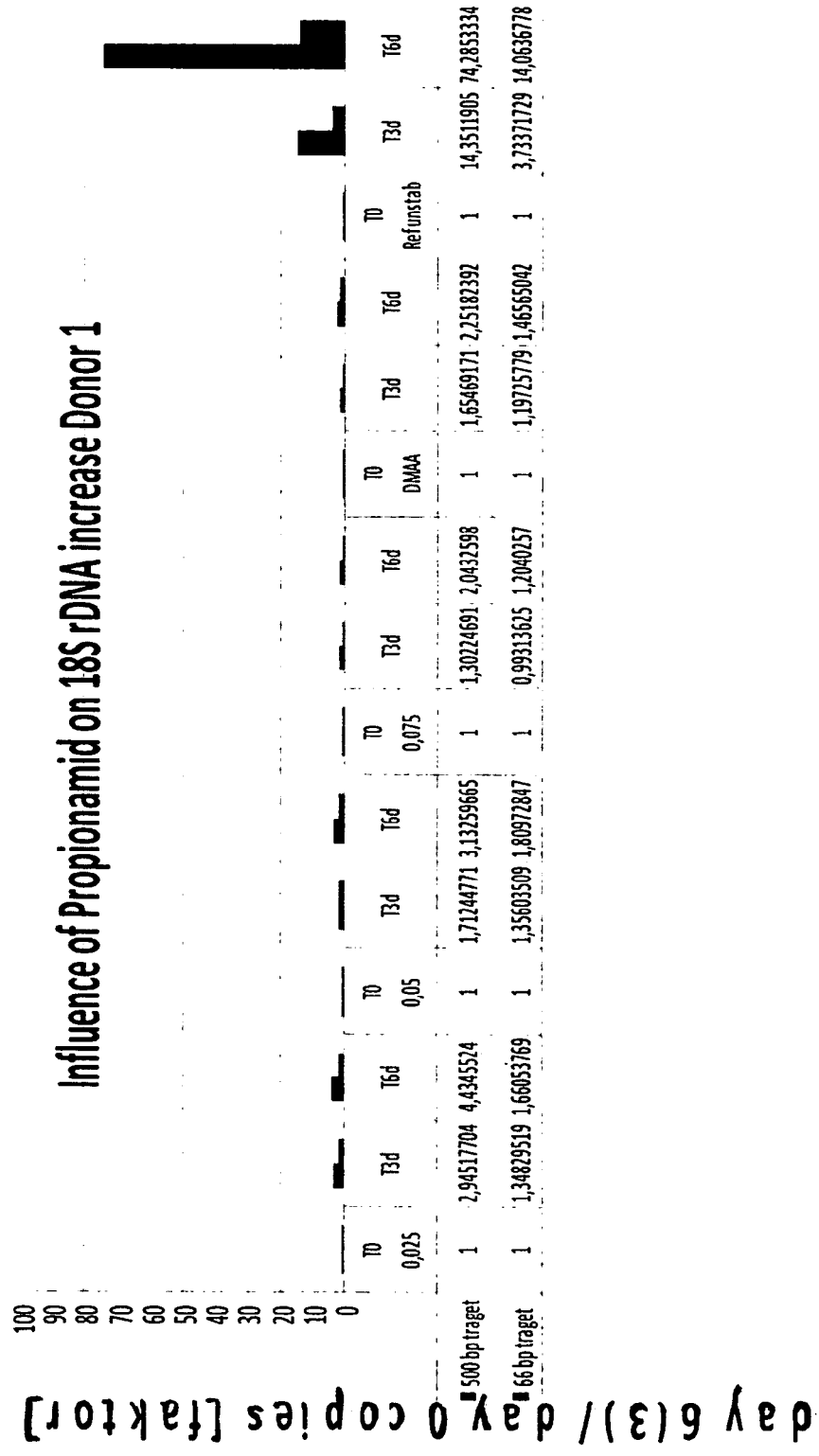
FIG. 23 is a diagram showing the influence of propionamid on 18S rDNA increase Donor 1 (Example 16)
Figure 24:
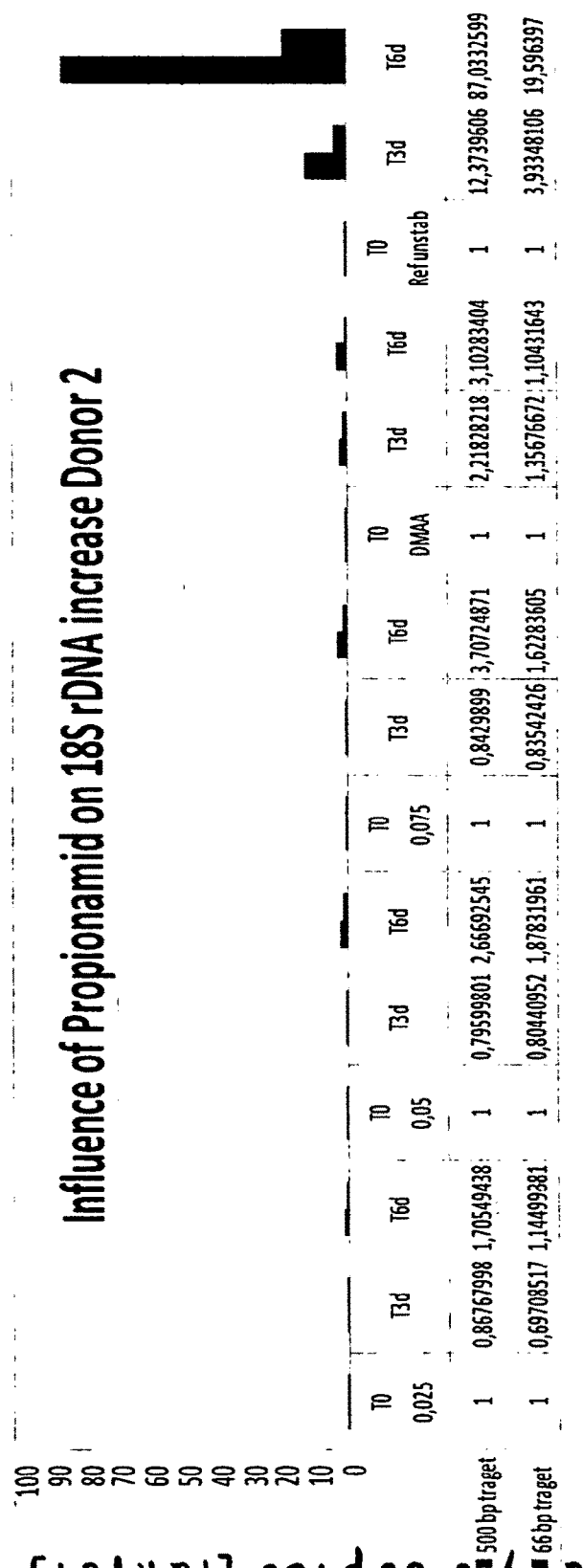
FIG. 24 is a diagram showing the influence of propionamid on 18S rDNA increase Donor 2 (Example 16)

The results are shown in shown in FIGS. 23 and 24. Shown is the increase of DNA relative to time point 0 with 2.5%, 5% and 7.5% N,N dimethylpropanamide or 5% DMAA (fold change) using different amplicon lengths of 18SrRNA gene. Bars indicate the mean of the triplicate samples per condition and test time point. All solutions according to the present inventions show significantly lower amounts of released DNA after storage for 3 and 6 days at room temperature compared to the unstabilized EDTA blood.

The invention claimed is:

1. A container suitable for collecting a biological sample, comprising:

a stabilizing composition suitable for stabilizing an extracellular nucleic acid population comprised in the sample, wherein said stabilizing composition comprises (a) a caspase inhibitor; and the container further comprising at least one compound according to formula 1

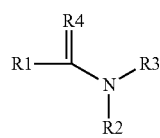

formula 1 wherein R1 is a hydrogen residue or an alkyl residue, R2 and R3 are identical or different hydrocarbon residues with a length of the carbon chain of 1-20 atoms arranged in a linear or branched manner, and R4 is an oxygen, sulphur or selenium residue.

2. The container according to claim 1, wherein the sample is a blood, plasma or serum sample.

3. The container according to claim 1, wherein the at least one compound according to formula 1 is comprised in the stabilizing composition.

4. The container according to claim 1, wherein in formula 1, R1 is a C1-C5 alkyl residue.

5. The container according to claim 1, wherein the stabilizing composition additionally comprises an anticoagulant.

6. The container according to claim 1, wherein the container is evacuated.

7. The container according to claim 1, wherein the stabilizing composition is capable of reducing (1) the release of genomic DNA from cells contained in the sample into the cell-free portion of the sample, and/or (2) the degradation of nucleic acids present in the sample.

8. The container according to claim 1, wherein a) the caspase inhibitor has one or more of the following characteristics:
   i) it is a pancaspase inhibitor,
   ii) it is a caspase-specific peptide,
   iii) it is a caspase-specific peptide modified by an aldehyde, nitrile or ketone compound, and/or
   iv) it is selected from the group consisting of Q-VD-OPh having the structure:

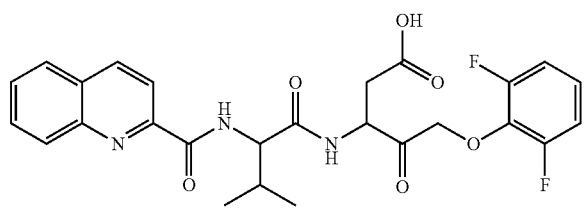 [SMILES: CC(C)C(NC(=O)c1ccc2ccccc2n1)C(=O)NC(CC(=O)O)C(=O)COc1c(F)cccc1F]

and Z-Val-Ala-Asp(OMe)-FMK having the structure:

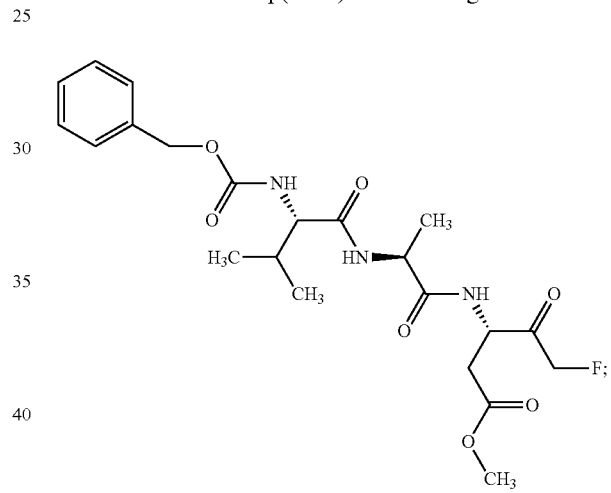

and/or b) wherein the compound according to formula 1 has one or more of the following characteristics:
   i) R1, R2 and R3 comprise 1 to 5 carbon atoms,
   ii) R1, R2 and R3 comprise 1 or 2 carbon atoms,
   iii) R4 is oxygen,
   iv) it is a N,N-dialkyl-carboxylic acid amide,
   v) it is selected from the group consisting of N,N-dimethylacetamide, N,N-diethylacetamide, N,N-dimethylformamide and N,N-diethylformamide, and/or
   vi) it is N,N-dimethylpropanamide.

9. The container according to claim 1, wherein the stabilizing composition additionally comprises at least one anticoagulant.

10. The container according to claim 9, wherein the at least one anticoagulant is a chelating agent.

11. The container according to claim 10, wherein the chelating agent is EDTA.

12. The container according to claim 1, wherein the stabilizing composition comprises the caspase inhibitor in a concentration that when the sample is added to the stabilizing composition, the resulting mixture has one or both of the following characteristics:

a) it comprises the caspase inhibitor in a concentration of at least 0.01 µM, at least 0.05 µM, at least 0.1 µM, at least 0.5 µM, at least 1 µM, at least 2.5 µM or at least 3.5 µM;

b) it comprises the caspase inhibitor in a concentration range selected from 0.01 µM to 100 µM, 0.05 µM to 100 µM, 0.1 µM to 50 µM, 1 µM to 40 µM, 1 µM to 30 µM, and 2.5 µM to 25 µM.

13. The container according to claim 1, wherein the stabilizing composition comprises in addition to the caspase inhibitor:

(b) at least one hypertonic agent which stabilizes cells potentially comprised in the sample, (c) the at least one compound according to formula 1; and (d) optionally at least one anticoagulant.

14. The container according to claim 1, wherein the stabilizing composition comprises the compound according to formula 1 in a concentration that when the sample is added to the stabilizing composition, the resulting mixture has one or both of the following characteristics:

a) it comprises the compound according to formula 1 in a concentration of at least 0.1%, at least 0.5%, at least 1%, at least 0.75%, at least 1%, at least 1.25% or at least 1.5%;

b) it comprises the compound according to formula 1 in a concentration range selected from 0.1% to 50%, 0.5% to 25%, 0.75% to 20%, 1% to 15%, and 1% to 10%.

15. The container according to claim 1, wherein the stabilizing composition comprises:

(a) at least one pancaspase inhibitor as caspase inhibitor, (b) at least one hypertonic agent, (c) the at least one compound according to formula 1, and (d) optionally a chelating agent as anticoagulant.

16. The container according to claim 1, wherein stabilization of the extracellular nucleic acid population is achievable without refrigeration for a time period selected from a) at least one day;
b) at least two days;
c) at least three days;
d) one day to three days;
e) one day to six days; and/or
f) one day to seven days.

17. The container according to claim 1, wherein the container has an open top, a bottom, and a sidewall extending therebetween defining a chamber, wherein the stabilization composition is comprised in the chamber.

18. The container according to claim 17, wherein the container is a tube, the bottom is a closed bottom, the container further comprises a closure in the open top, and the chamber is at a reduced pressure.

19. The container according to claim 18, wherein the closure is capable of being pierced with a needle or cannula, and wherein the reduced pressure is selected to draw a specified volume of a liquid sample into the chamber.

20. The container of claim 19, wherein the chamber is at a reduced pressure selected to draw a specified volume of a liquid sample into the chamber, and wherein the stabilizing composition is a liquid and is disposed in the chamber such that the volumetric ratio of the stabilising composition to the specified volume of the sample is selected from 10:1 to 1:20, 5:1 to 1:15, 1:1 to 1:10 and 1:2 to 1:5.

21. The container according to claim 1, suitable for collecting a blood sample, wherein the stabilizing composition further comprises an anticoagulant, and is capable of reducing (1) the release of genomic DNA from cells in the sample into the cell-free portion of the sample, and (2) the degradation of nucleic acids in the sample.

22. The container according to claim 13, wherein the stabilizing composition comprises the hypertonic agent in a concentration that when the sample is added to the stabilizing composition, the resulting mixture has one or both of the following characteristics:

a) it comprises the hypertonic agent in a concentration of at least 0.05M or at least 0.1M;

b) it comprises the hypertonic agent in a concentration range selected from 0.05M to 2M, 0.1 to 1.5M, 0.15M to 0.8M, 0.2M to 0.7M, and 0.1M to 0.6M.

23. The container according to claim 1, wherein the stabilizing composition has one or more of the following characteristics:

a) it is capable of reducing the release of genomic DNA from cells contained in the sample into the cell-free portion of the sample;

b) it is capable of reducing the degradation of nucleic acids present in the sample;

c) it is provided in a solid form;

d) it is provided in a liquid form; and/or e) it is capable of stabilizing the extracellular nucleic acid population contained in said sample at room temperature for at least 3 days.

24. The container according to claim 23, wherein in b), the stabilizing composition is capable of reducing the degradation of genomic DNA present in the sample.

25. The container according to claim 1, wherein the container additionally comprises the sample, and wherein the sample has one or more of the following characteristics:

a) it comprises extracellular nucleic acids;

b) it is selected from the group consisting of whole blood, plasma, serum, lymphatic fluid, urine, liquor, cerebrospinal fluid, ascites, milk, stool, bronchial lavage, saliva, amniotic fluid, semen/seminal fluid, swabs/smears, body fluids, body secretions, nasal secretions, vaginal secretions, wound secretions and excretions and cell culture supernatants;

c) it is a cell-depleted or cell containing body fluid;

d) it is selected from whole blood, plasma and/or serum; and/or e) it is whole blood.

26. A method for collecting a sample, comprising collecting a sample from a patient into a chamber of the container according to claim 1.

27. The container according to claim 13, wherein the hypertonic agent has one or more of the following characteristics:

i) it is uncharged,
ii) it stabilizes the cells comprised in the sample by inducing cell shrinking,
iii) it is cell impermeable,
iv) it is water-soluble,
v) it is a hydroxylated organic compound,
vi) it is a polyol,
vii) it is a hydroxy-carbonyl compound,
viii) it is a carbohydrate or a sugar alcohol, and/or
ix) it is dihydroxyacetone.

* * * * *